United States Patent
Yen et al.

(10) Patent No.: US 11,005,047 B2
(45) Date of Patent: May 11, 2021

(54) HETEROAROMATIC COMPOUND AND ORGANIC ELECTROLUMINESCENCE DEVICE USING THE SAME

(71) Applicants: Feng-Wen Yen, Taipei (TW); Li-Chieh Chuang, Nantou (TW); Tsun-Yuan Huang, Chiayi (TW)

(72) Inventors: Feng-Wen Yen, Taipei (TW); Li-Chieh Chuang, Nantou (TW); Tsun-Yuan Huang, Chiayi (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 297 days.

(21) Appl. No.: 15/976,879

(22) Filed: May 11, 2018

(65) Prior Publication Data
US 2019/0348609 A1    Nov. 14, 2019

(51) Int. Cl.
| | |
|---|---|
| C07D 307/94 | (2006.01) |
| H01L 51/00 | (2006.01) |
| C09K 11/06 | (2006.01) |
| C07D 495/20 | (2006.01) |
| C07D 409/04 | (2006.01) |
| C07D 519/00 | (2006.01) |
| C07D 405/12 | (2006.01) |
| H01L 51/50 | (2006.01) |

(52) U.S. Cl.
CPC ........ *H01L 51/0061* (2013.01); *C07D 307/94* (2013.01); *C07D 405/12* (2013.01); *C07D 409/04* (2013.01); *C07D 495/20* (2013.01); *C07D 519/00* (2013.01); *C09K 11/06* (2013.01); *H01L 51/0072* (2013.01); *H01L 51/0074* (2013.01); *C09K 2211/1018* (2013.01); *H01L 51/0071* (2013.01); *H01L 51/0073* (2013.01); *H01L 51/5012* (2013.01)

(58) Field of Classification Search
CPC ............. H01L 51/0061; H01L 51/0072; H01L 51/0074; H01L 51/0071; H01L 51/0073; H01L 51/5012; C07D 307/94; C07D 405/12; C07D 409/04; C07D 495/20; C07D 519/00; C09K 11/06; C09K 2211/1018
See application file for complete search history.

(56) References Cited

U.S. PATENT DOCUMENTS

2017/0346012 A1* 11/2017 Koo .................... H01L 51/0072

* cited by examiner

*Primary Examiner* — Vu A Nguyen

(57) ABSTRACT

A heteroaromatic compound which can be used as the fluorescent guest material in the light emitting layer of the organic electroluminescence device is disclosed. The organic electroluminescence device employing the heteroaromatic compound of the present invention shows lower power consumption, higher efficiency, and longer half-life time than the existed organic electroluminescence devices.

9 Claims, 1 Drawing Sheet

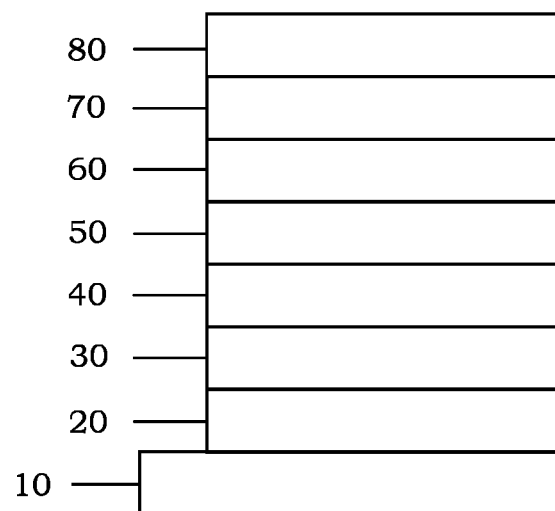

HETEROAROMATIC COMPOUND AND ORGANIC ELECTROLUMINESCENCE DEVICE USING THE SAME

FIELD OF INVENTION

The present invention relates to a heteroaromatic compound and, more particularly, to an organic electroluminescence device using the heteroaromatic compound.

BACKGROUND OF THE INVENTION

An organic electroluminescence (organic EL) device is an organic light-emitting diode (OLED) in which the light emitting layer is a film made from organic compounds, which emits light in response to the electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

Typically, the organic EL device is composed of organic material layers sandwiched between two electrodes. The organic material layers include, e.g., hole injection layer (HIL), hole transporting layer (HTL), emitting layer (EML), electron transporting layer (ETL), and electron injection layer (EIL). The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only ~20% of the light out-coupling efficiency of the device. In contrast to fluorescent electroluminescence devices, phosphorescent organic EL devices make use of spin-orbit interactions to facilitate intersystem crossing between singlet and triplet states, thus obtaining emission from both singlet and triplet states and the internal quantum efficiency of electroluminescence devices from 25% to 100%.

For full-colored displays using organic EL devices, the organic materials used in the organic EL devices are still unsatisfactory in half-life time, driving voltage, and current efficiency. Therefore, there is still a need for an organic compound that can lower the driving voltage, increase the current efficiency, and prolong the half-life time for the organic EL device.

SUMMARY OF THE INVENTION

Accordingly, an object of the present invention is to provide a novel heteroaromatic compound, which can be used as a fluorescent dopant material in the emitting layer of the organic EL device to improve the power consumption, current efficiency, and life time of the device.

Another object of the invention is to provide a heteroaromatic compound and an organic EL device using the same, which can operate under reduced voltage and exhibit higher current efficiency and longer half-life time.

According to the present invention, a heteroaromatic compound which can be used in organic EL devices is disclosed. The heteroaromatic compound is represented by the following formula (1):

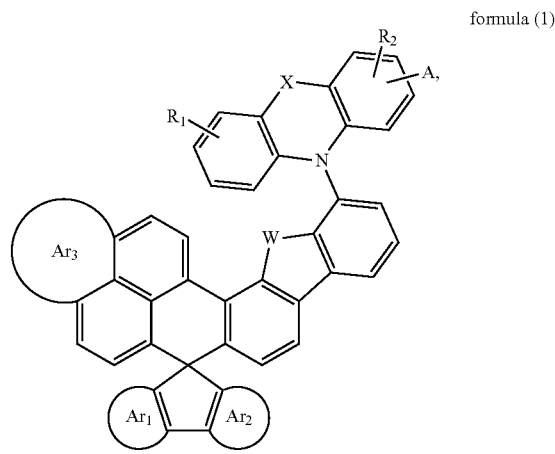

formula (1)

wherein $Ar_1$ and $Ar_2$ are independently an aryl group or a heteroaryl group having 4 to 6 ring carbon atoms; $Ar_3$ is a cycloalkyl group, a cycloalkenyl group, or an aryl group having 5 to 6 ring carbon atoms; $R_1$ and $R_2$ are independently a hydrogen atom, a substituted or unsubstituted alkyl group having 1 to 36 carbon atoms, a substituted or unsubstituted aryl group having 6 to 36 carbon atoms, or a substituted or unsubstituted aralkyl group having 6 to 36 carbon atoms; W represents a divalent bridge selected from the group consisting of O, S, $CR_3R_4$, $NR_5$, and $SiR_6R_7$, and $R_3$ to $R_7$ are independently a hydrogen atom or a substituted or unsubstituted alkyl group having 1 to 20 carbon atoms; X is absent or a divalent bridge selected from the group consisting of O, S, $CR_8R_9$, $NR_{10}$, and $SiR_{11}R_{12}$; A is absent or represents formula (2) below:

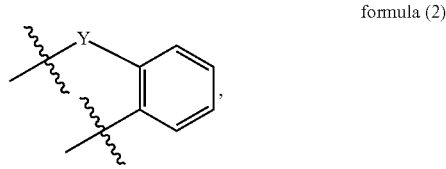

formula (2)

wherein Y represents a divalent bridge selected from the group consisting of O, S, $CR_{13}R_{14}$, $NR_{15}$, and $SiR_{16}R_{17}$; and $R_8$ to $R_{17}$ are independently a hydrogen atom, a substituted or unsubstituted alkyl group having 1 to 36 carbon atoms, a substituted or unsubstituted aryl group having 6 to 36 carbon atoms, a substituted or unsubstituted aralkyl group having 6 to 36 carbon atoms, or a substituted or unsubstituted heteroaryl group having 3 to 36 carbon atoms.

The present invention further discloses an organic electroluminescence device. The organic electroluminescence device comprises a pair of electrodes composed of a cathode and an anode, and a light emitting layer between the pair of electrodes. The light emitting layer comprises the heteroaromatic compound of formula (1).

BRIEF DESCRIPTION OF THE DRAWINGS

The FIGURES a schematic view showing an organic EL device according to an embodiment of the present invention.

DESCRIPTION OF THE PREFERRED EMBODIMENTS

What probed into the invention is the heteroaromatic compound and organic EL device using the heteroaromatic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, a heteroaromatic compound which can be used as the fluorescent dopant material of the light emitting layer in the organic EL device is disclosed. The heteroaromatic compound is represented by the following formula (1):

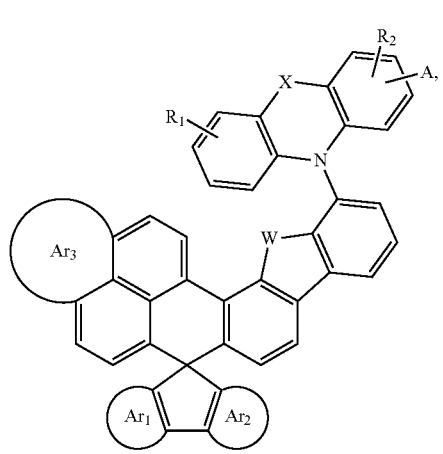

formula (1)

wherein $Ar_1$ and $Ar_2$ are independently an aryl group or a heteroaryl group having 4 to 6 ring carbon atoms; $Ar_3$ is a cycloalkyl group, a cycloalkenyl group, or an aryl group having 5 to 6 ring carbon atoms; $R_1$ and $R_2$ are independently a hydrogen atom, a substituted or unsubstituted alkyl group having 1 to 36 carbon atoms, a substituted or unsubstituted aryl group having 6 to 36 carbon atoms, or a substituted or unsubstituted aralkyl group having 6 to 36 carbon atoms; W represents a divalent bridge selected from the group consisting of O, S, $CR_3R_4$, $NR_5$, and $SiR_6R_7$, and $R_3$ to $R_7$ are independently a hydrogen atom or a substituted or unsubstituted alkyl group having 1 to 20 carbon atoms; X is absent or a divalent bridge selected from the group consisting of O, S, $CR_8R_9$, $NR_{10}$, and $SiR_{11}R_{12}$; A is absent or represents formula (2) below:

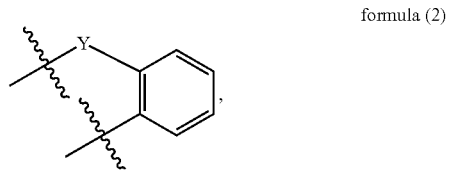

formula (2)

wherein Y represents a divalent bridge selected from the group consisting of O, S, $CR_{13}R_{14}$, $NR_{15}$, and $SiR_{16}R_{17}$; and $R_8$ to $R_{17}$ are independently a hydrogen atom, a substituted or unsubstituted alkyl group having 1 to 36 carbon atoms, a substituted or unsubstituted aryl group having 6 to 36 carbon atoms, a substituted or unsubstituted aralkyl group having 6 to 36 carbon atoms, or a substituted or unsubstituted heteroaryl group having 3 to 36 carbon atoms.

In some embodiments, $Ar_1$ and $Ar_2$ are independently

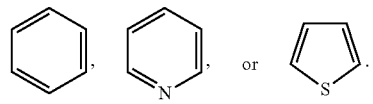

In some embodiments, $Ar_3$ is

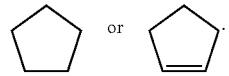

Preferably, the heteroaromatic compound is one of the following compounds:

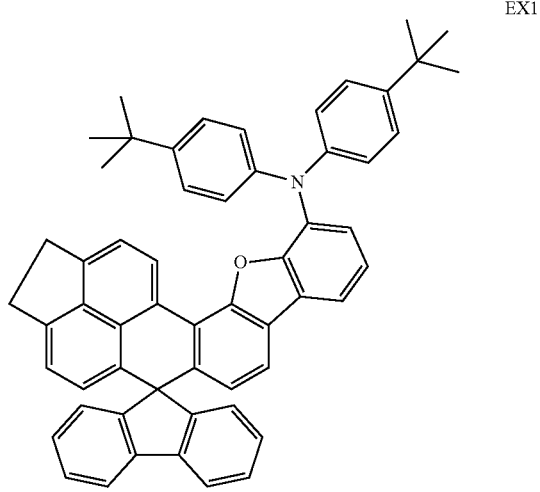

EX1

-continued
EX2
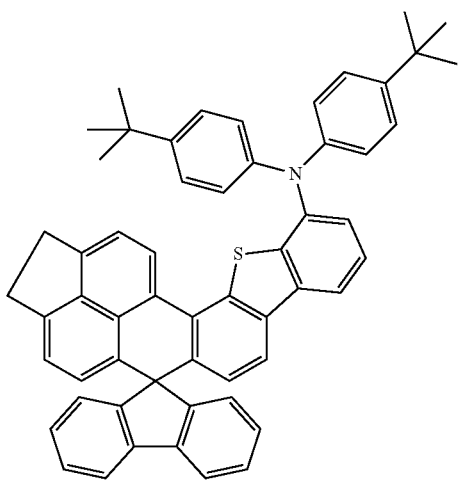
EX3
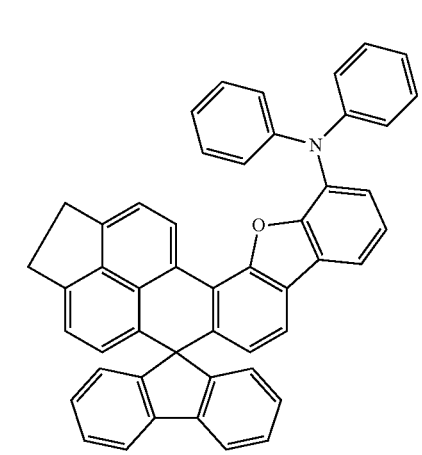
EX5
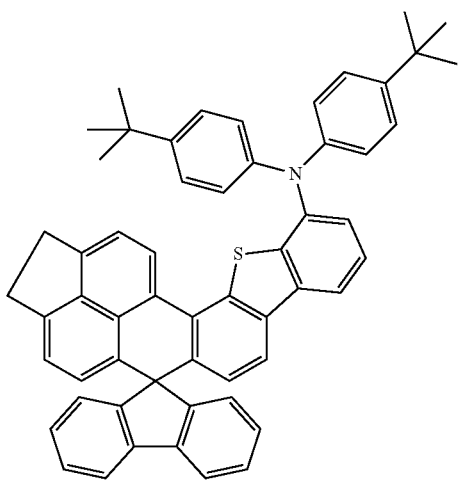
EX6
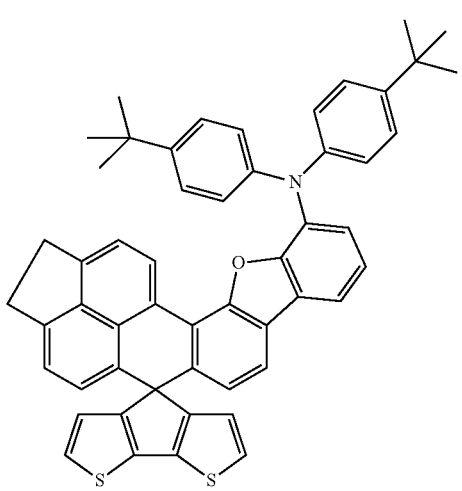
EX4
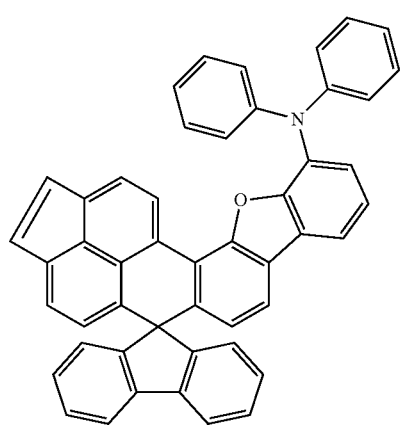
EX7
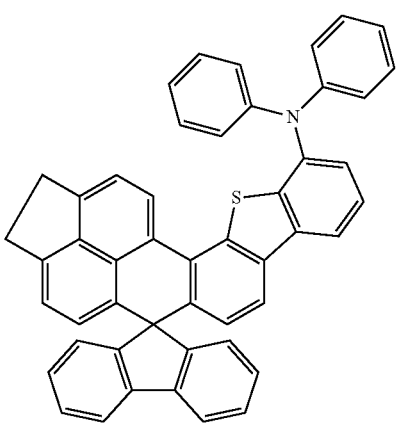

-continued
EX8
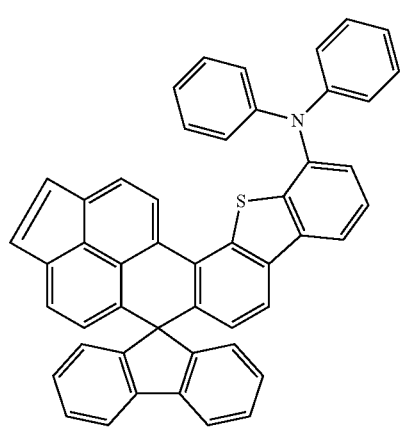
EX9
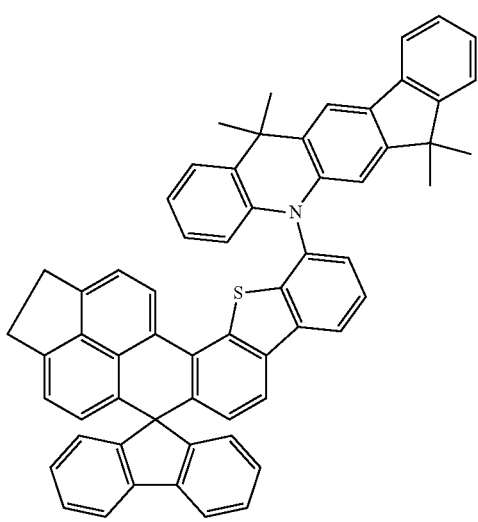
EX10
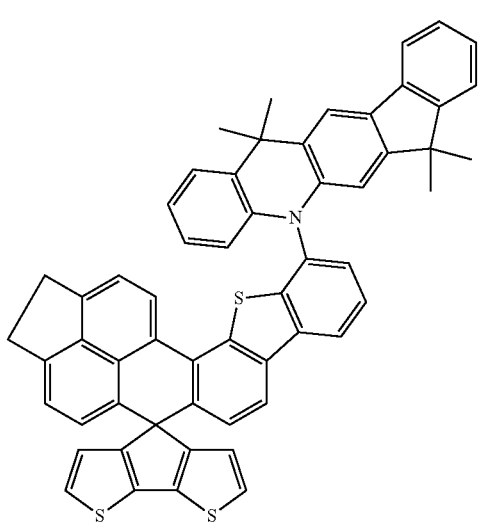
-continued
EX11
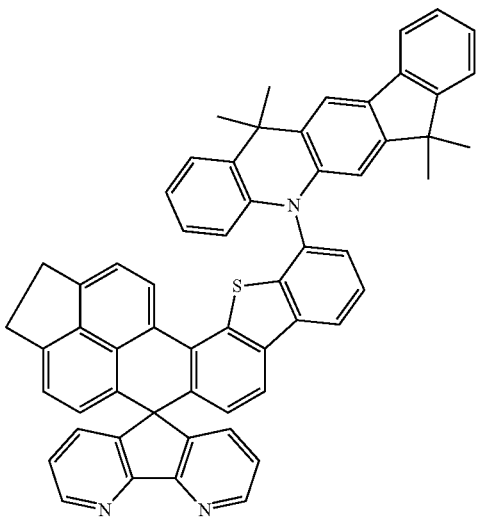
EX12
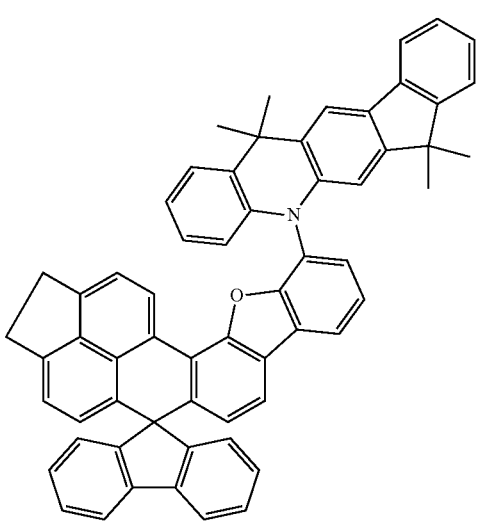
EX13
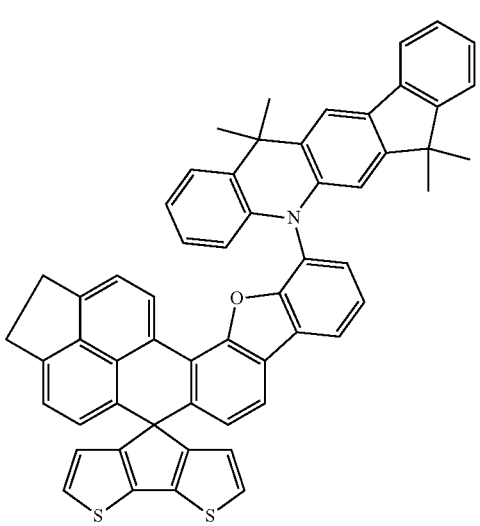

-continued
EX14
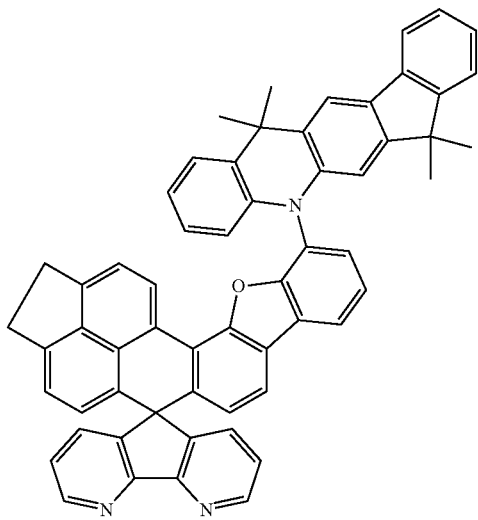
EX17
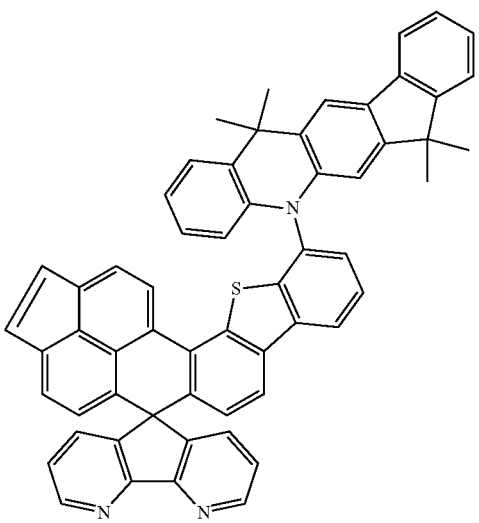
EX15
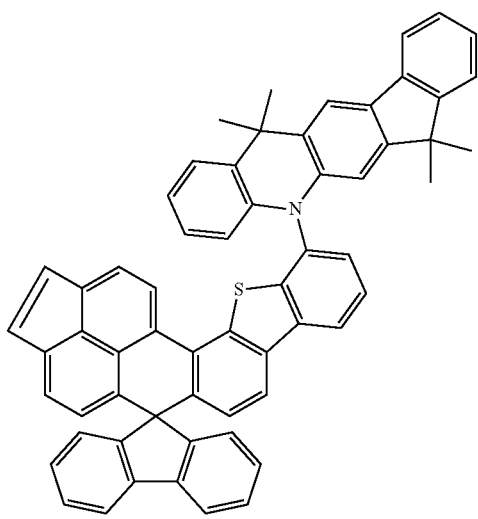
EX18
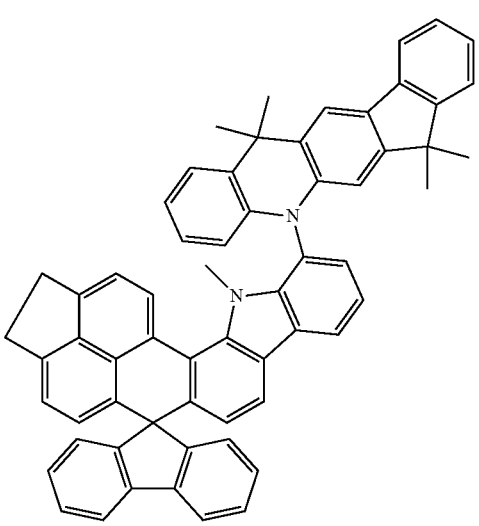
EX16
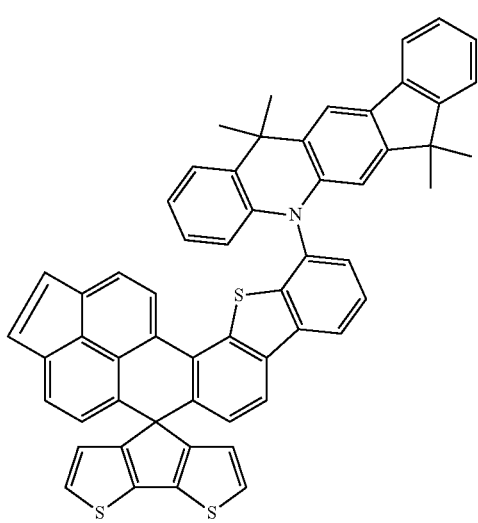
EX19
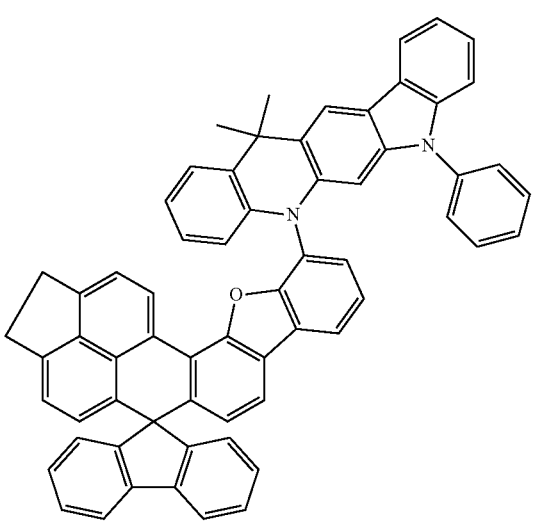

EX20
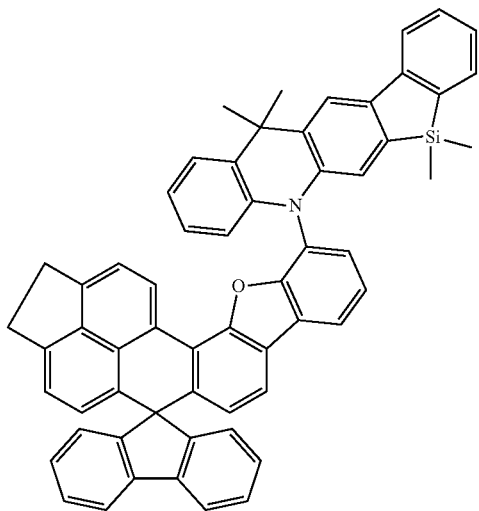
EX21
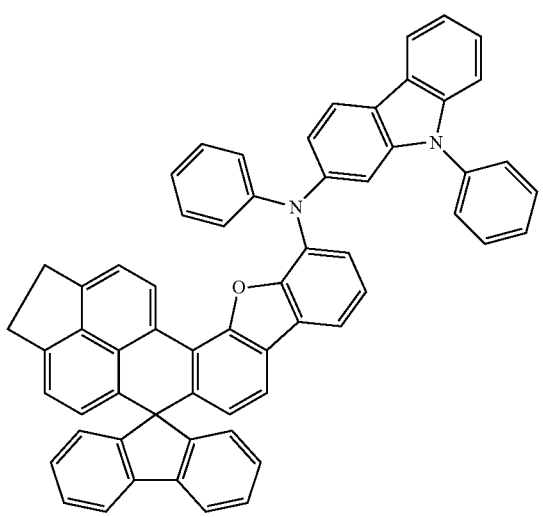
EX22
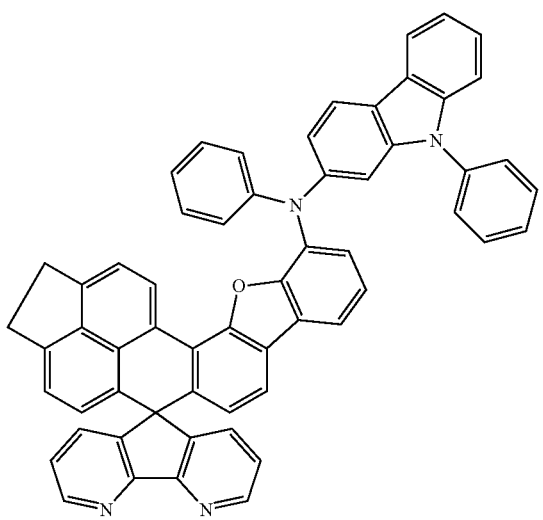
EX23
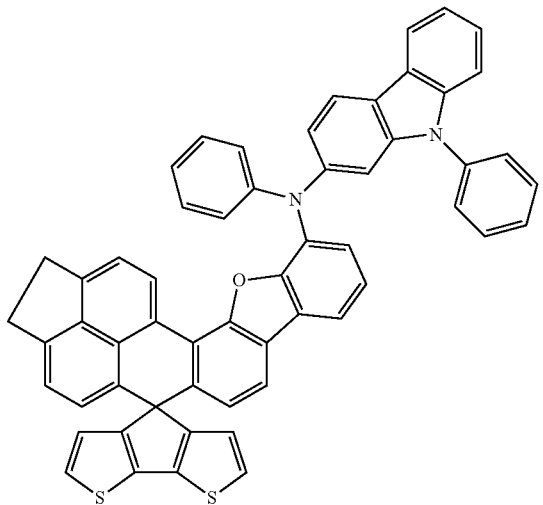
EX24
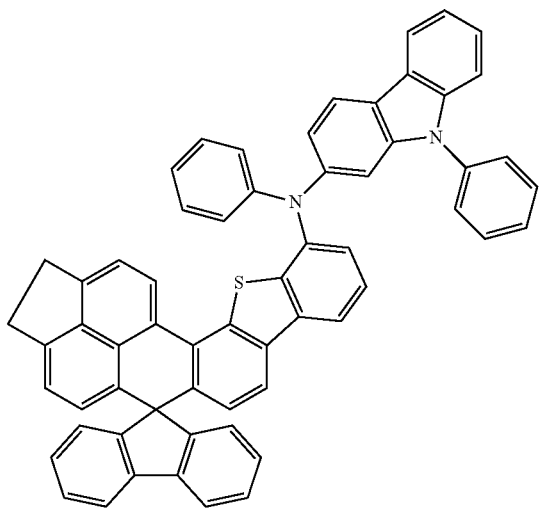
EX25
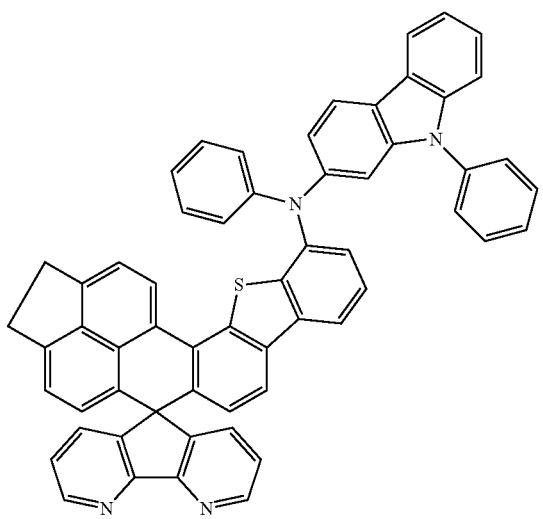

-continued
EX26
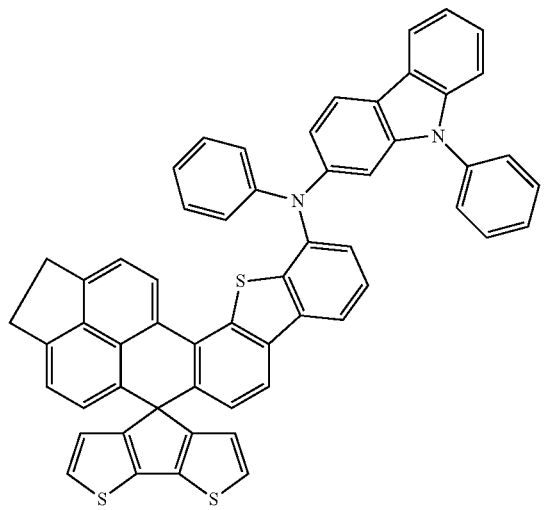
EX29
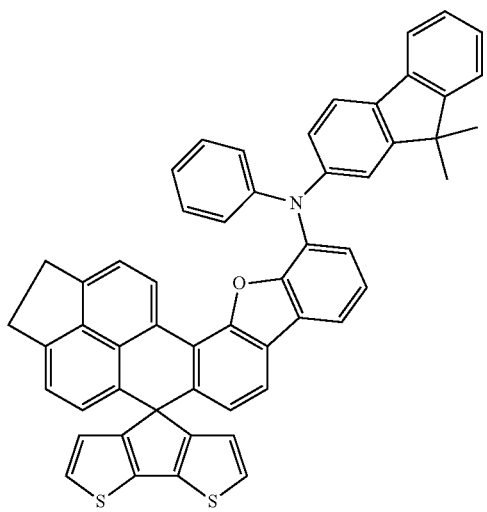
EX27
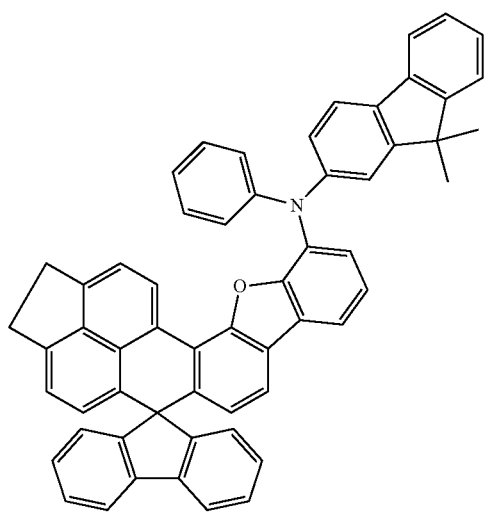
EX30
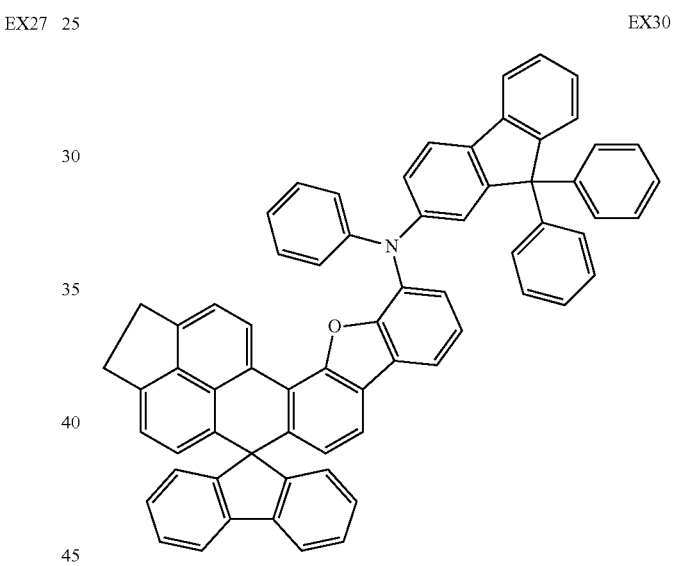
EX28
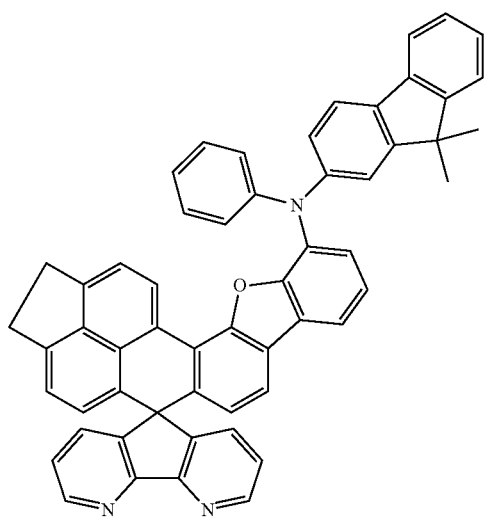
EX31
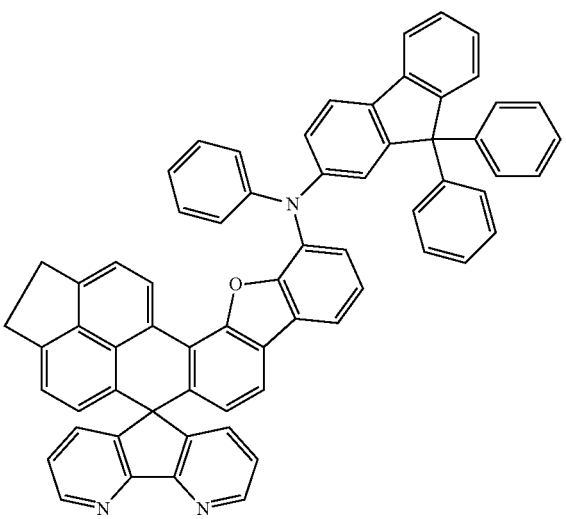

EX32
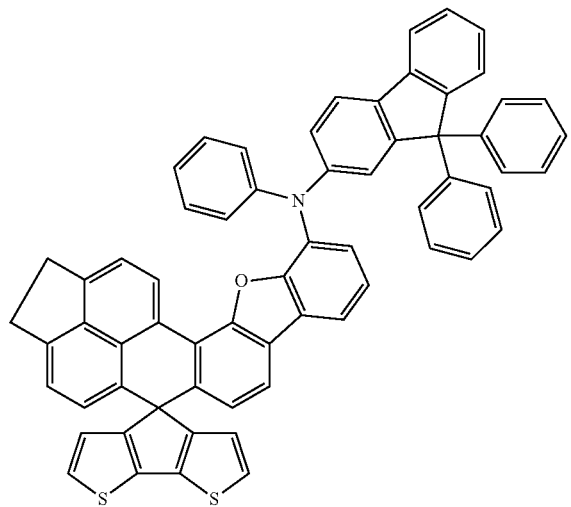
EX33
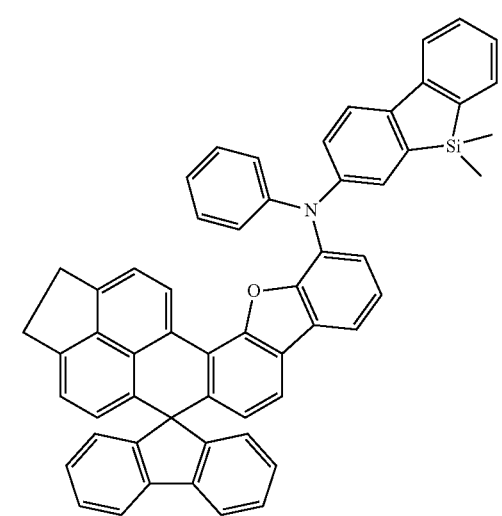
EX34
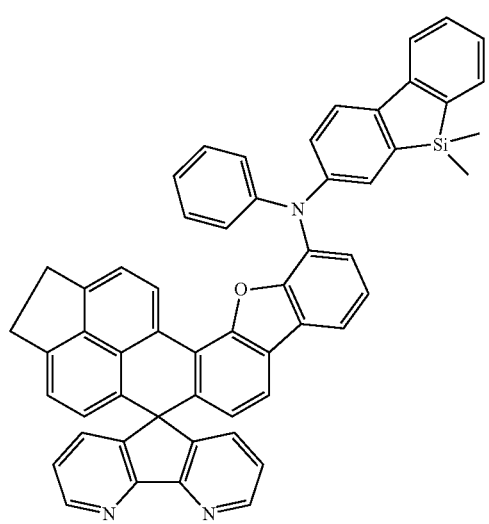
EX35
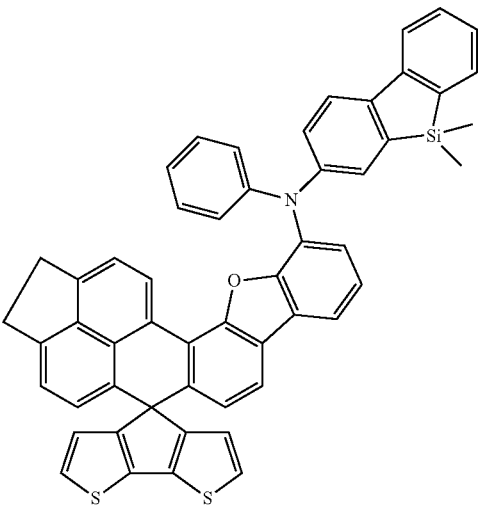
EX36
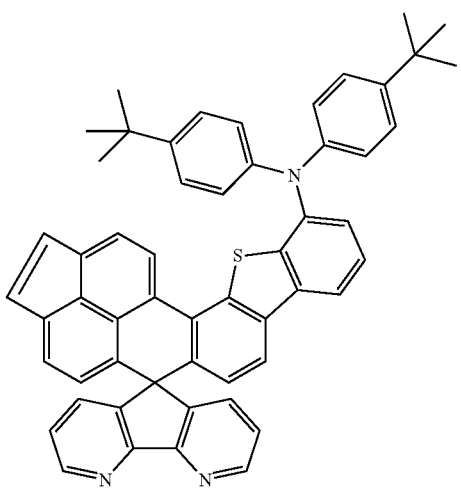
EX37
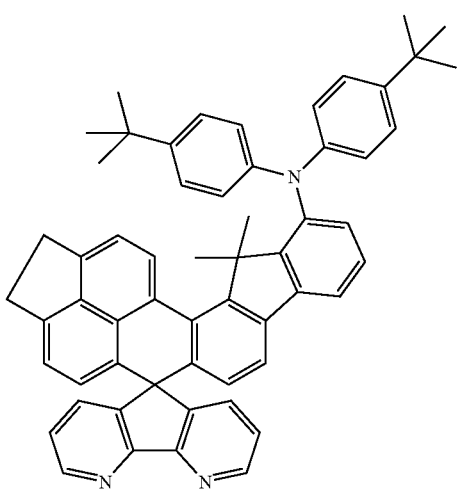

EX38
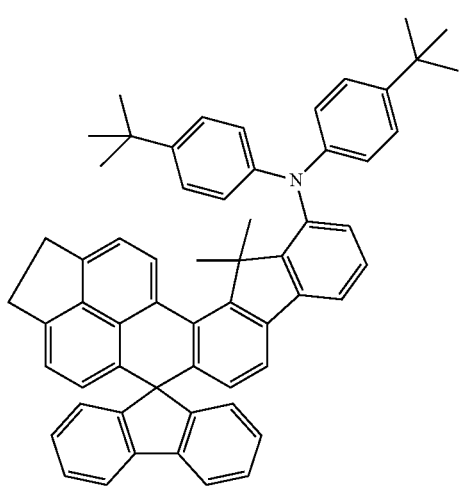
EX39
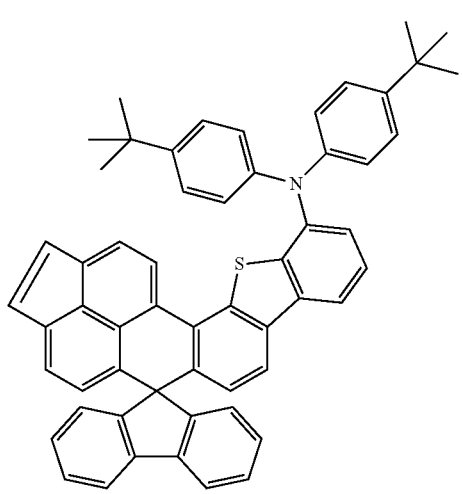
EX40
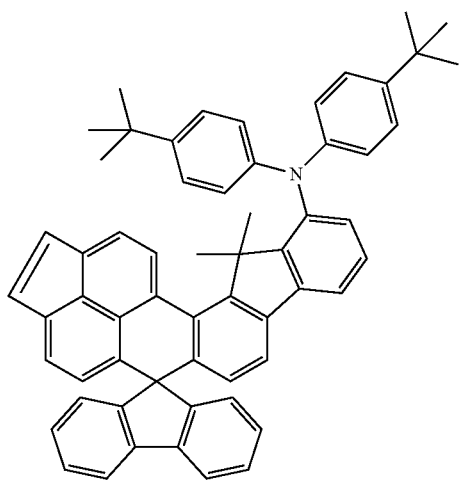
EX41
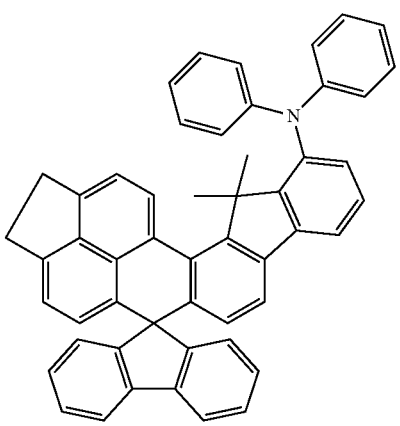
EX42
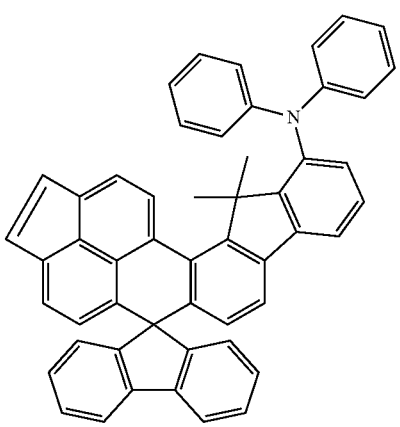
EX43
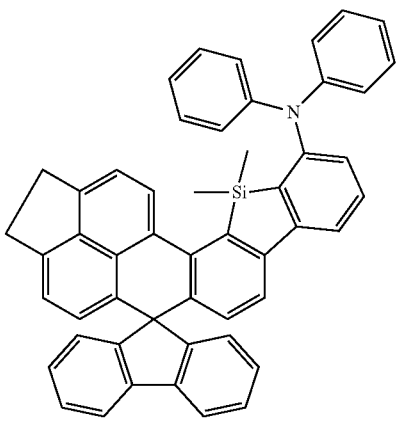

EX44
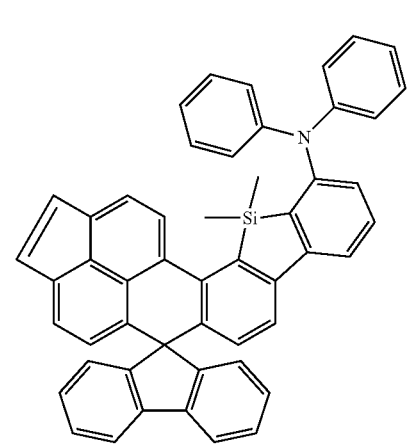
EX47
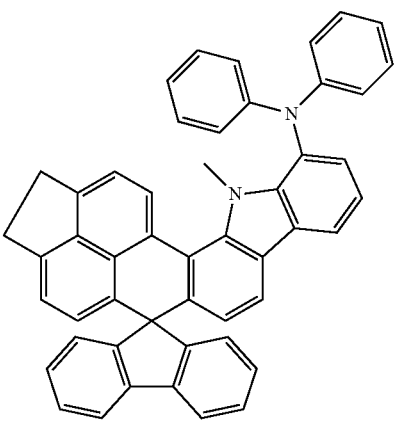
EX45
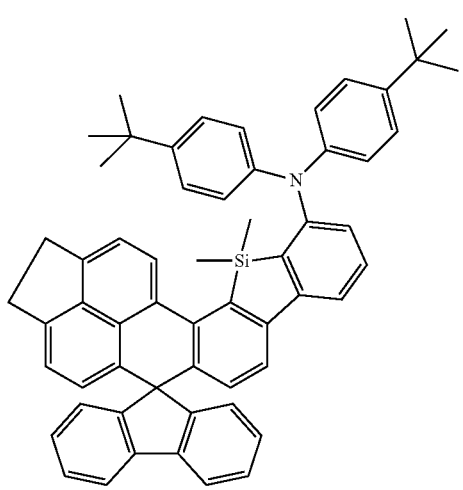
EX48
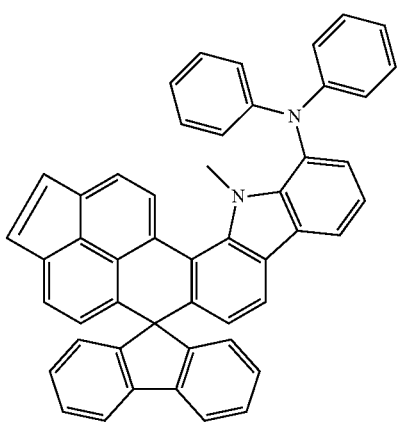
EX46
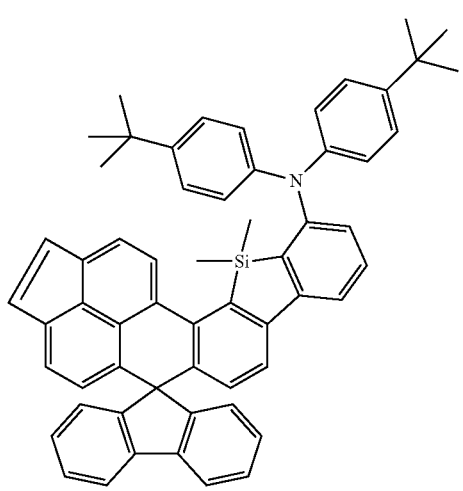
EX49
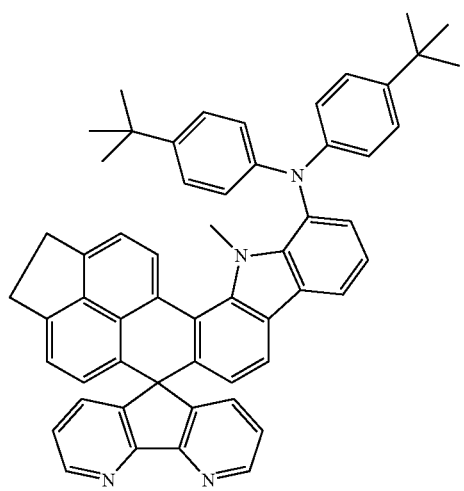

-continued
EX50
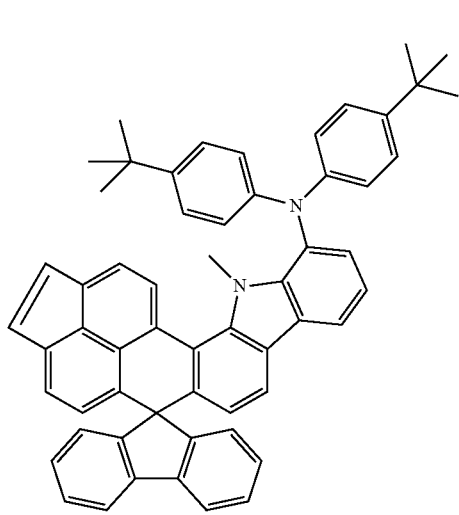
EX51
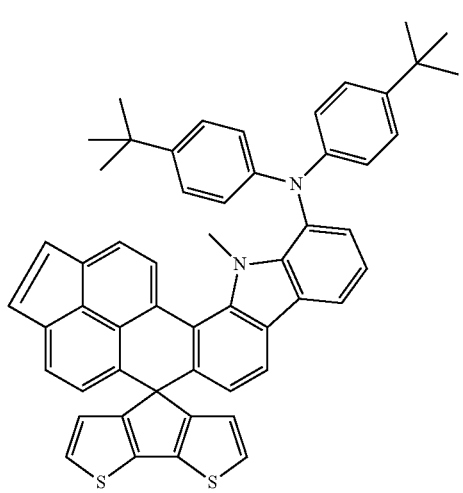
EX52
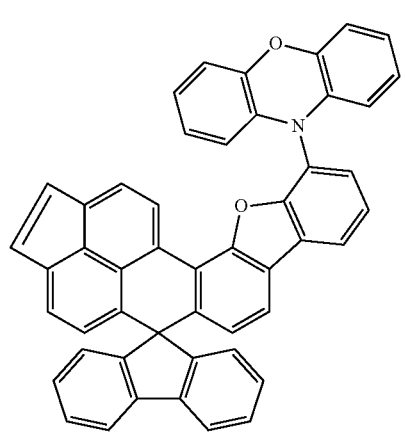
-continued
EX53
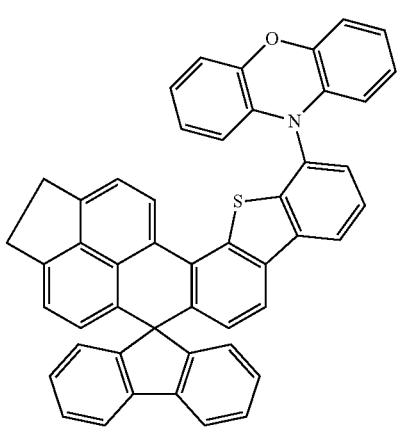
EX54
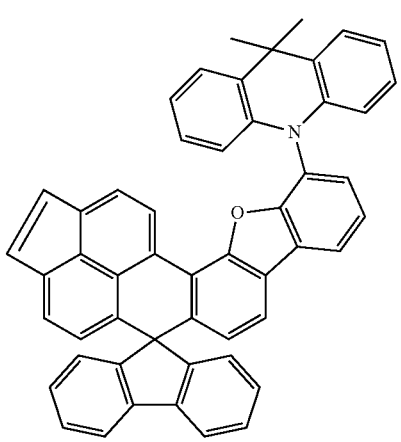
EX55
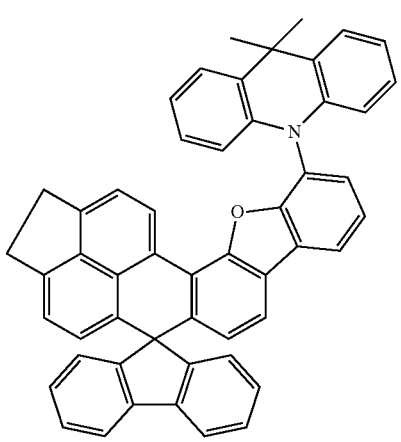

EX56
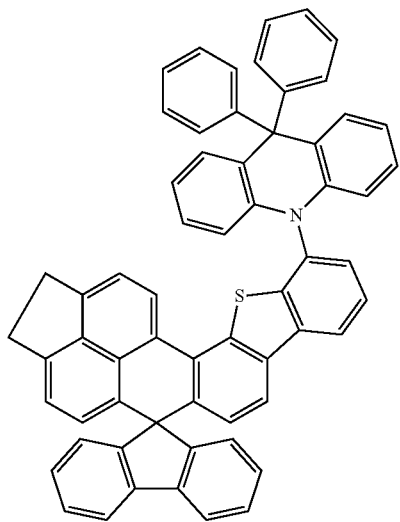
EX57
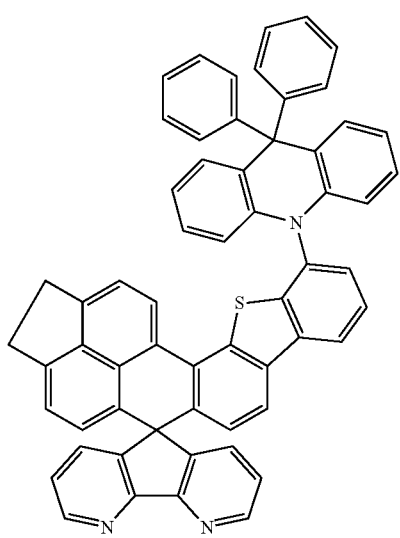
EX58
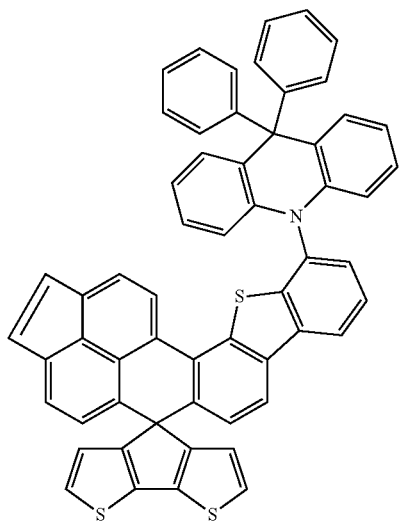
EX59
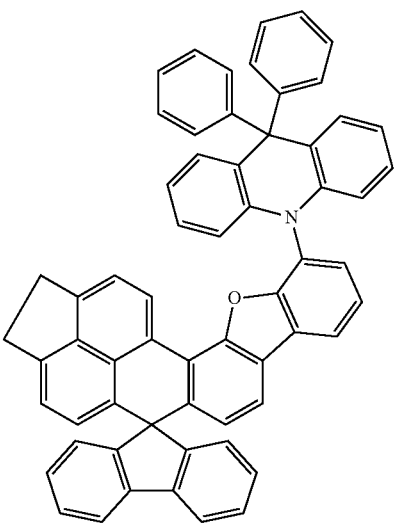
EX60
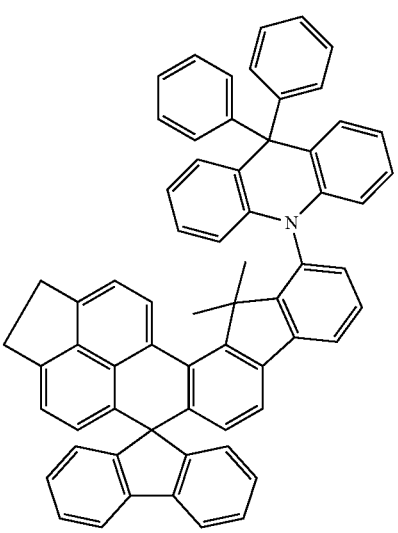
EX61
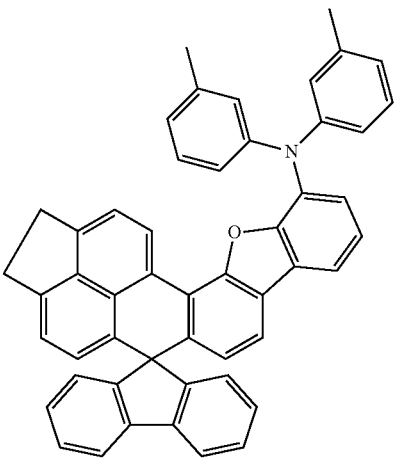

EX62
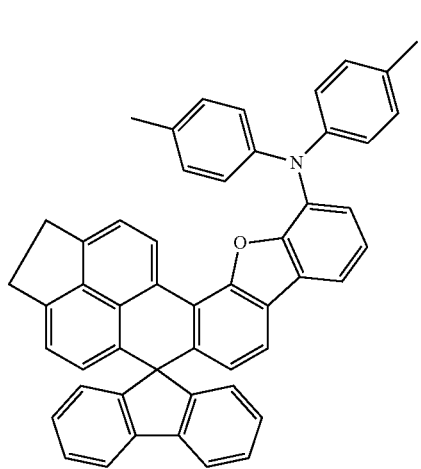
EX63
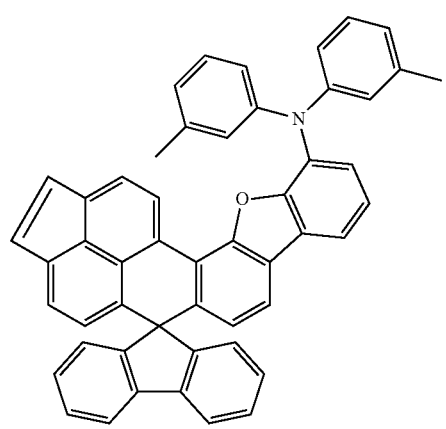
EX64
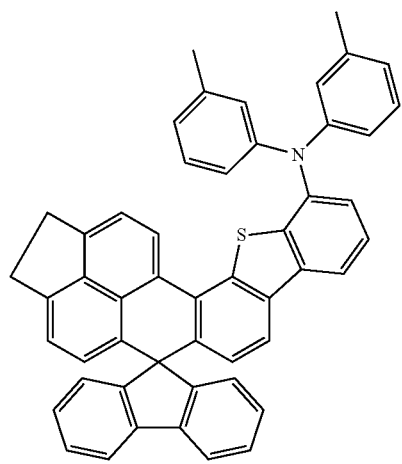
EX65
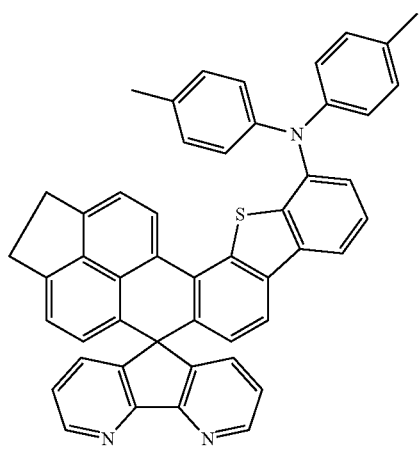
EX66
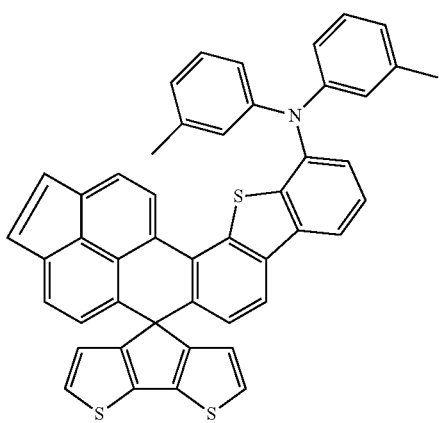
EX67
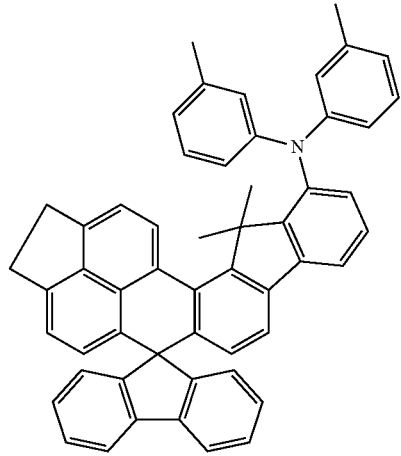

EX68
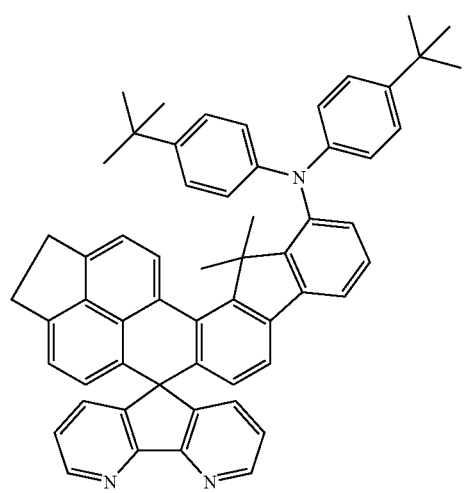
EX69
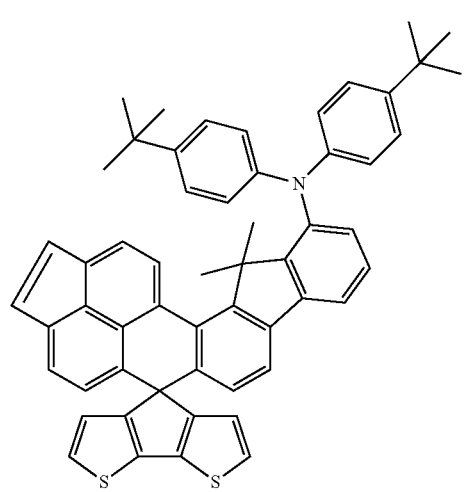
EX70
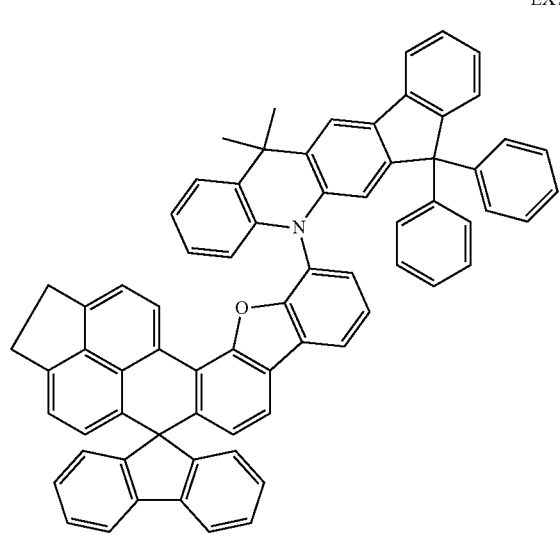
EX71
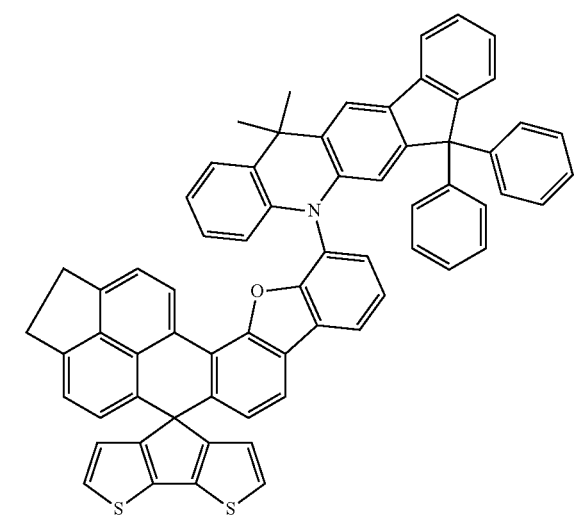
EX72
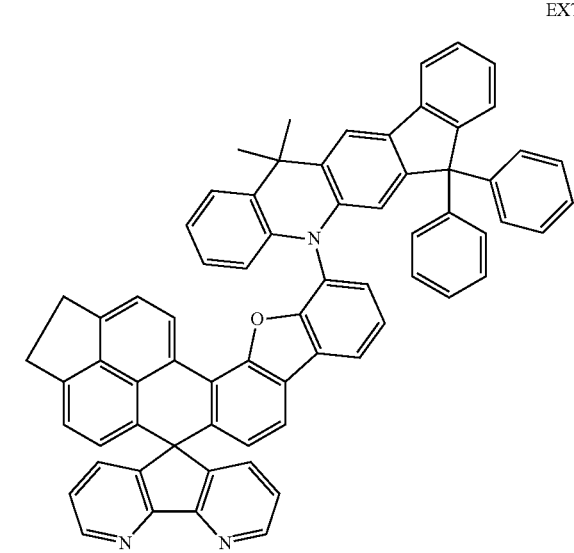
EX73
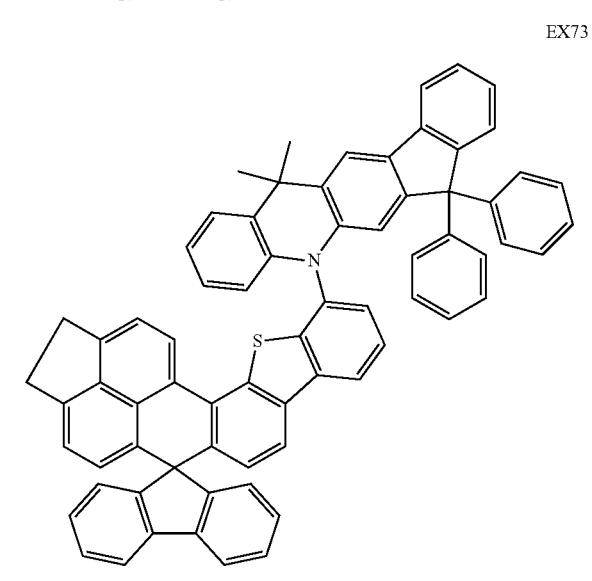

-continued
EX74
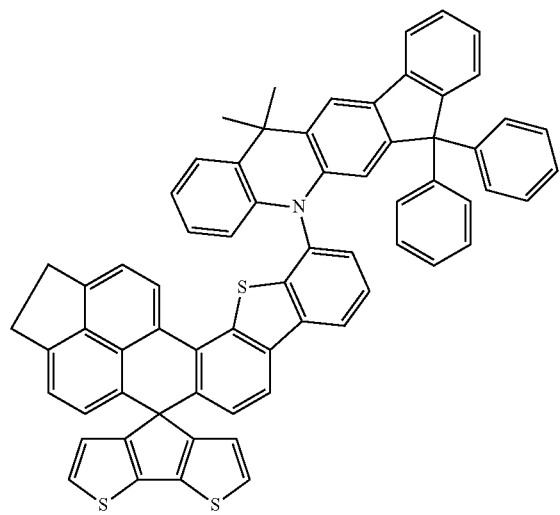
EX75
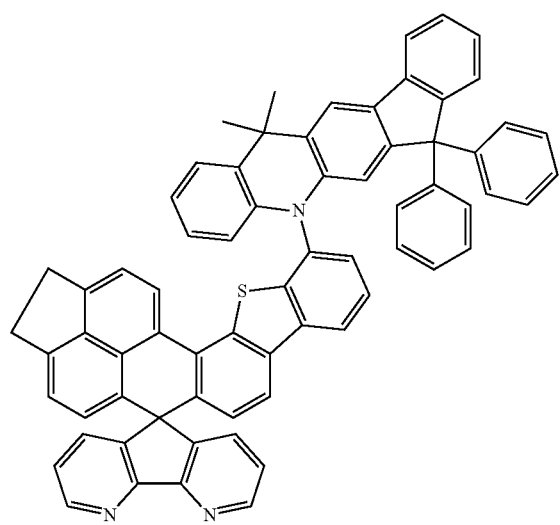
EX76
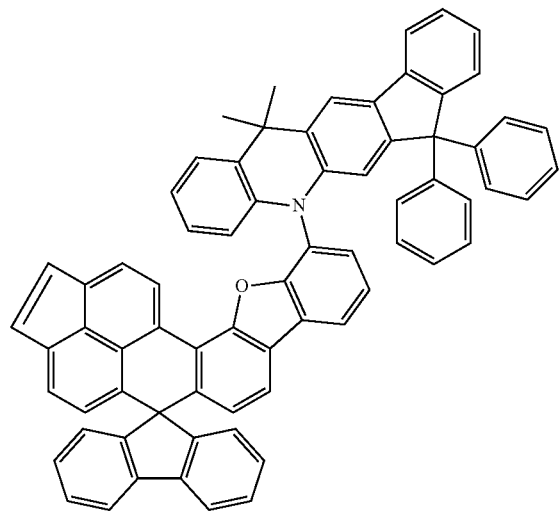
-continued
EX77
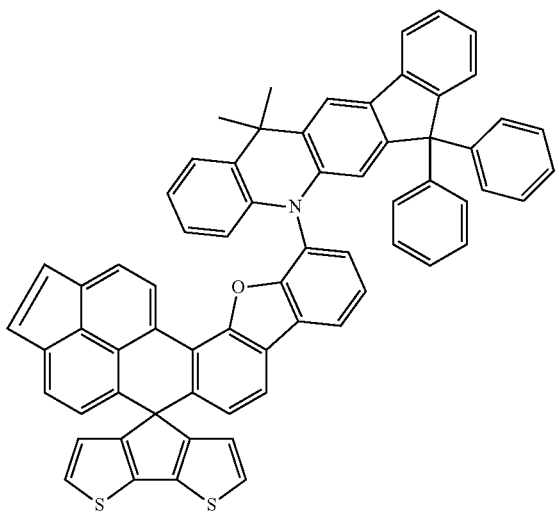
EX78
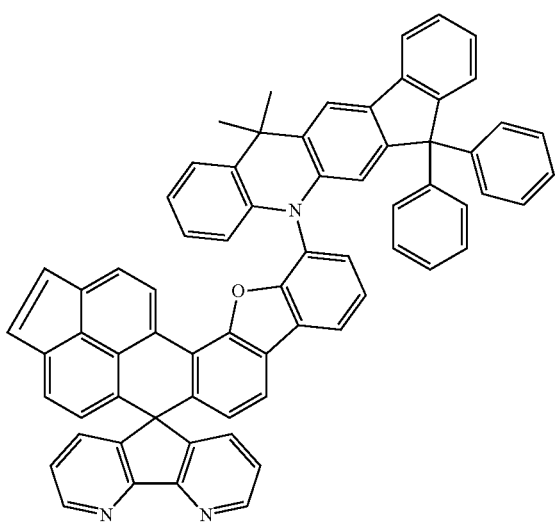
EX79
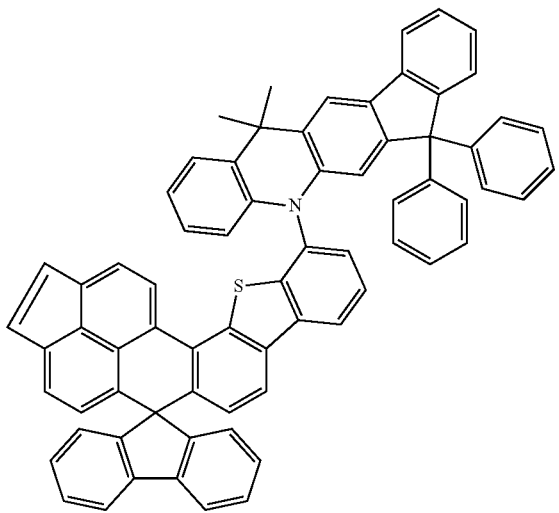

EX80
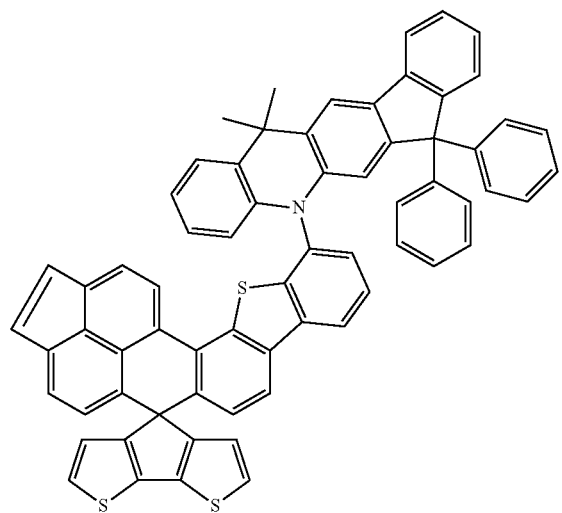
EX81
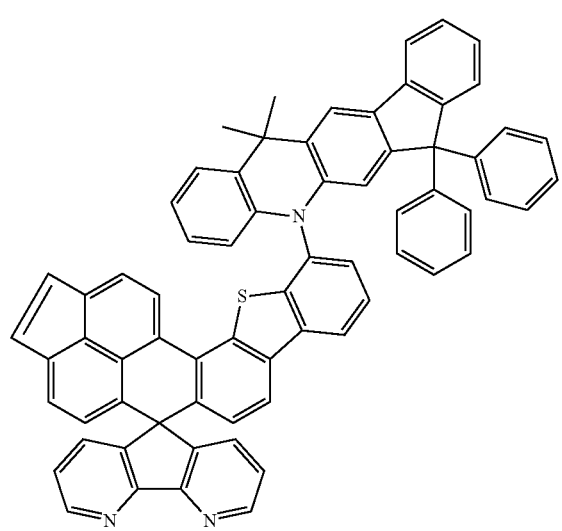
EX82
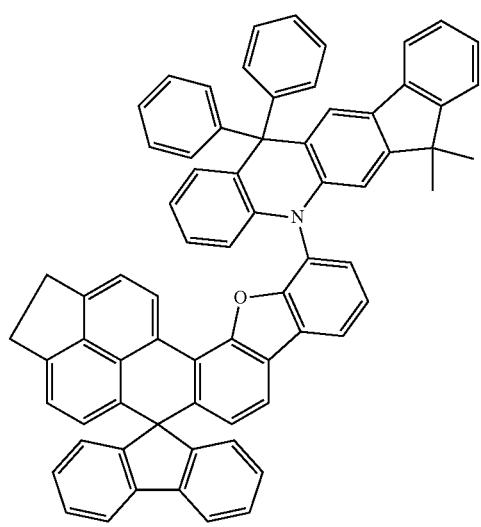
EX83
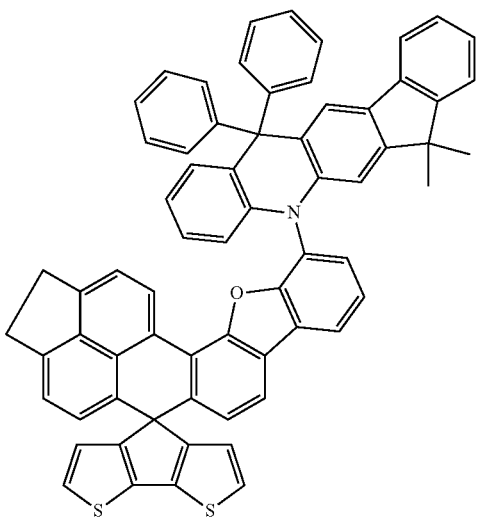
EX84
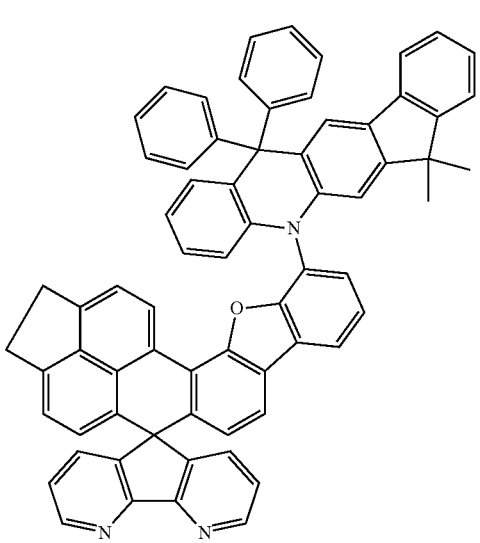
EX85
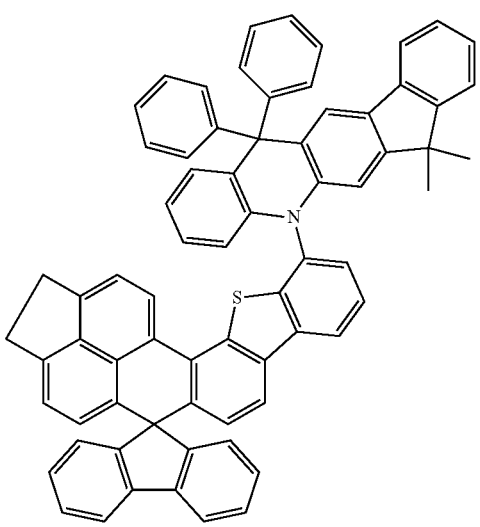

EX86
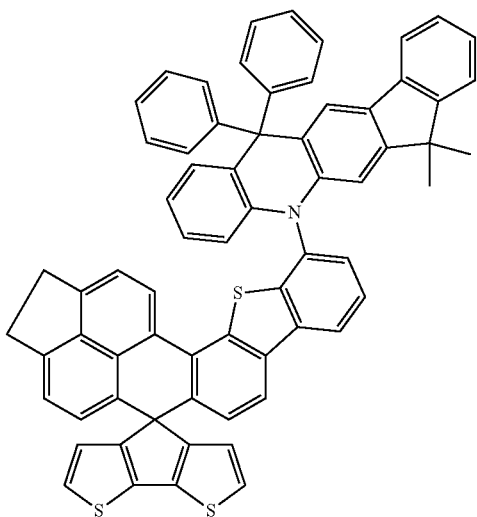
EX87
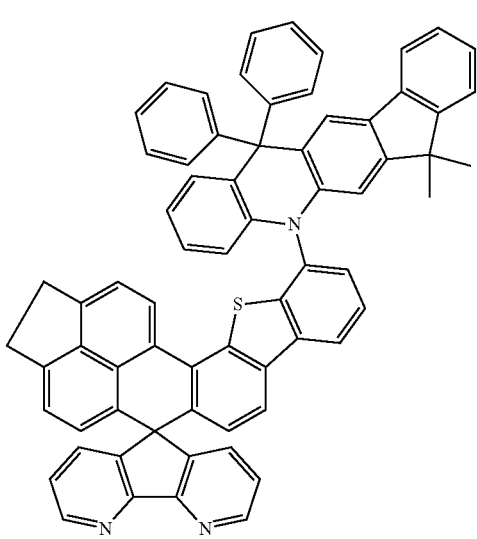
EX88
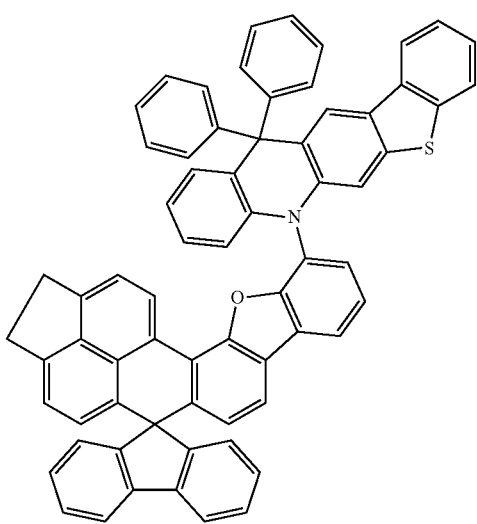
EX89
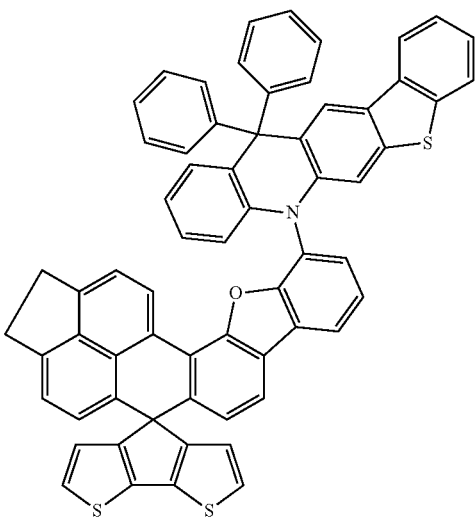
EX90
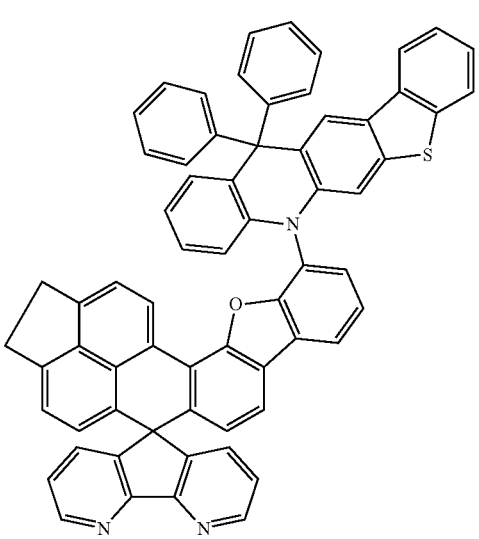
EX91
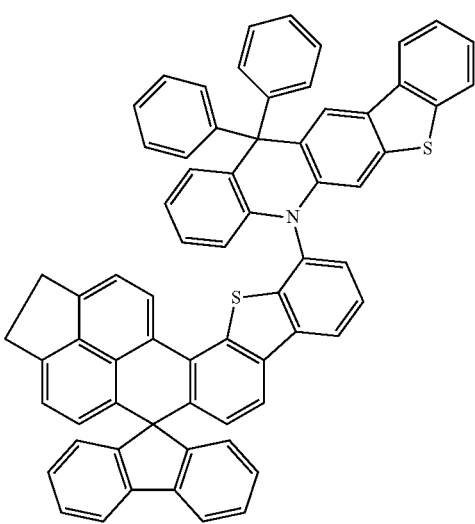

EX92
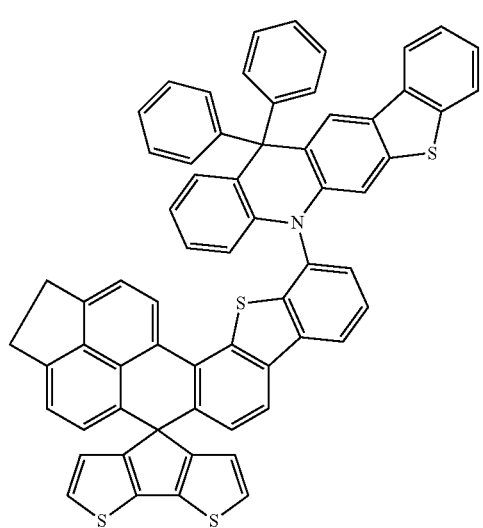
EX93
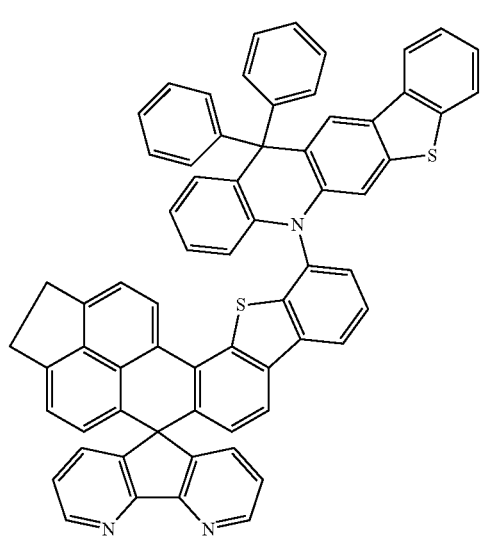
EX94
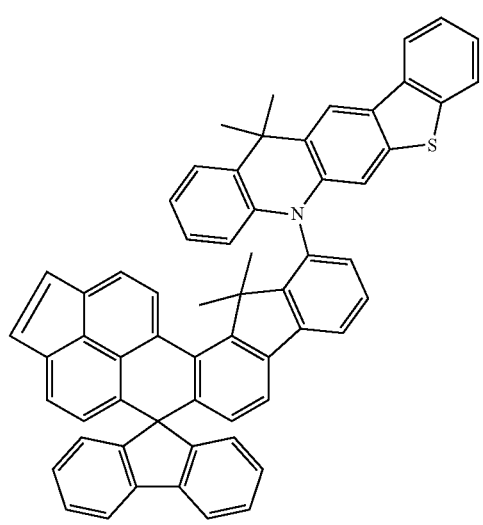
EX95
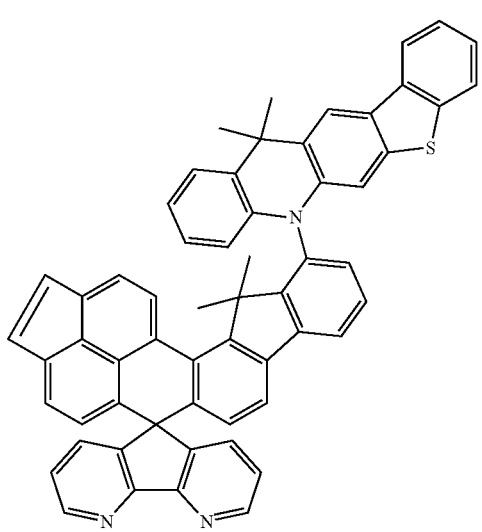
EX96
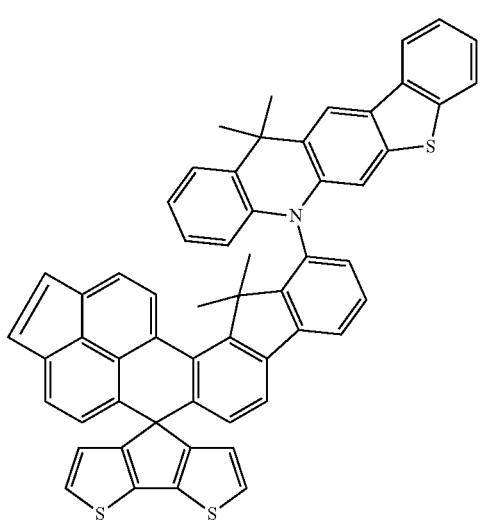
EX97
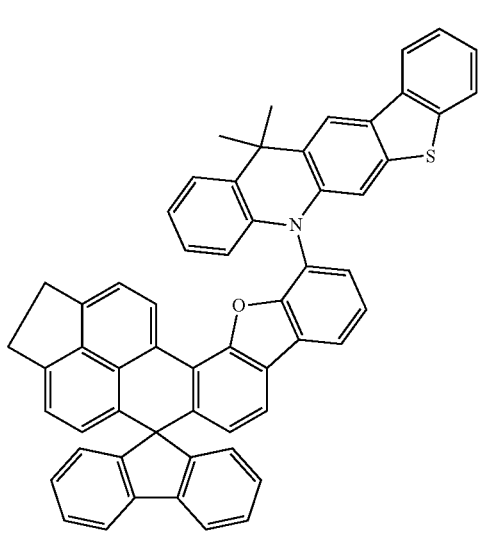

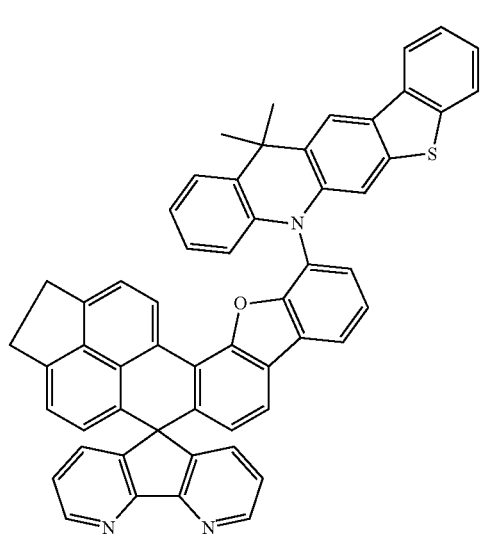
EX98
EX99
EX100
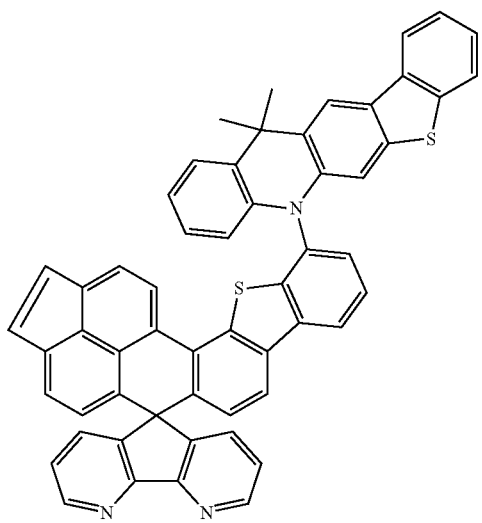
EX101
EX102
EX103

EX104

EX105

EX106

EX107

EX108

EX109

EX110
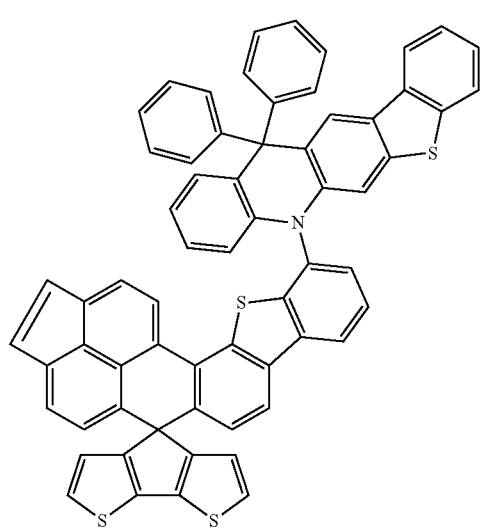
EX113
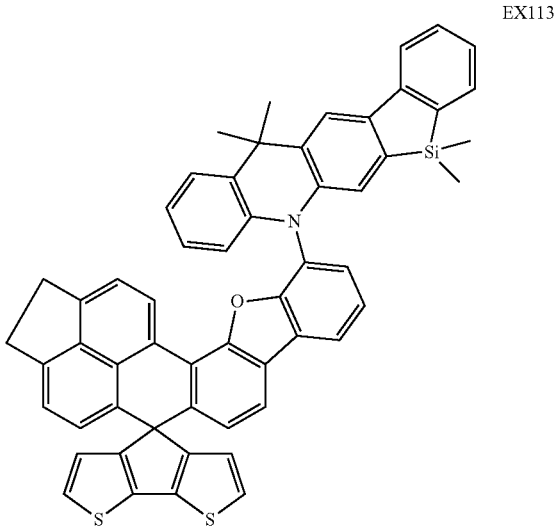
EX111
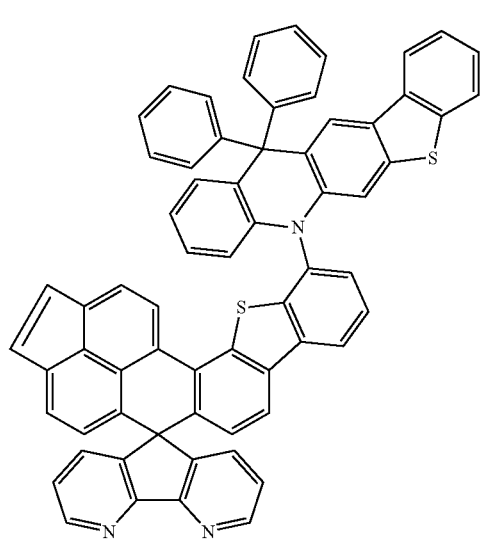
EX114
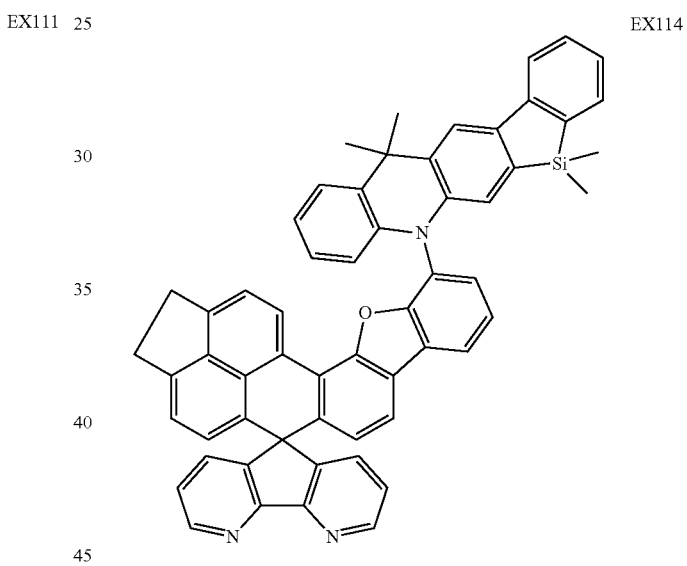
EX112
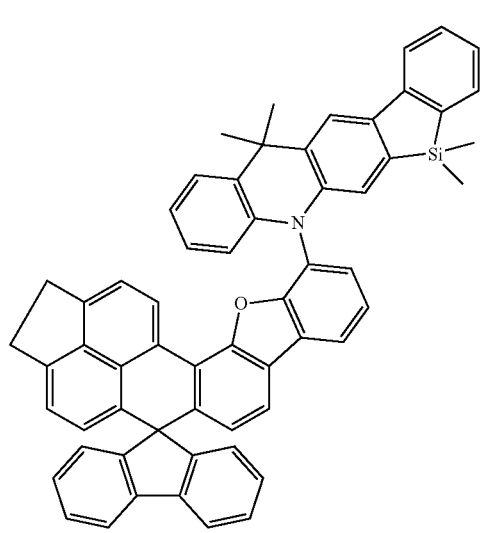
EX115
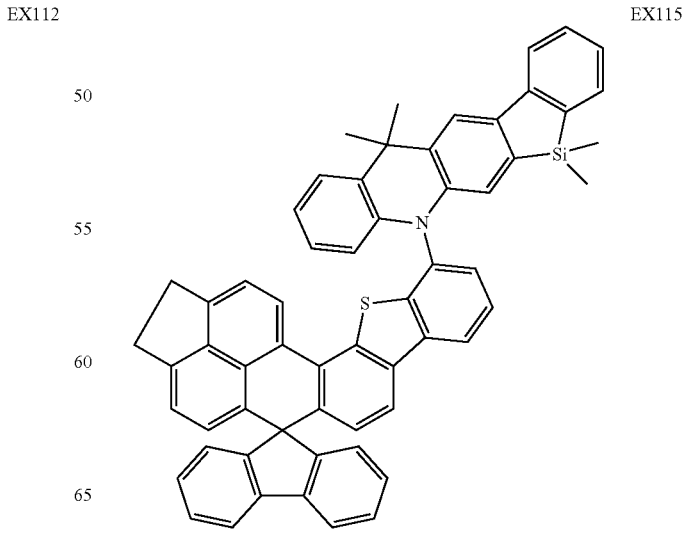

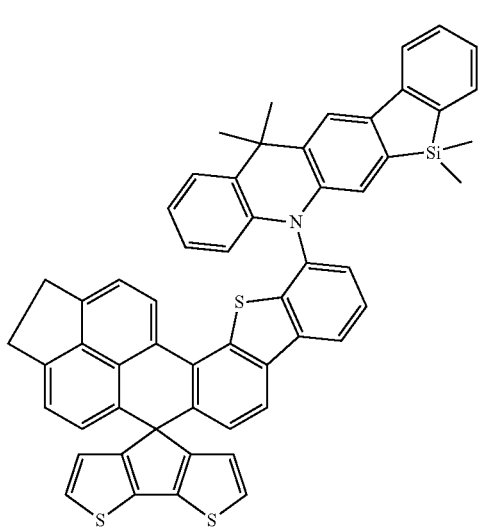
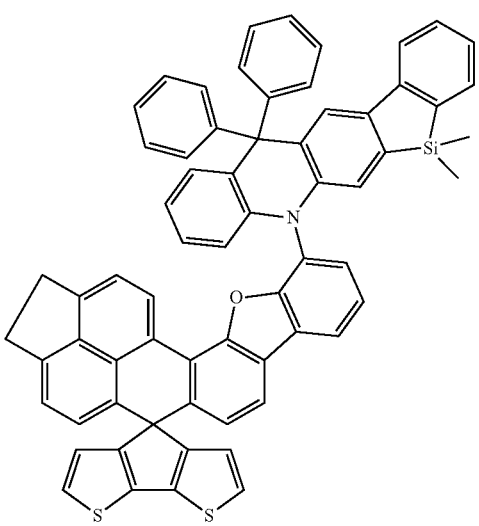

EX122
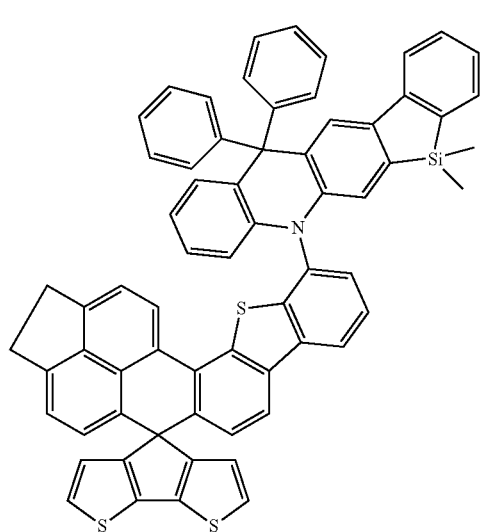
EX123
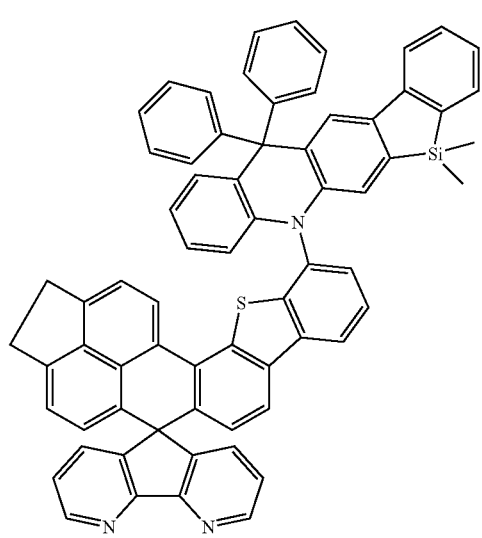
EX124
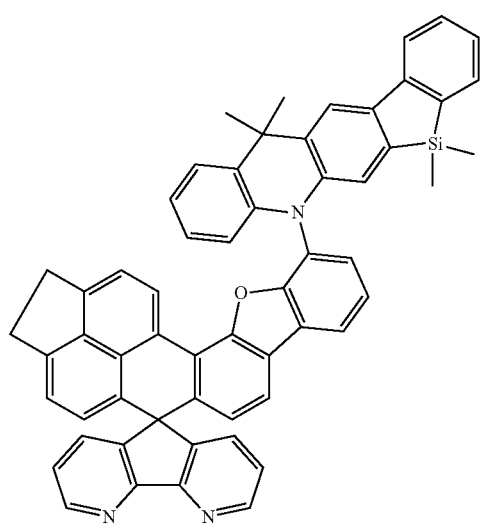
EX125
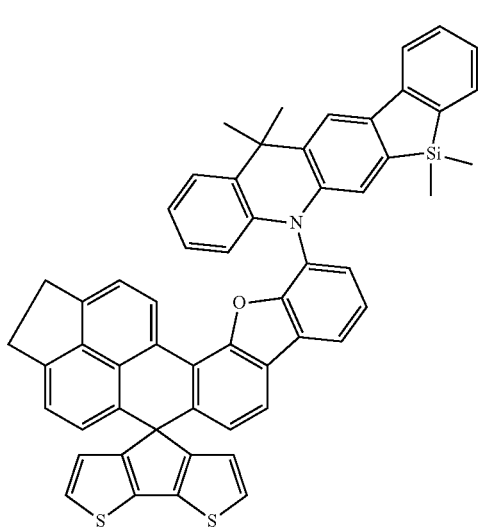
EX126
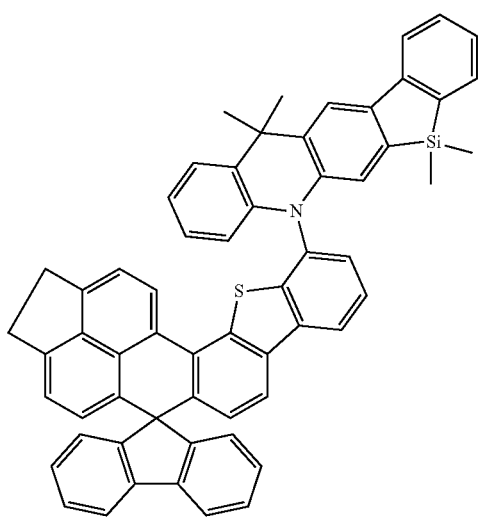
EX127
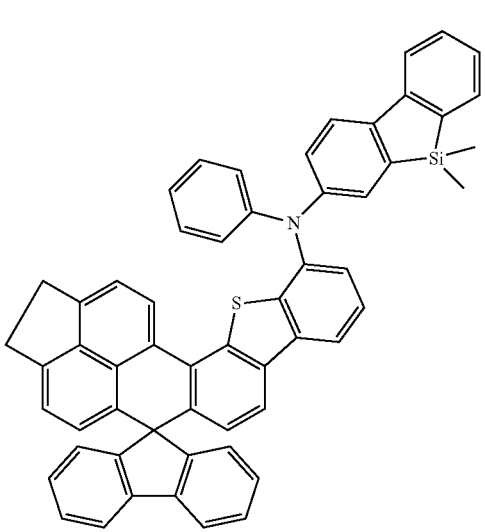

EX128
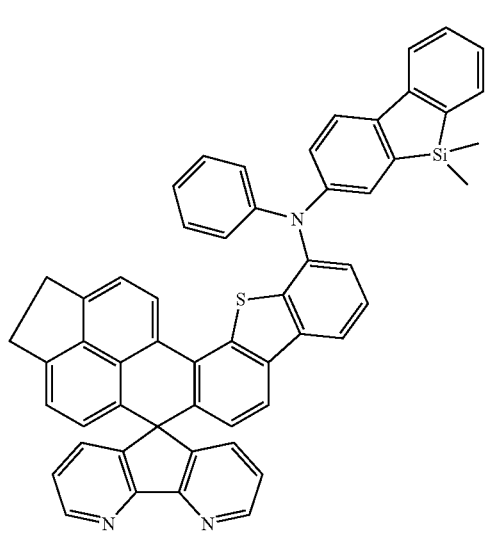
EX129
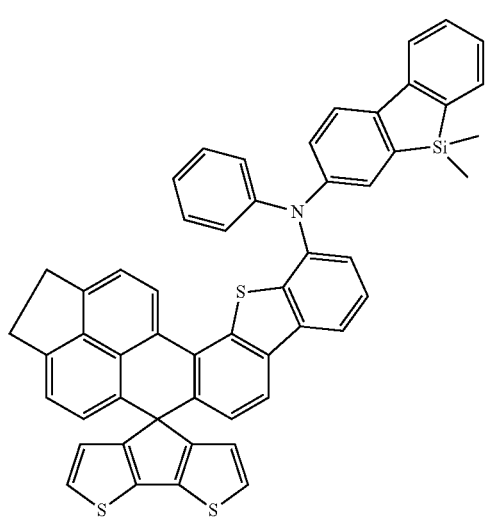
EX130
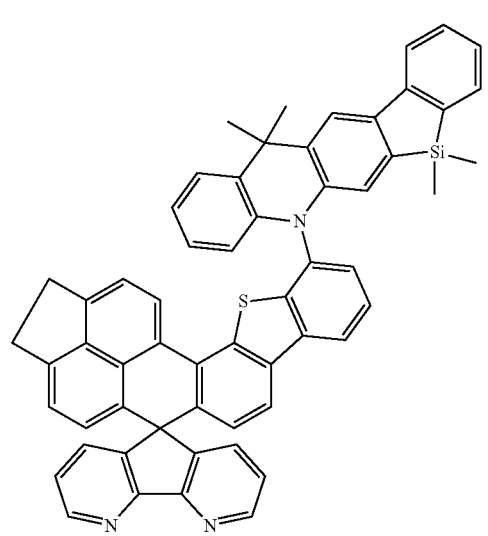
EX131
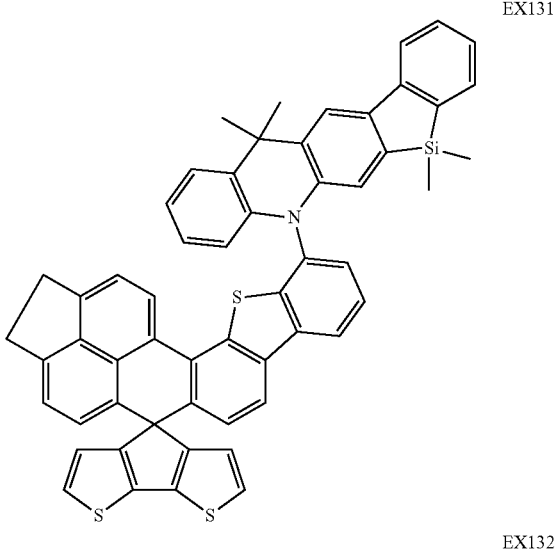
EX132
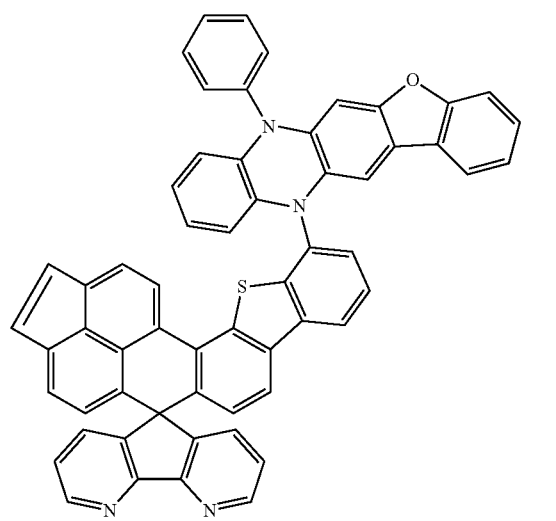
EX133
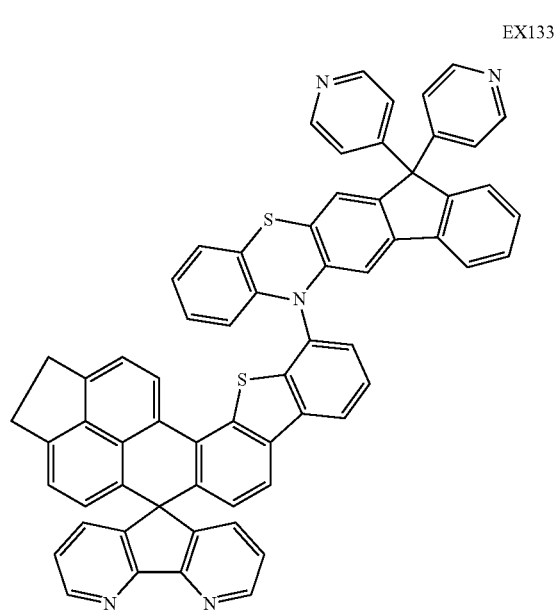

EX134
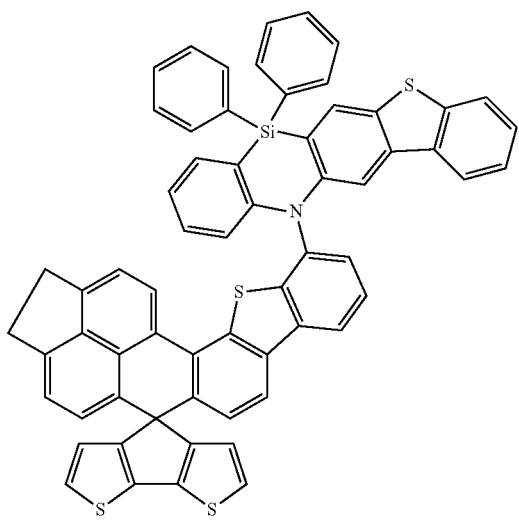
EX135
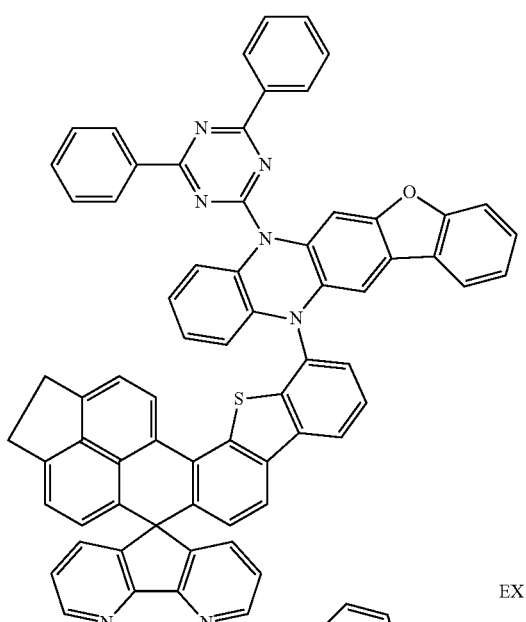
EX136
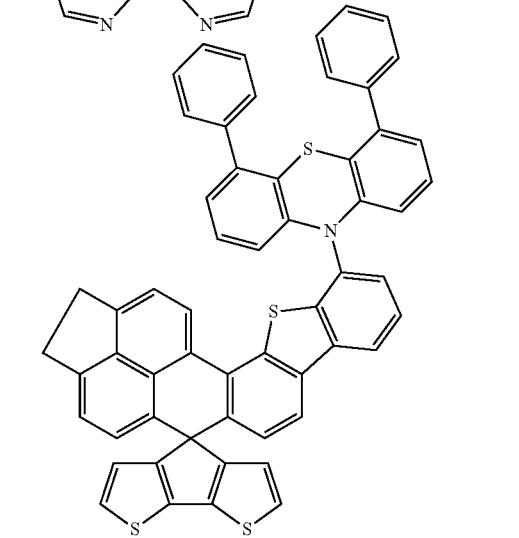
EX137
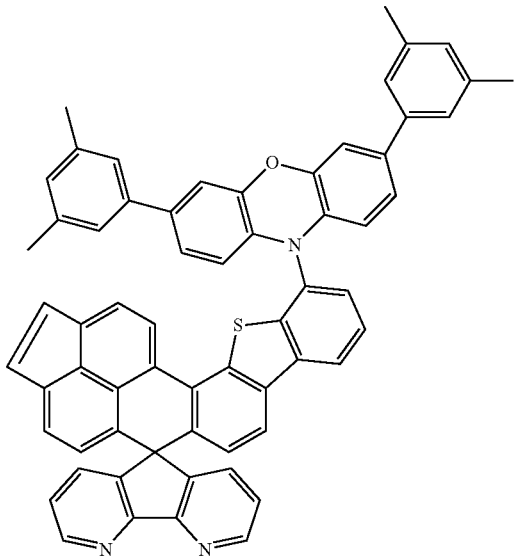
EX138
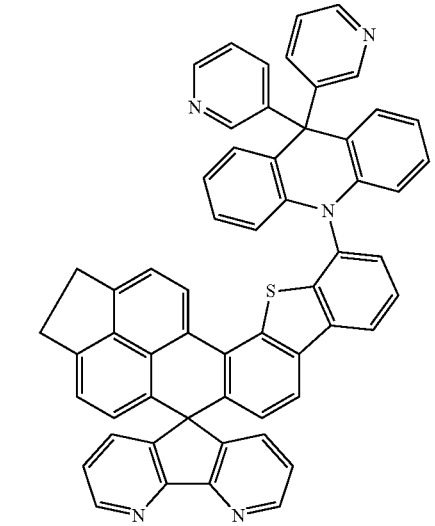
EX139
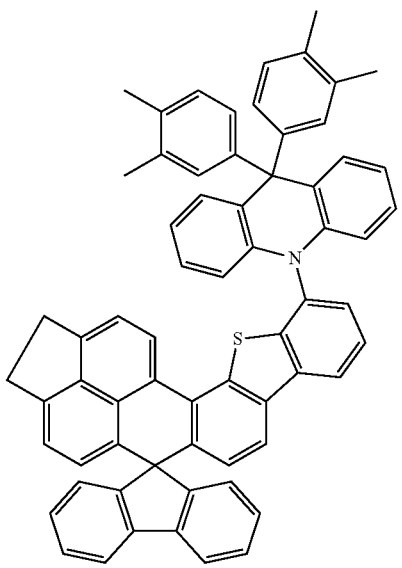

-continued
EX140
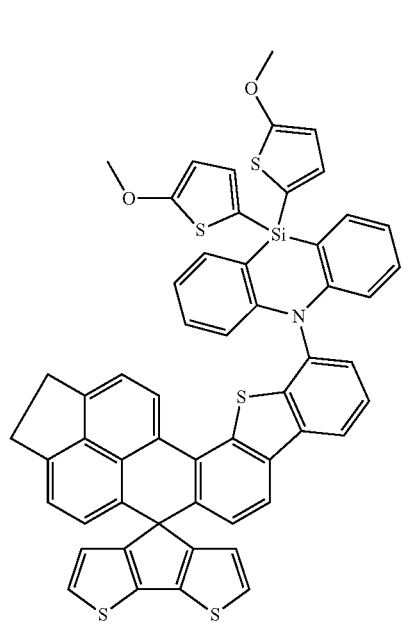
EX141
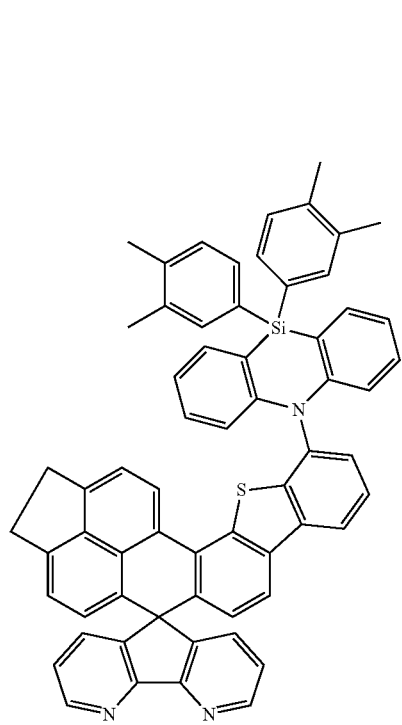
-continued
EX142
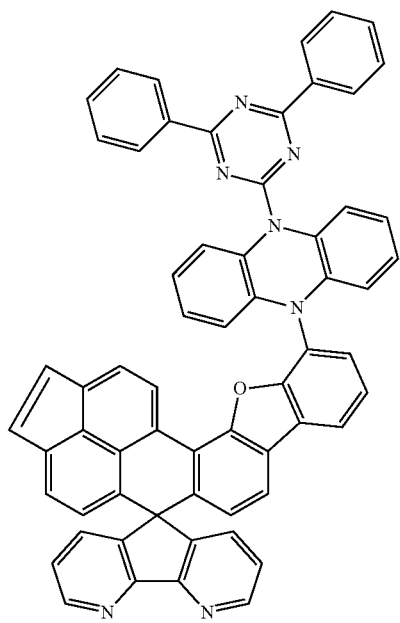
EX143
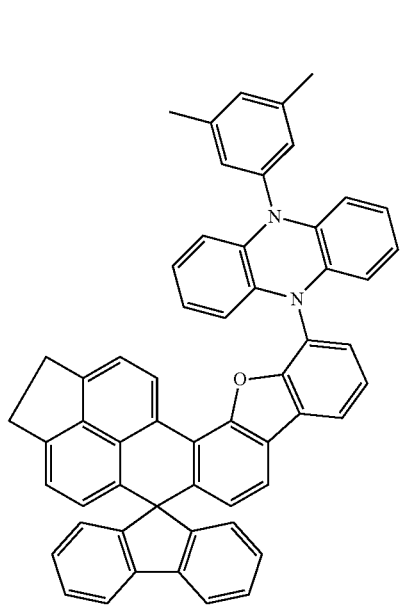

EX144
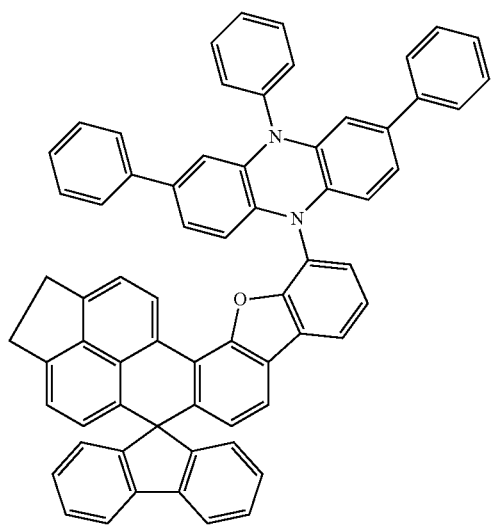
EX145
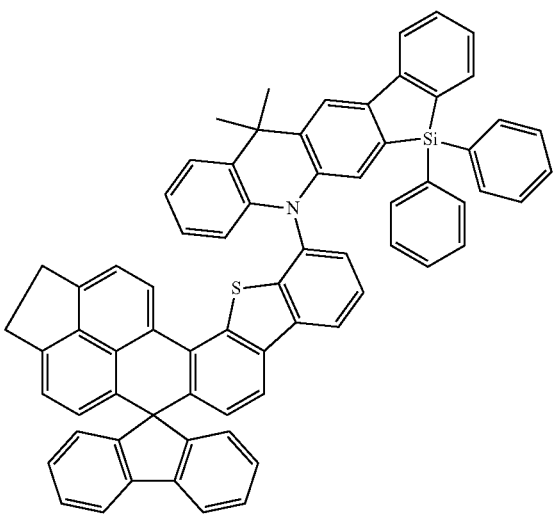
EX146
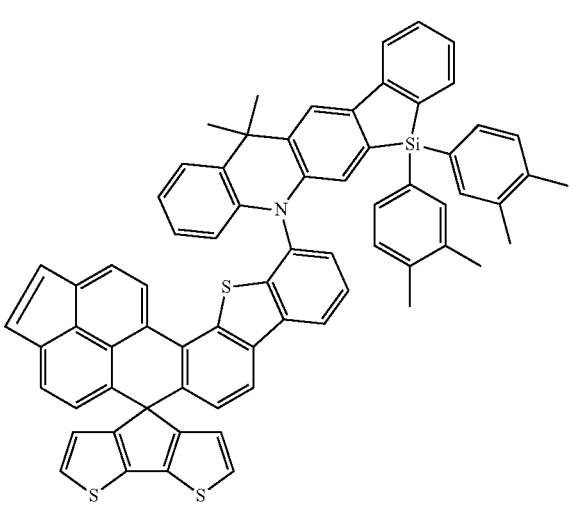
EX147
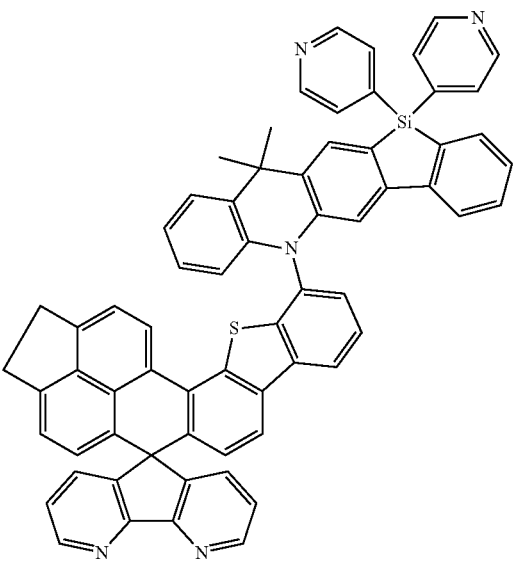
EX148
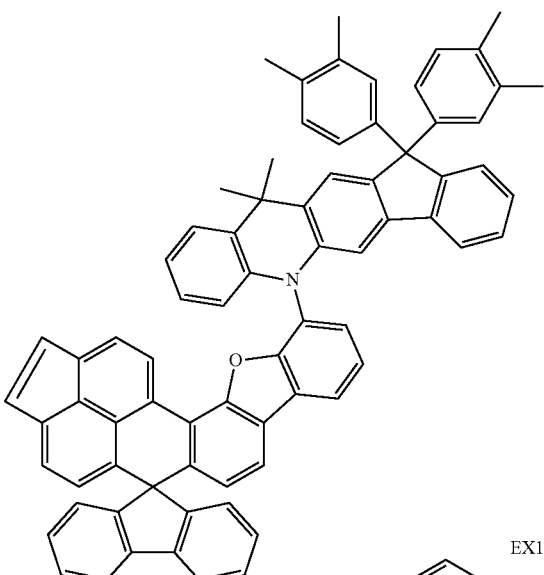
EX149
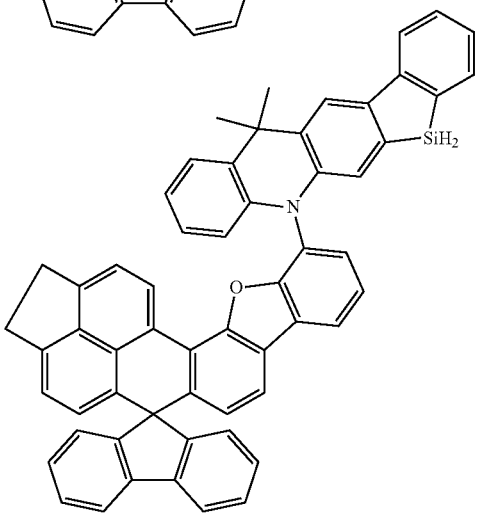

EX150
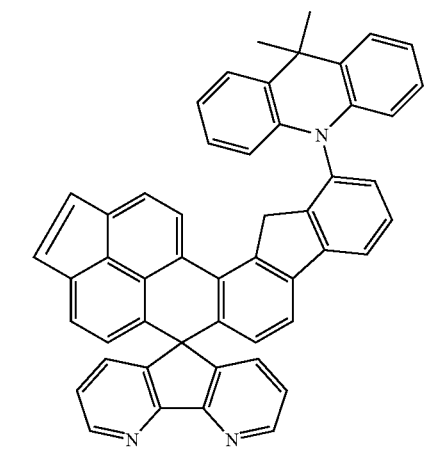
EX151
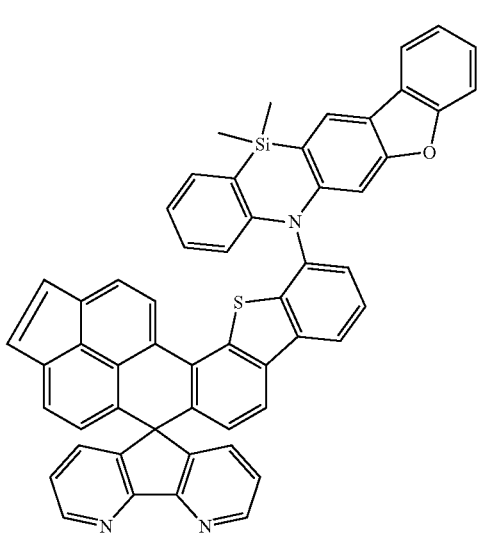
EX152
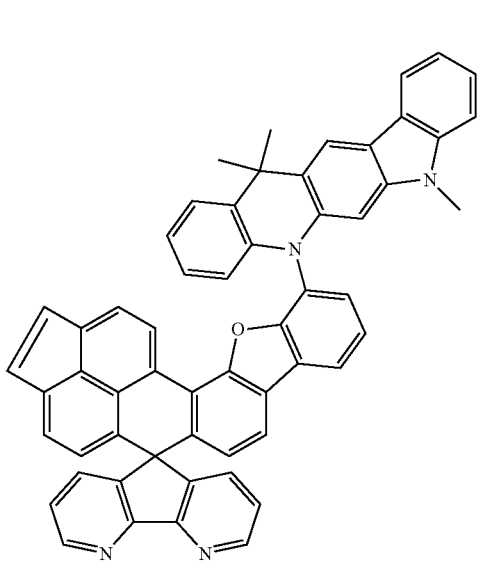
EX153
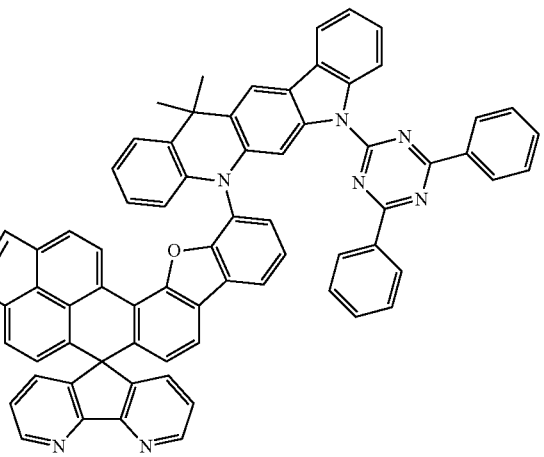
EX154
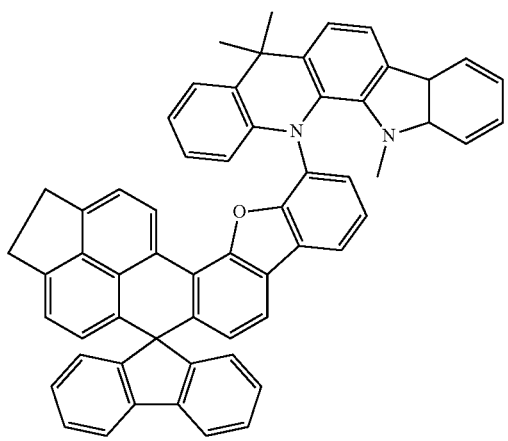
EX155
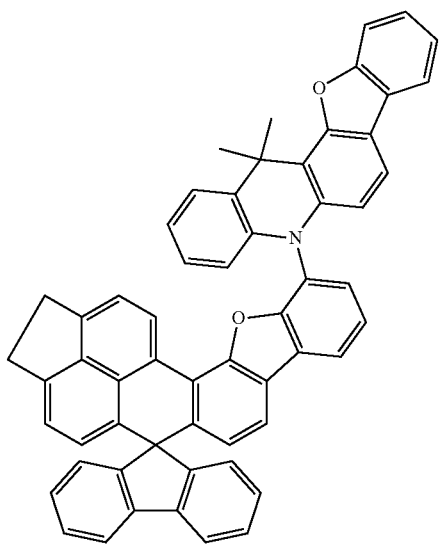

EX156
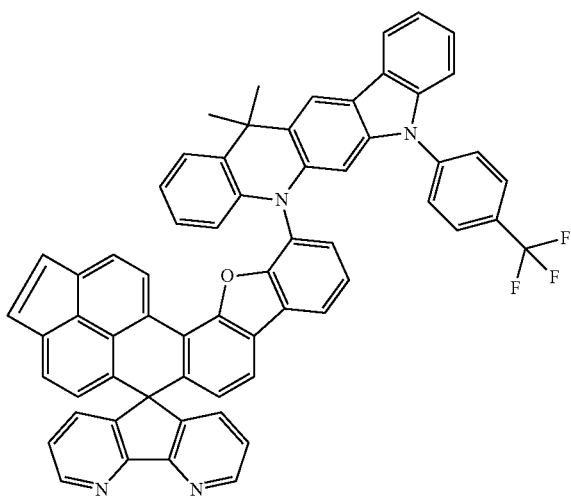
EX157
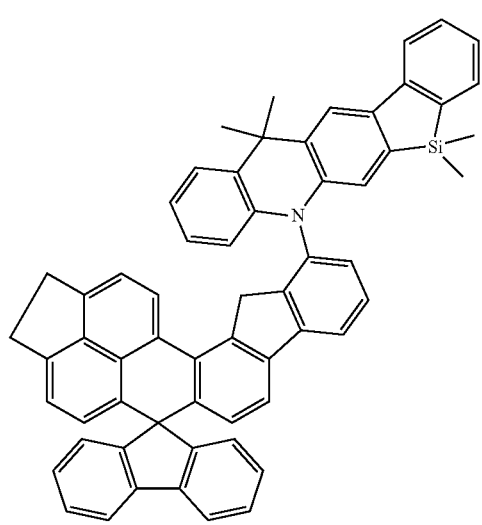
EX158
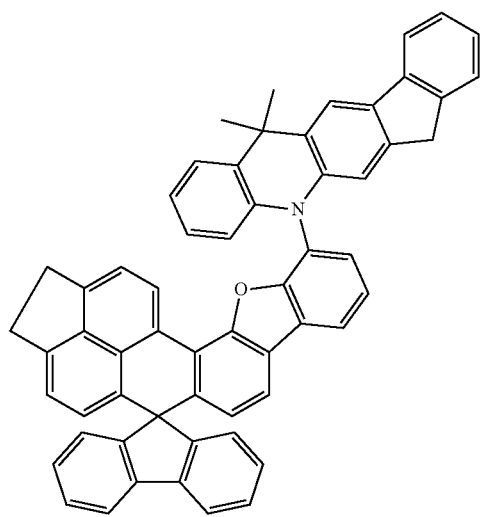
EX159
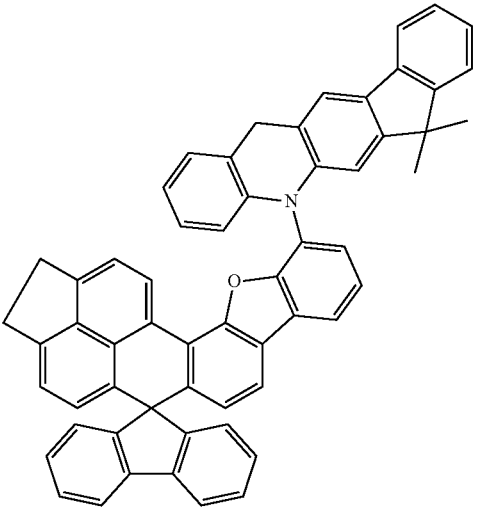
EX160
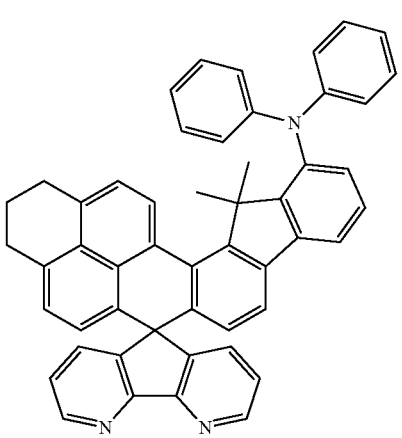
EX161
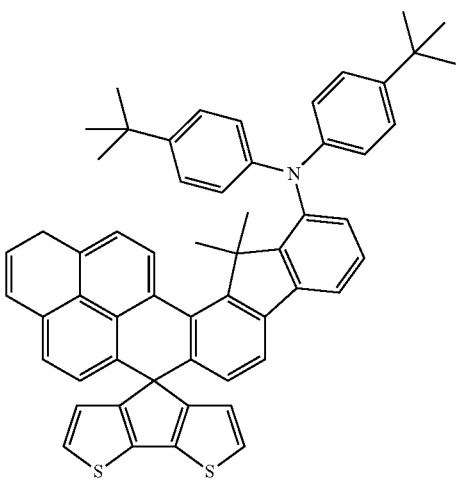

-continued

EX162

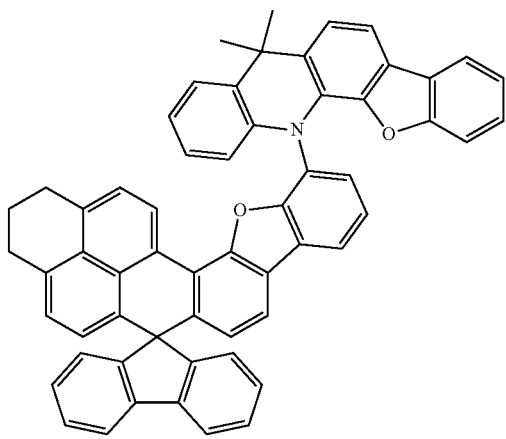

EX163

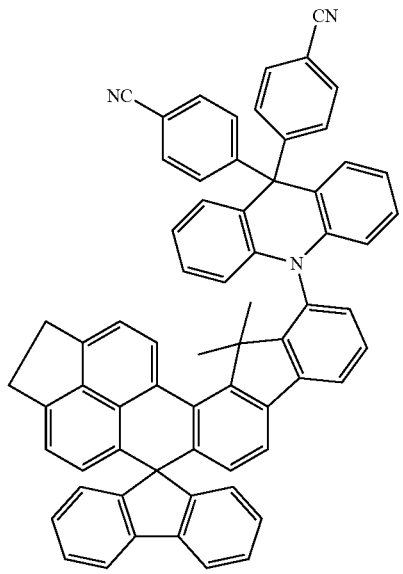

EX164

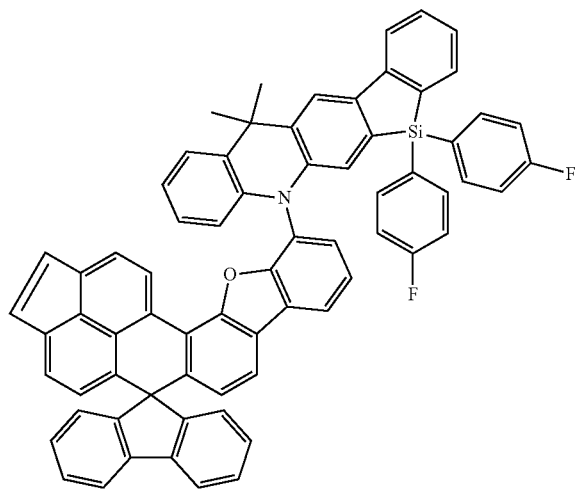

-continued

EX165

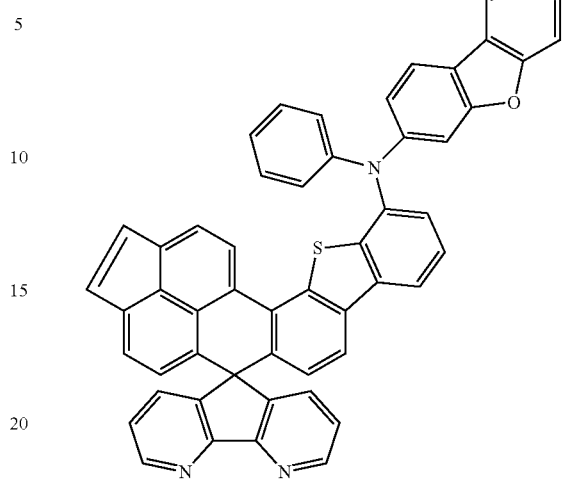

In another embodiment of the present invention, an organic electroluminescence device is disclosed. The organic electroluminescence device comprises a pair of electrodes composed of a cathode and an anode, and a light emitting layer between the pair of electrodes. The light emitting layer comprises the heteroaromatic compound of formula (1).

In some embodiments, the light emitting layer comprising the heteroaromatic compound of formula (1) is a fluorescent dopant material. In particular, the light emitting layer emits blue fluorescence.

In a further embodiment of the present invention, the organic electroluminescence device is a lighting panel. In other embodiment of the present invention, the organic electroluminescence device is a backlight panel.

Detailed preparation of the heteroaromatic compounds of the present invention will be clarified by exemplary embodiments below, but the present invention is not limited thereto. EXAMPLES 1 to 7 show the preparation of the heteroaromatic compounds of the present invention, and EXAMPLE 8 shows the fabrication and test reports of the organic EL devices.

Example 1

Synthesis of Intermediate A

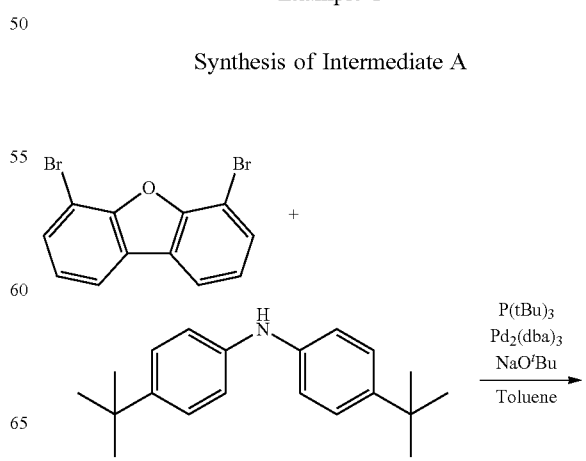

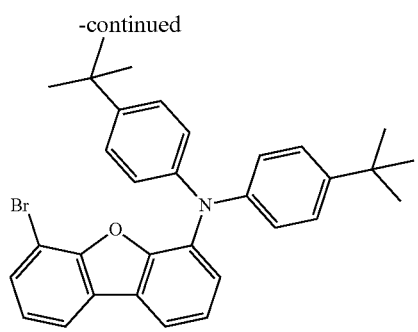

Intermediate A

A mixture of 13 g (40 mmol) of 4,6-dibromobenzofuran, 11.3 g (40 mmol) of bis(4-tert-butylphenyl)amine, 0.9 g (0.8 mmol) of Pd$_2$(dba)$_3$, 1.2 g (0.6 mmol) of tri-tert-butylphosphine, 5.0 g (52 mmol) of sodium tert-butoxide, and 150 ml of toluene was placed under nitrogen, and then heated and stirred at 70° C. for 24 hrs. After the reaction finished, the mixture was allowed to cool to room temperature. The solution was extracted with 100 ml of ethyl acetate and 300 ml of water. The organic layer was dried with anhydrous magnesium sulfate and the solvent was evaporated under reduced pressure. The residue was purified by column chromatography on silica to give product (16 g, 30.4 mmol, 76%).

Synthesis of Intermediate B

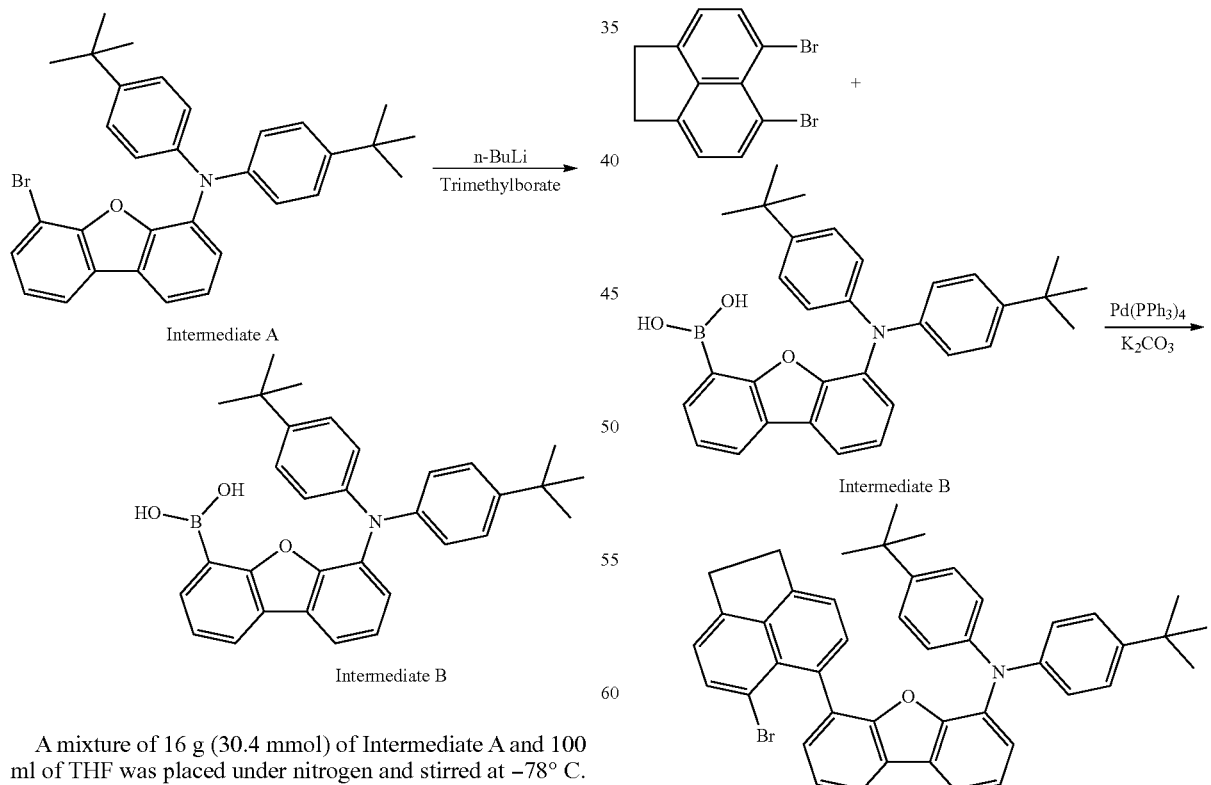

A mixture of 16 g (30.4 mmol) of Intermediate A and 100 ml of THF was placed under nitrogen and stirred at −78° C. After n-BuLi (2.5 M in hexane, 13.6 mL) was added dropwise, the temperature was raised to 0° C. and the mixture was stirred for 30 minutes. Afterwards, the temperature was lowered to −75° C. and 3.8 g (37 mmol) of trimethylborate was slowly added dropwise. Subsequently, the temperature was slowly raised to room temperature, and then the mixture was stirred for 3 hours. After the mixture had acidity by adding 3 N HCl, it was extracted with ethyl acetate and water. The organic layer was dried with anhydrous magnesium sulfate and the solvent was evaporated under reduced pressure. The residue was recrystallized from toluene to give product (11.2 g, 22.8 mmol, 75%).

Synthesis of
5,6-Dibromo-1,2-dihydroacenaphthylene

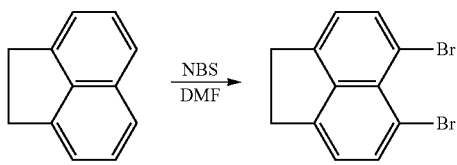

A mixture of 100 g (650 mmol) of Acenaphthene and 150 ml of DMF was placed under nitrogen and stirred at 0° C. After 250 g (1430 mmol) of N-bromosuccinimide in 500 ml of DMF was added dropwise, the temperature was raised to room temperature and the mixture was stirred for 18 hours. The precipitated product was filtered off with suction and washed with EtOH. The residue was recrystallized from EtOH to give product (46.5 g, 149.5 mmol, 23%).

Synthesis of Intermediate C

A mixture of 3.1 g (10 mmol) of 5,6-Dibromo-1,2-dihydro-acenaphthylene, 4.9 g (10 mmol) of Intermediate B, 0.58 g (0.5 mmol) of Pd(PPh$_3$)$_4$, 7 ml of 2M K$_2$CO$_3$, 40 ml of EtOH, and 40 ml of toluene was degassed and placed under nitrogen, and then heated at 90° C. overnight. After the reaction finished, the mixture was allowed to cool to room temperature. The organic phase was separated and washed with ethyl acetate and water. After being dried over magnesium sulfate, the solvent was removed in vacuo. The residue was purified by column chromatography on silica to give product (4.4 g, 6.5 mmol, 65%).

Synthesis of EX1

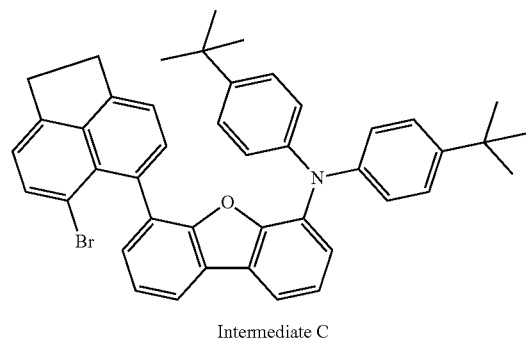

Intermediate C

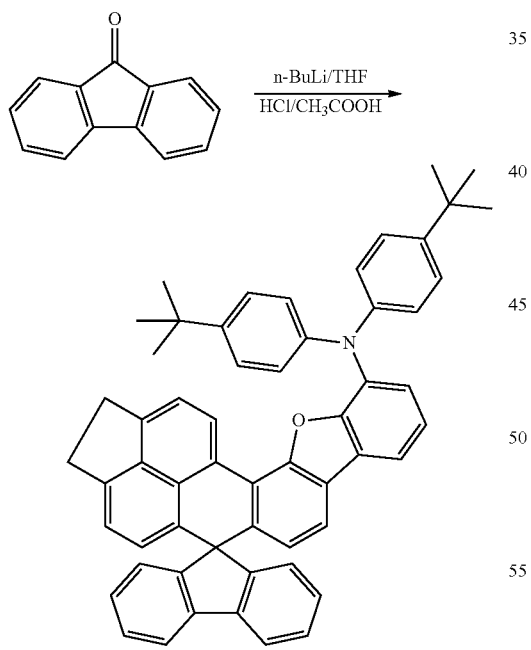

A mixture of 4.4 g (6.5 mmol) of Intermediate C and 70 ml of THF was placed under nitrogen and stirred at −78° C. After 3.4 mL of n-BuLi (2.5 M in hexane) was added dropwise, the mixture was stirred for 1 hour. Afterwards, 1.17 g (6.5 mmol) of 9H-fluoren-9-one dissolved in 15 ml of THF was slowly added dropwise, the temperature was slowly raised to room temperature, and the mixture was stirred for 12 hours. The reaction was finished by adding 70 ml of saturated NaHCO$_3$ aqueous solution, and the mixture was extracted with DCM and water to receive the organic layer. The organic layer was dried over magnesium sulfate, and the solvent was removed in vacuo. The residue was dissolved in 30 ml acetic acid, and then a small amount of 3 N HCl was added thereto. After being stirred at 100° C. for 12 hours, the solution was cooled down to room temperature and then filtered. The filtrate was purified by column chromatography on silica to give product (2.6 g, 3.4 mmol, 52%). MS(m/z, EI$^+$): 760.3.

Example 2

Synthesis of EX6

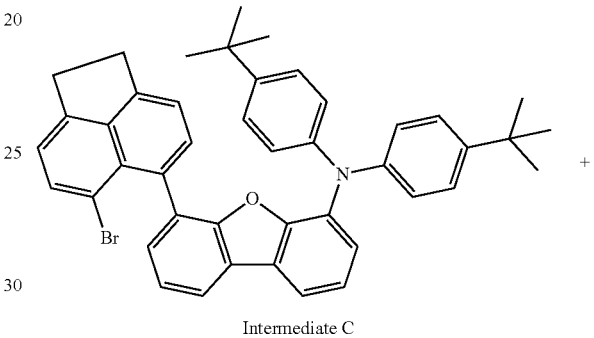

Intermediate C

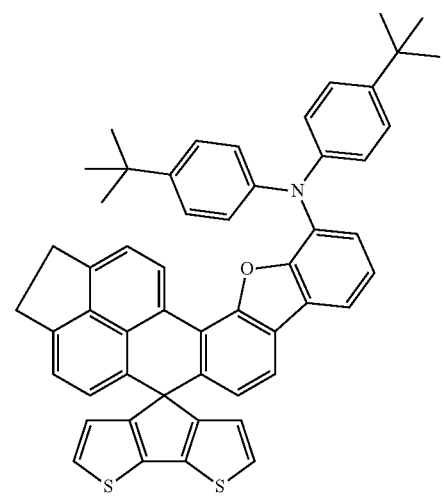

The same synthesis procedure as in Synthesis of EX1 was used, except that 0.77 g (4.0 mmol) of Cyclopentadithiophene Ketone was used instead of 9H-fluoren-9-one to obtain 1.2 g (40%) of EX6. MS(m/z, EI$^+$): 772.2.

Example 3

Synthesis of methyl 2-((9,9-dimethyl-9H-fluoren-2-yl)amino)-benzoate

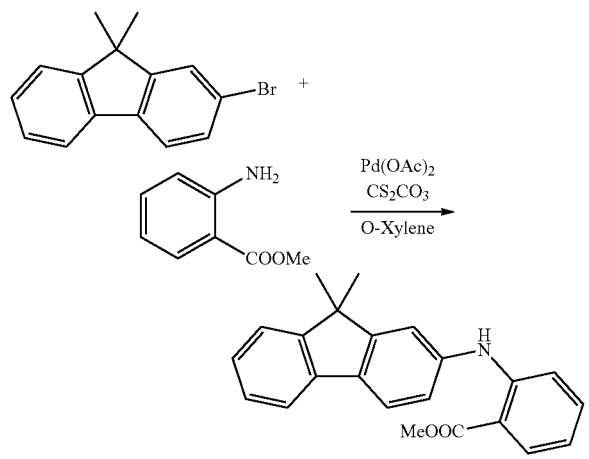

A mixture of 10 g (36.6 mmol) of 2-bromo-9,9-dimethyl-9H-fluorene, 6.64 g (43.9 mmol) of methyl 2-aminobenzoate, 0.3 g (1.46 mmol) of Pd(OAc)$_2$, 17.9 g (54.9 mmol) of cesium carbonate, and 120 ml of o-xylene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 10 g of methyl 2-((9,9-dimethyl-9H-fluoren-2-yl)amino)benzoate as yellow oil (79.6%), $^1$H NMR (CDCl$_3$, 400 MHz): chemical shift (ppm) 8.97 (s, 1H), 8.11 (d, 1H), 7.87 (d, 1H), 7.75-7.64 (m, 3H), 7.41-7.29 (m, 3H), 7.08 (m, 1H), 6.92 (d, 1H), 6.77 (d, 1H), 3.79 (s, 3H), 1.57 (s, 3H), 1.54 (s, 3H).

Synthesis of 2-(2-((9,9-dimethyl-9H-fluoren-2-yl)amino)phenyl)-propan-2-ol

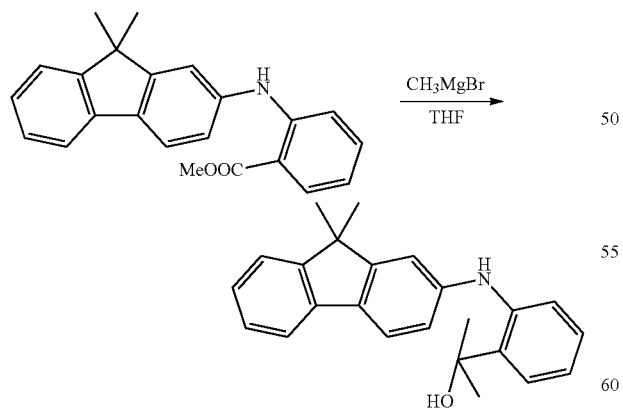

The compound methyl 2-((9,9-dimethyl-9H-fluoren-2-yl)amino)-benzoate (10 g, 29.1 mmol) was mixed with 100 ml of THF. To the mixture, 58 ml of 3 M methylmagnesium bromide was added slowly at room temperature and then stirred at room temperature for 3 hrs. After the reaction finished, ammonium chloride solution was added to the reaction mixture, which was then extracted with ethyl acetate/water to receive the organic layer. The solvent was removed under reduced pressure, and the crude product was purified by column chromatography, yielding 9 g of 2-(2-((9,9-dimethyl-9H-fluoren-2-yl)amino)phenyl)-propan-2-ol as yellow oil (90%), $^1$H NMR (CDCl$_3$, 400 MHz): chemical shift (ppm) 8.91 (s, 1H), 7.81 (d, 1H), 7.59 (d, 1H), 7.54 (d, 1H), 7.35-7.39 (m, 3H), 7.29 (m, 1H), 6.92 (m, 1H), 6.76-6.74 (d, 2H), 6.58 (d, 1H), 3.88 (s, 1H), 1.53 (s, 3H), 1.51 (s, 3H), 1.35 (s, 6H).

Synthesis of 7,7,13,13-tetramethyl-7,13-dihydro-5H-indeno-[1,2-b]-acridine

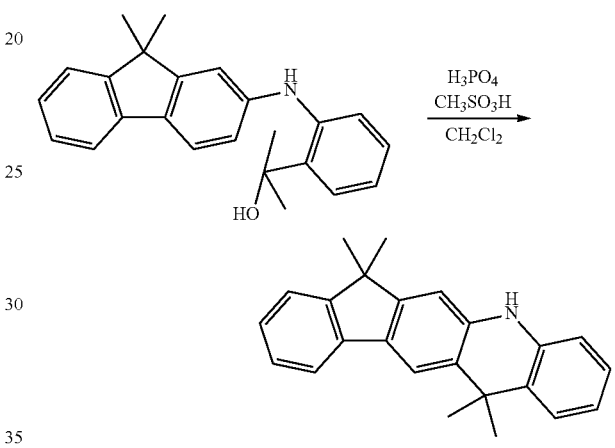

The compound 2-(2-((9,9-dimethyl-9H-fluoren-2-yl)amino)-phenyl)-propan-2-ol (27 g, 78.6 mmol) was mixed with 400 ml of CH$_2$Cl$_2$. To the mixture, 51 ml of methane sulfonic acid and 37 ml of phosphoric acid was added slowly at room temperature and then stirred at room temperature for 12 hrs. After the reaction finished, ice-cold water was added to the reaction mixture, and then 20% sodium hydroxide solution was added thereto. The reaction mixture was extracted with ethyl acetate/water to receive the organic layer. The solvent was removed under reduced pressure, and the crude product was purified by column chromatography, yielding 15 g of 7,7,13,13-tetramethyl-7,13-dihydro-5H-indeno-[1,2-b]-acridine as yellow solid (58.8%). $^1$H NMR (CDCl$_3$, 400 MHz): chemical shift (ppm) 8.95 (s, 1H), 7.79 (s, 1H), 7.72 (d, 1H), 7.43 (d, 1H), 7.36 (d, 1H), 7.25 (m, 1H), 7.16 (dd, 1H), 7.04 (m, 1H), 6.87 (s, 1H), 6.81-6.78 (m, 2H) 1.55 (s, 6H), 1.38 (s, 6H).

Synthesis of Intermediate D

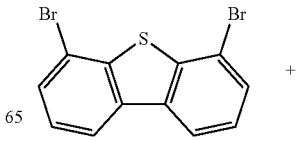

Synthesis of Intermediate F

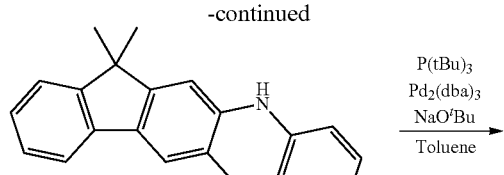

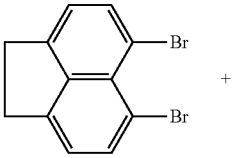

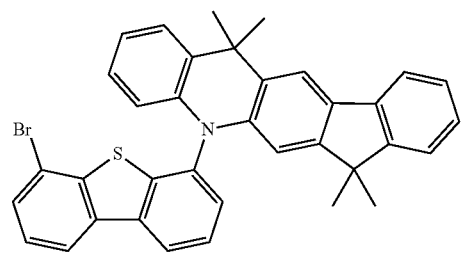

Intermediate D

The same synthesis procedure as in Synthesis of Intermediate A was used, except that 4,6-dibromobenzothiophene (6.8 g, 20 mmol) was used instead of 4,6-dibromobenzofuran and 7,7,13,13-tetramethyl-7,13-dihydro-5H-indeno-[1,2-b]acridine (6.5 g, 20 mmol) was used instead of bis(4-tert-butylphenyl)amine to obtain 8.3 g (71%) of Intermediate D.

Synthesis of Intermediate E

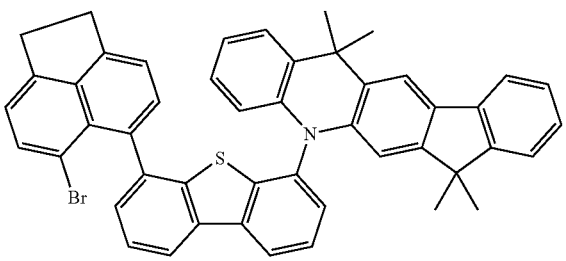

Intermediate E

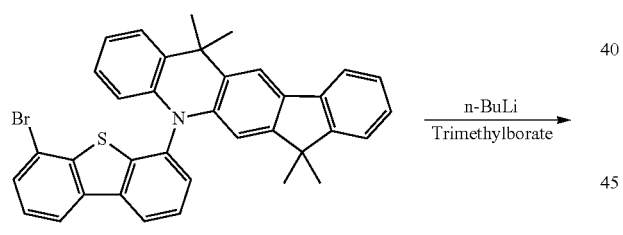

Intermediate F

The same synthesis procedure as in Synthesis of Intermediate C was used, except that Intermediate E (5.7 g, 10.3 mmol) was used instead of Intermediate B to obtain 4.6 g (61%) of Intermediate F.

Synthesis of EX9

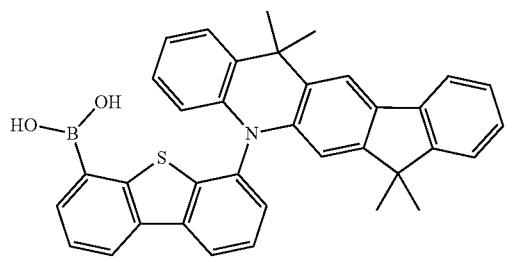

Intermediate E

The same synthesis procedure as in Synthesis of Intermediate B was used, except that Intermediate D (8.3 g, 14.2 mmol) was used instead of Intermediate A to obtain 5.7 g (73%) of Intermediate E.

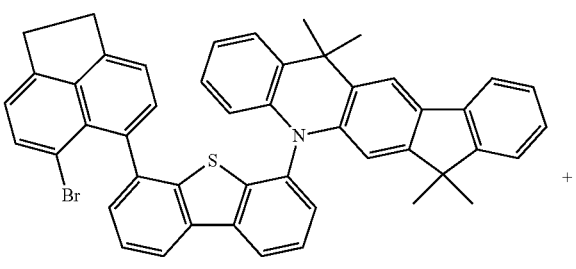

Intermediate F

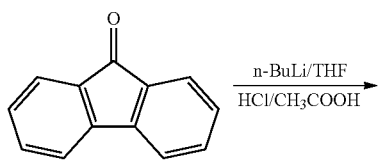

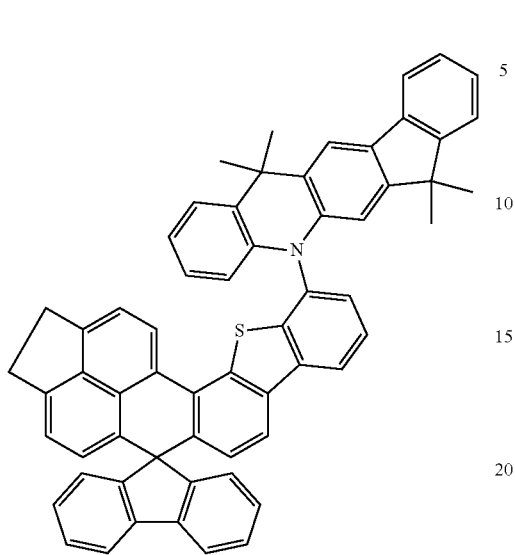

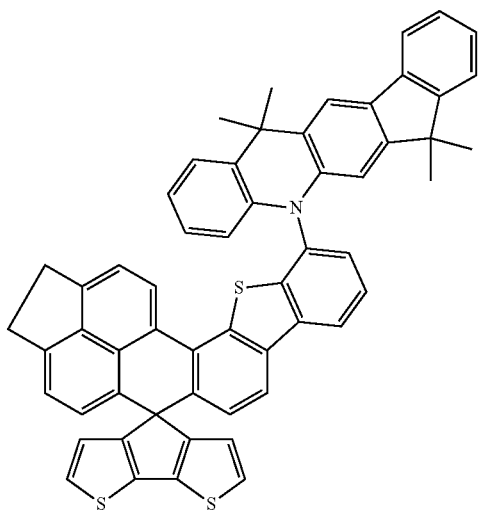

The same synthesis procedure as in Synthesis of EX6 was used, except that Intermediate F (3.6 g, 4.8 mmol) was used instead of Intermediate C to obtain 2.5 g (48%) of EX10. MS(m/z, EI⁺): 832.3.

The same synthesis procedure as in Synthesis of EX1 was used, except that Intermediate F (3.6 g, 4.8 mmol) was used instead of Intermediate C to obtain 2.0 g (51%) of EX9. MS(m/z, EI⁺): 820.4.

Example 5

Synthesis of methyl 2-(dibenzo[b,d]thiophen-3-ylamino)benzoate

Example 4

Synthesis of EX10

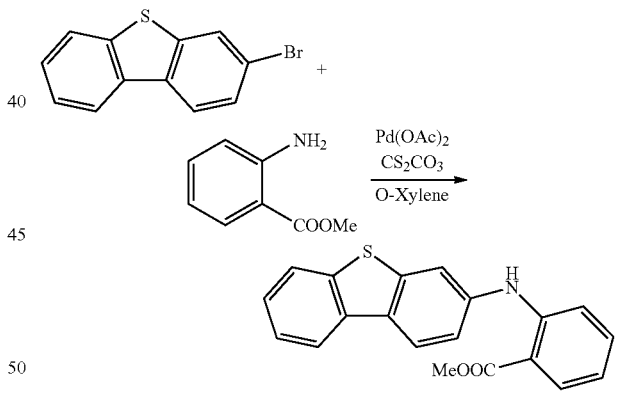

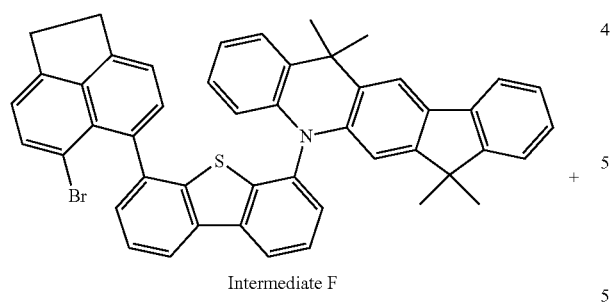

Intermediate F

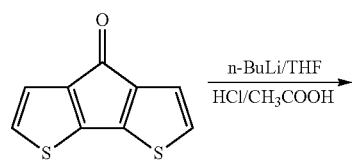

A mixture of 5 g (19 mmol) of 3-bromodibenzo[b,d]thiophene, 3.45 g (22.8 mmol) of methyl 2-aminobenzoate, 0.17 g (0.76 mmol) of Pd(OAc)$_2$, 9.28 g (28.5 mmol) of cesium carbonate, and 60 ml of o-xylene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 4.8 g of methyl 2-(dibenzo[b,d]thiophen-3-ylamino)benzoate as yellow oil (75.8%), $^1$H NMR (CDCl$_3$, 400 MHz): chemical shift (ppm) 8.99 (s, 1H), 8.14 (d, 1H), 7.89 (d, 1H), 7.79-7.68 (m, 3H), 7.45-7.33 (m, 3H), 7.12 (m, 1H), 6.97 (d, 1H), 6.81 (d, 1H), 3.79 (s, 3H).

Synthesis of 2-(2-(dibenzo[b,d]thiophen-3-ylamino)phenyl)propan-2-ol

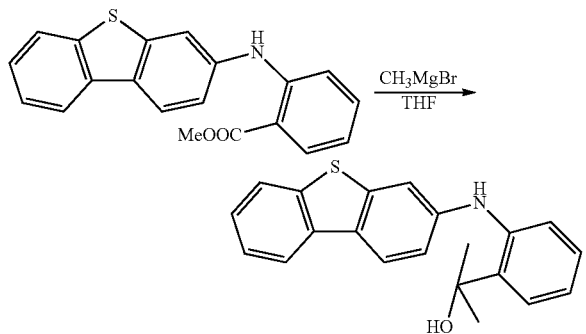

The compound methyl 2-(dibenzo[b,d]thiophen-3-ylamino)-benzoate (4.8 g, 14.4 mmol) was mixed with 50 ml of THF. To the mixture, 28 ml of 3 M methylmagnesium bromide was added slowly at room temperature and then stirred at room temperature for 3 hrs. After the reaction finished, ammonium chloride solution was added to the reaction mixture, which was then extracted with ethyl acetate/water to receive the organic layer. The solvent was removed under reduced pressure, and the crude product was purified by column chromatography, yielding 4.5 g of 2-(2-(dibenzo[b,d]thiophen-3-ylamino)phenyl)propan-2-ol as yellow oil (93.7%), $^1$H NMR (CDCl$_3$, 400 MHz): chemical shift (ppm) 8.94 (s, 1H), 7.83 (d, 1H), 7.62 (d, 1H), 7.55 (d, 1H), 7.41-7.36 (m, 3H), 7.29 (m, 1H), 6.94 (m, 1H), 6.78-6.75 (d, 2H), 6.59 (d, 1H), 3.91 (s, 1H), 1.35 (s, 6H).

Synthesis of 12,12-dimethyl-7,12-dihydrobenzo[4,5]thieno[3,2-b]-acridine

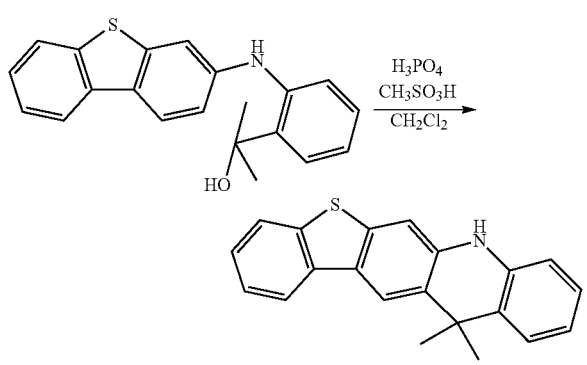

The compound 2-(2-(dibenzo[b,d]thiophen-3-ylamino)phenyl)-propan-2-ol (10 g, 30 mmol) was mixed with 150 ml of CH$_2$Cl$_2$. To the mixture, 19 ml of methane sulfonic acid and 14 ml of phosphoric acid were added slowly at room temperature and then stirred at room temperature for 12 hrs. After the reaction finished, ice-cold water was added to the reaction mixture, and 20% sodium hydroxide solution was added thereto. The reaction mixture was extracted with ethyl acetate/water to receive the organic layer. The solvent was removed under reduced pressure, and the crude product was purified by column chromatography, yielding 5.3 g of 12,12-dimethyl-7,12-dihydrobenzo[4,5]thieno[3,2-b]acridine as yellow solid (56%), $^1$H NMR (CDCl$_3$, 400 MHz): chemical shift (ppm) 8.97 (s, 1H), 7.81 (s, 1H), 7.73 (d, 1H), 7.45 (d, 1H), 7.38 (d, 1H), 7.28 (m, 1H), 7.18 (dd, 1H), 7.07 (m, 1H), 6.89 (s, 1H), 6.83-6.79 (m, 2H), 1.38 (s, 6H).

Synthesis of Intermediate G

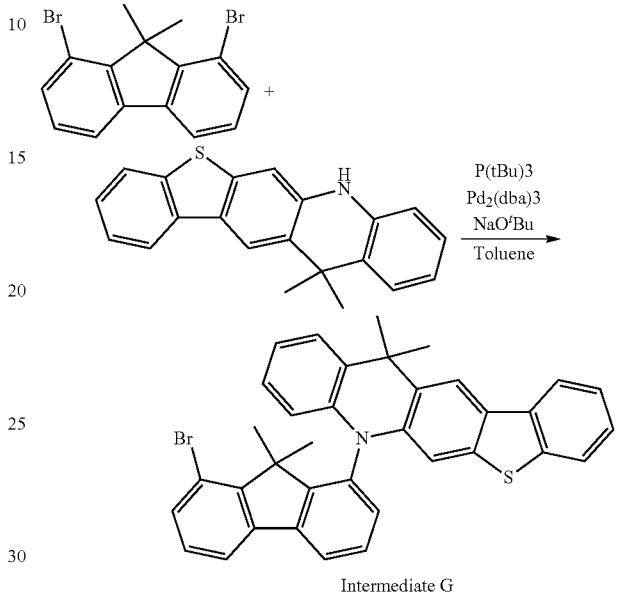

Intermediate G

The same synthesis procedure as in Synthesis of Intermediate A was used, except that 1,8-dibromo-9,9-dimethyl-9H-fluorene (7.0 g, 20 mmol) was used instead of 4,6-dibromobenzofuran and 12,12-dimethyl-7,12-dihydrobenzo[4,5]thieno[3,2-b]acridine (6.3 g, 20 mmol) was used instead of bis(4-tert-butylphenyl)amine to obtain 7.6 g (65%) of Intermediate G.

Synthesis of Intermediate H

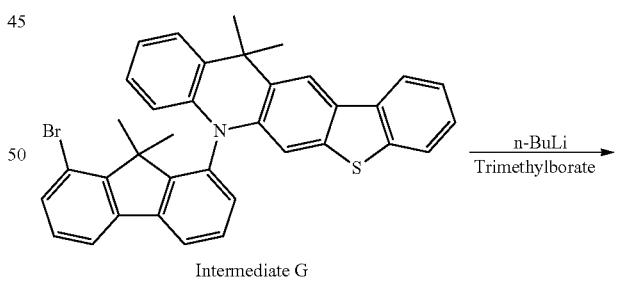

Intermediate G

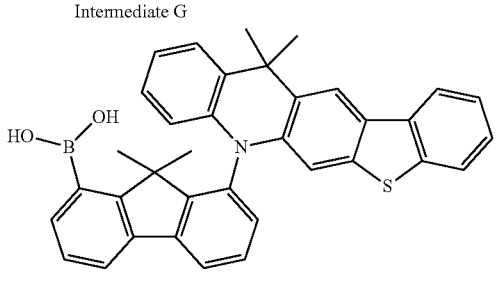

Intermediate H

The same synthesis procedure as in Synthesis of Intermediate B was used, except that Intermediate G (7.6 g, 13 mmol) was used instead of Intermediate A to obtain 4.9 g (69%) of Intermediate H.

Synthesis of 5,6-dibromoacenaphthylene

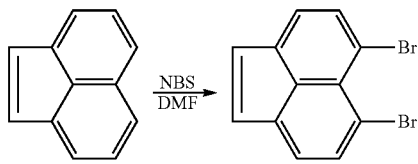

A mixture of 70 g (460 mmol) of Acenaphthylene and 100 ml of DMF was placed under nitrogen and stirred at 0° C. After 180 g (1012 mmol) of N-bromosuccinimide in 300 ml of DMF was added dropwise, the temperature was raised to room temperature and the mixture was stirred for 18 hours. The precipitated product was filtered off with suction and washed with EtOH. The residue was recrystallized from EtOH to give product (47 g, 151.8 mmol, 33%).

Synthesis of Intermediate I

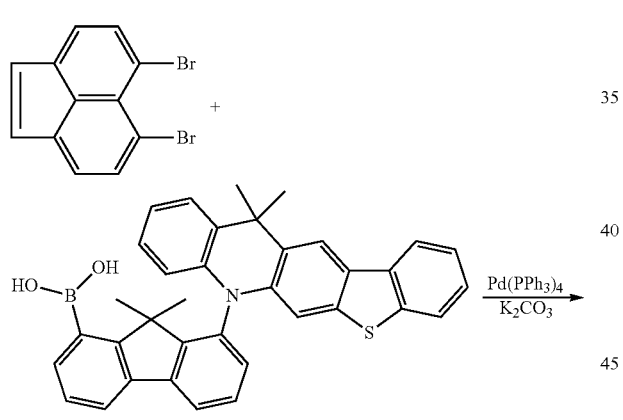

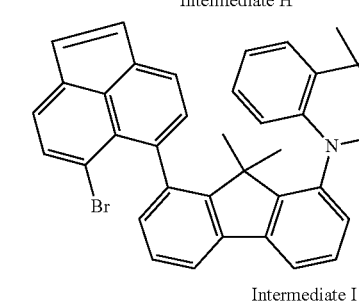

Intermediate I

The same synthesis procedure as in Synthesis of Intermediate C was used, except that 5,6-dibromoacenaphthylene (2.7 g, 8.9 mmol) was used instead of 5,6-dibromo-1,2-dihydroacenaphthylene and Intermediate H (4.9 g, 8.9 mmol) was used instead of Intermediate B to obtain 4.1 g (63%) of Intermediate I.

Synthesis of EX95

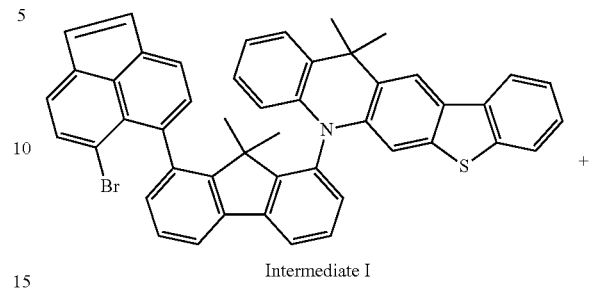

Intermediate I

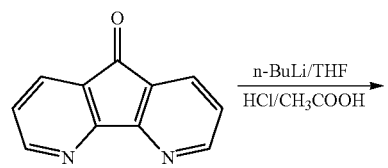

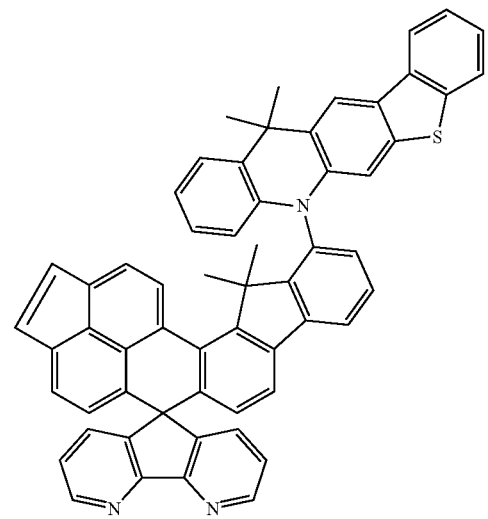

The same synthesis procedure as in Synthesis of EX1 was used, except that Intermediate I (4.1 g, 5.6 mmol) was used instead of Intermediate C and 4,5-Diazafluoren-9-one (1.0 g, 5.6 mmol) was used instead of 9H-fluoren-9-one to obtain 1.6 g (35%) of EX95. MS(m/z, EI$^+$): 818.3.

Example 6

Synthesis of Intermediate J

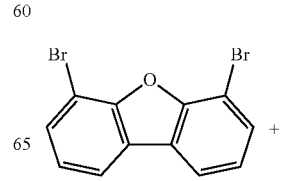

75

-continued

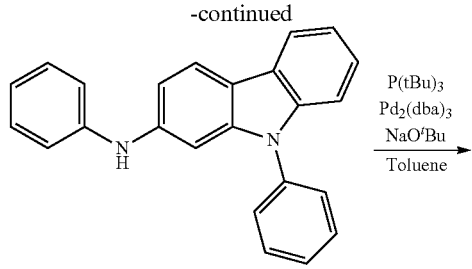

P(tBu)₃
Pd₂(dba)₃
NaOᵗBu
—————→
Toluene

76

Synthesis of Intermediate L

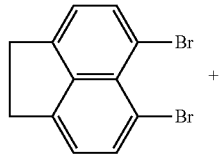

+

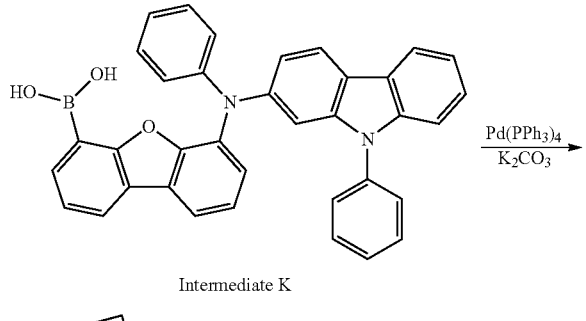

Pd(PPh₃)₄
—————→
K₂CO₃

Intermediate K

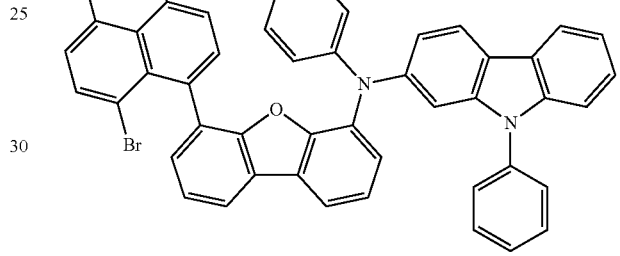

Intermediate J

The same synthesis procedure as in Synthesis of Intermediate A was used, except that 6.7 g (20 mmol) of N,9-diphenyl-9H-carbazol-2-amine was used instead of bis(4-tert-butylphenyl)amine to obtain 6.8 g (59%) of Intermediate J.

Synthesis of Intermediate K

Intermediate L

The same synthesis procedure as in Synthesis of Intermediate C was used, except that 4.8 g (8.8 mmol) of Intermediate K was used instead of Intermediate B to obtain 4.0 g (62%) of Intermediate L.

Synthesis of EX21

Intermediate J n-BuLi
—————→
Trimethylborate

Intermediate L

+

Intermediate K n-BuLi/THF
—————→
HCl/CH₃COOH

The same synthesis procedure as in Synthesis of Intermediate B was used, except that 6.8 g (11.8 mmol) of Intermediate J was used instead of Intermediate A to obtain 4.8 g (75%) of Intermediate K.

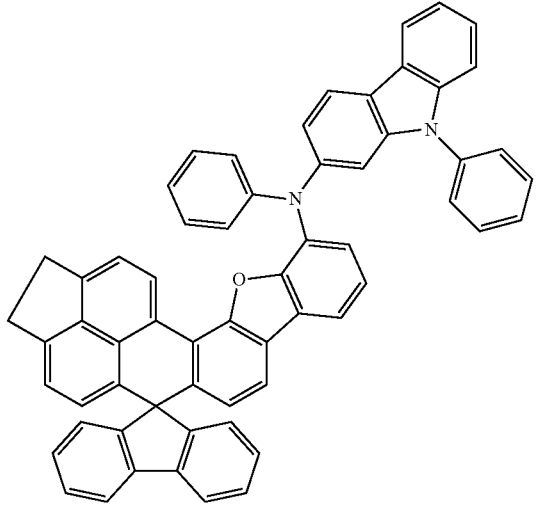

The same synthesis procedure as in Synthesis of EX1 was used, except that 4.0 g (5.5 mmol) of Intermediate L was used instead of Intermediate C to obtain 1.9 g (43%) of EX21. MS(m/z, EI⁺): 813.3.

Example 7

Synthesis of EX23

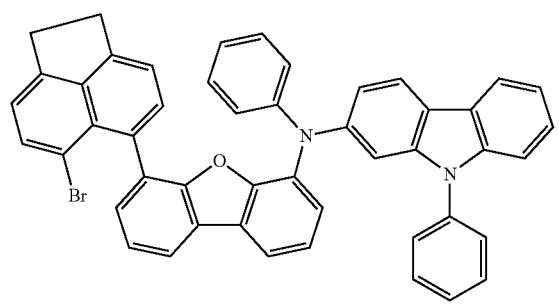

Intermediate L

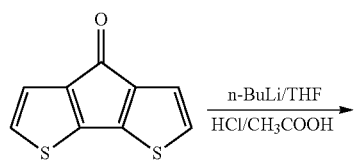

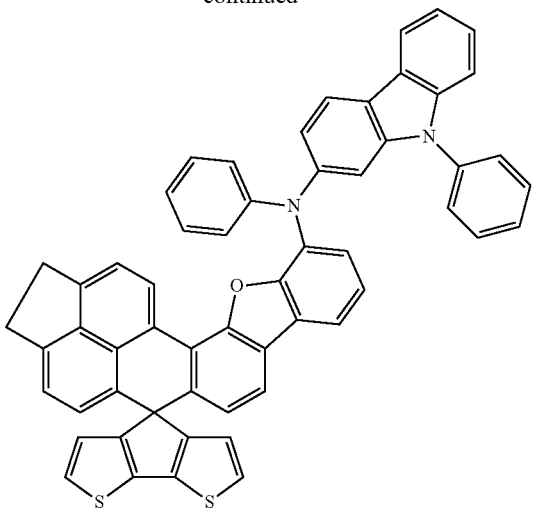

The same synthesis procedure as in Synthesis of EX1 was used, except that 4.0 g (5.5 mmol) of Intermediate L was used instead of Intermediate C and 1.0 g (5.5 mmol) of Cyclopentadithiophene Ketone was used instead of 9H-fluoren-9-one to obtain 2.1 g (47%) of EX23. MS(m/z, EI⁺): 825.2.

General Method of Producing Organic EL Device

ITO-coated glasses with 9-12 ohm/square in resistance and 120-160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1-0.3 nm/sec) are precisely monitored or set with the aid of a quartz-crystal monitor. It is also possible, as described above, for individual layers to consist of more than one compound, i.e. in general a host material doped with a dopant material and/or co-deposited with a co-host. This is successfully achieved by co-vaporization from two or more sources, which means the 5,12-dihydrotetracene derivatives of the present invention are thermally stable.

Dipyrazino[2,3-f: 2,3-]quinoxaline-2,3,6,7,10,11-hexacarbonitrile (HAT-CN) is used as hole injection layer in this organic EL device. N,N-Bis(naphthalene-1-yl)-N,N-bis (phenyl)-benzidine (NPB) is most widely used as the hole transporting layer. 10,10-dimethyl-13-(3-(pyren-1-yl)phenyl)-10H-indeno[2,1-b]triphenylene (H1), 10,10-dimethyl-12-(4-(pyren-1-yl)phenyl)-10H-indeno[2,1-b]triphenylene (H2), and 10,10-dimethyl-12-(10-(4-(naphthalene-1-yl)-phenyl) anthracen-9-yl)-1 OH-indeno[2,1-b]triphenylene (H3) are used as emitting hosts in organic EL devices, and N1,N1,N6,N6-tetram-tolylpyrene-1,6-diamine (D1) is used as blue dopant for comparison. HB3 (see the following chemical structure) is used as hole blocking material (HBM), and 2-(naphthalen-1-yl)-9-(4-(1-(4-(10-(naphthalene-2-yl) anthracen-9-yl)phenyl)-1H-benzo[d]imidazol-2-yl)phenyl)-1,10-phenanthroline (ET2) is used as electron transporting material to co-deposit with 8-hydroxyquinolato-lithium (LiQ, as shown below) in organic EL devices. The chemical structures of conventional OLED materials and the exemplary heteroaromatic compounds of the present invention for producing control and exemplary organic EL devices in this invention are shown as follows:
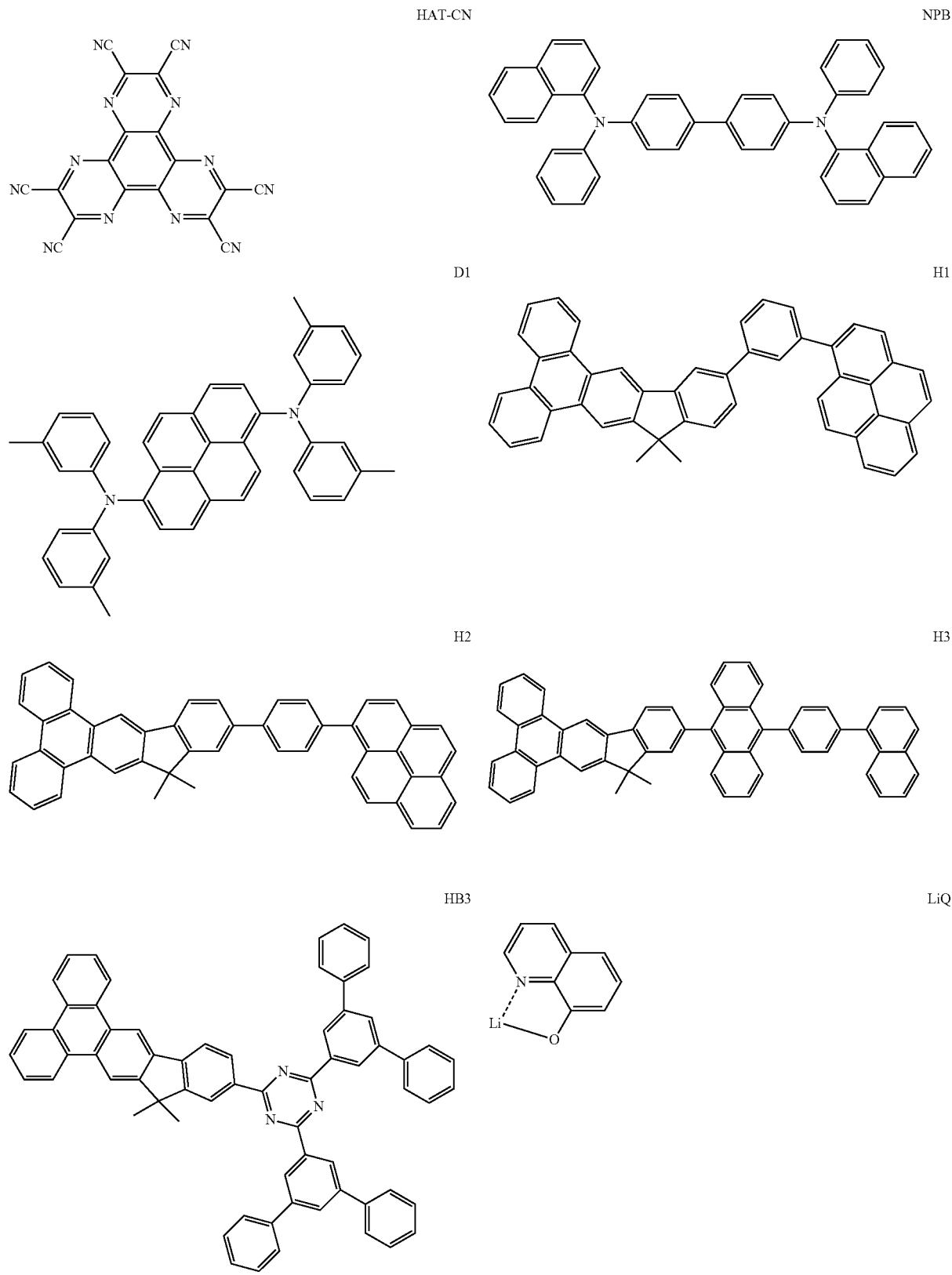

ET2
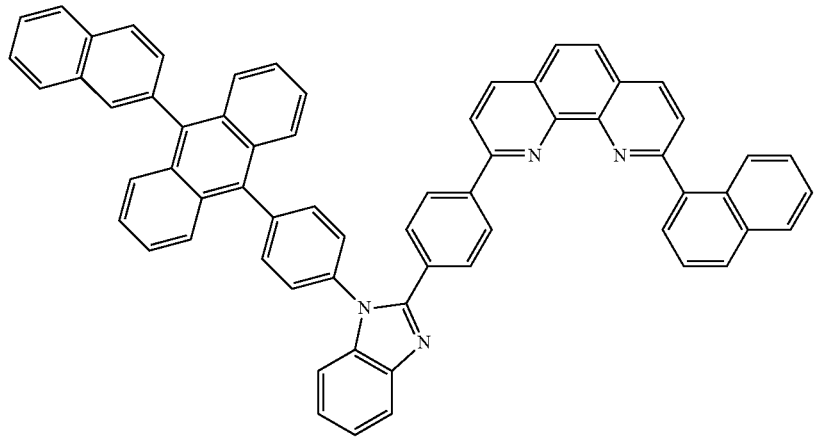
EX1
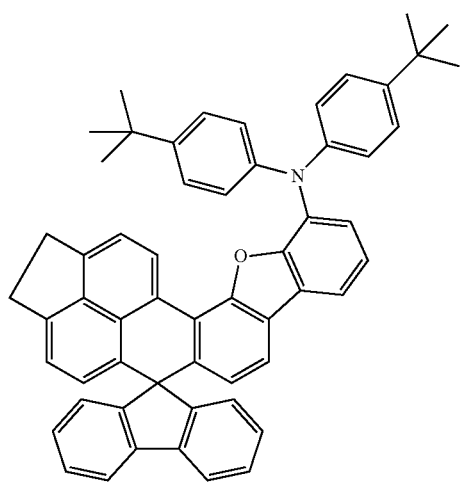
EX6
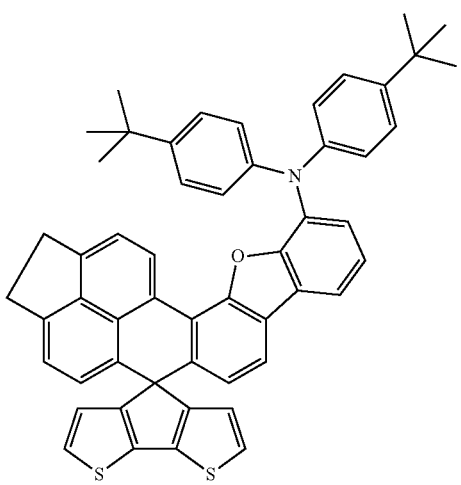
EX9
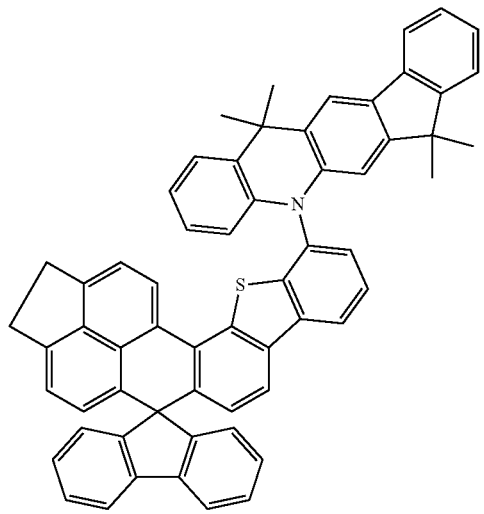
EX10
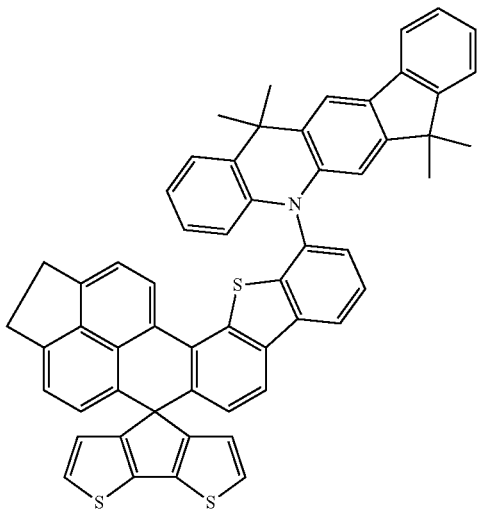

-continued

EX21

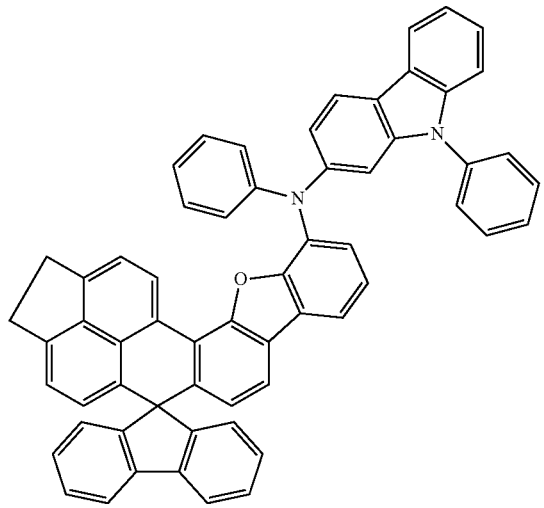

EX23

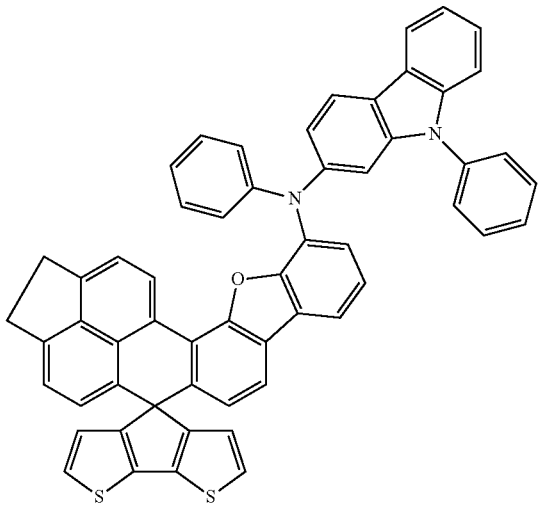

EX95

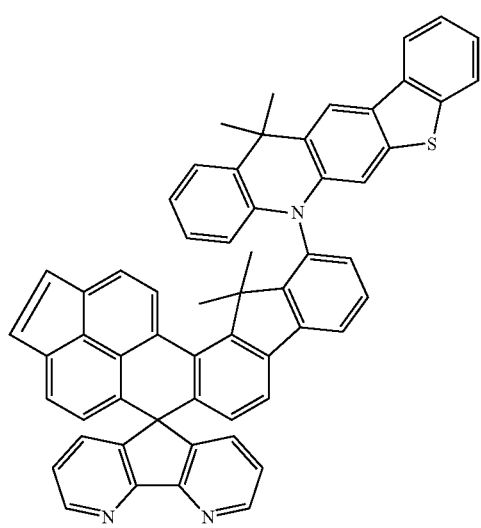

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or Li$_2$O. On the other hand, after the organic EL device fabrication, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

Example 8

Using a procedure analogous to the above mentioned general method, organic EL devices emitting blue light and having the following device structure as shown in the FIGURE were produced: ITO/HAT-CN (20 nm)/NPB (110 nm)/Emitting host doped with 5% Emitting dopant (30 nm)/HB3/ET2 doped 50% LiQ(35 nm)/LiQ(1 nm)/Al(160 nm). In the device illustrated in the FIGURE, the hole injection layer 20 is deposited onto the transparent electrode 10, the hole transport layer 30 is deposited onto the hole injection layer 20, the emitting layer 40 is deposited onto the hole transport layer 30, the hole blocking layer 50 is deposited onto the emitting layer 40, the electron transport layer 60 is deposited onto the hole blocking layer 50, the electron injection layer 70 is deposited onto the electron transport layer 60, and the metal electrode 80 is deposited onto the electron injection layer 70. The I-V-B (at 1000 nits) test reports of these organic EL devices are summarized in Table 1 below. The half-life time is defined as the time the initial luminance of 1000 cd/m$^2$ has dropped to half.

TABLE 1

| Emitting Host | Emitting dopant | Voltage (V) | Efficiency (cd/A) | Device Colour | Half-life time(hour) |
|---|---|---|---|---|---|
| H1 | EX1 | 2.8 | 6.3 | blue | 250 |
| H1 | EX6 | 2.9 | 6.1 | blue | 245 |
| H1 | EX9 | 3.0 | 5.9 | blue | 231 |
| H1 | EX10 | 2.8 | 6.5 | blue | 260 |
| H1 | Ex21 | 3.0 | 5.8 | blue | 220 |
| H1 | EX23 | 3.1 | 5.7 | blue | 210 |
| H1 | EX95 | 3.1 | 5.6 | blue | 195 |
| H1 | D1 | 3.5 | 5.3 | blue | 180 |
| H2 | EX1 | 2.8 | 6.9 | blue | 300 |
| H2 | EX6 | 2.9 | 6.7 | blue | 290 |
| H2 | EX9 | 2.9 | 6.6 | blue | 285 |
| H2 | EX10 | 2.8 | 7.1 | blue | 310 |
| H2 | Ex21 | 3.0 | 6.5 | blue | 280 |
| H2 | EX23 | 3.3 | 6.3 | blue | 230 |
| H2 | EX95 | 3.4 | 6.0 | blue | 210 |
| H2 | D1 | 3.8 | 5.5 | blue | 210 |
| H3 | EX1 | 3.0 | 7.0 | blue | 330 |
| H3 | EX6 | 3.0 | 6.8 | blue | 310 |
| H3 | EX9 | 3.1 | 6.5 | blue | 300 |
| H3 | EX10 | 2.8 | 7.2 | blue | 350 |
| H3 | Ex21 | 3.2 | 6.4 | blue | 295 |
| H3 | EX23 | 3.2 | 6.2 | blue | 291 |
| H3 | EX95 | 3.3 | 6.1 | blue | 285 |
| H3 | D1 | 3.5 | 5.5 | blue | 280 |

In the above test report of organic EL devices (see Table 1), we show that the organic material with formula (1) used as emitting dopant material for organic EL devices in the present invention exhibits better performance than the prior art organic EL materials. More specifically, the organic EL devices of the present invention use the organic material with formula (1) as emitting dopant material to collocate with emitting host material, such as H1, H2 and H3, show lower power consumption, higher efficiency, and longer half-life time.

To sum up, the present invention discloses a heteroaromatic compound, which can be used as the fluorescent dopant material of the light emitting layer in organic EL devices. The mentioned heteroaromatic compound is represented by the following formula (1):

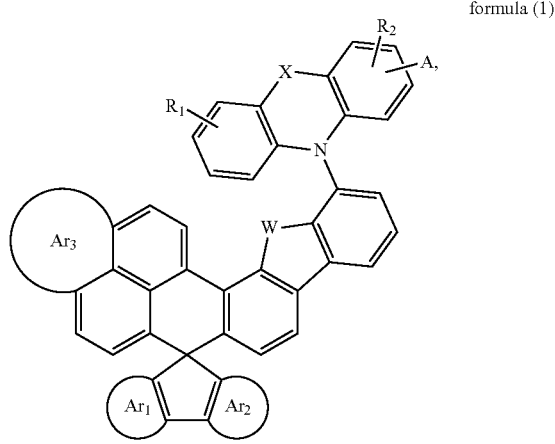

formula (1)

wherein $Ar_1$ and $Ar_2$ are independently an aryl group or a heteroaryl group having 4 to 6 ring carbon atoms; $Ar_3$ is a cycloalkyl group, a cycloalkenyl group, or an aryl group having 5 to 6 ring carbon atoms; $R_1$ and $R_2$ are independently a hydrogen atom, a substituted or unsubstituted alkyl group having 1 to 36 carbon atoms, a substituted or unsubstituted aryl group having 6 to 36 carbon atoms, or a substituted or unsubstituted aralkyl group having 6 to 36 carbon atoms; W represents a divalent bridge selected from the group consisting of O, S, $CR_3R_4$, $NR_5$, and $SiR_6R_7$, and $R_3$ to $R_7$ are independently a hydrogen atom or a substituted or unsubstituted alkyl group having 1 to 20 carbon atoms; X is absent or a divalent bridge selected from the group consisting of O, S, $CR_8R_9$, $NR_{10}$, and $SiR_{11}R_{12}$; A is absent or represents formula (2) below:

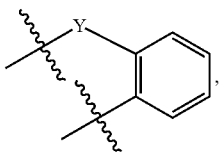

formula (2)

wherein Y represents a divalent bridge selected from the group consisting of O, S, $CR_{13}R_{14}$, $NR_{15}$, and $SiR_{16}R_{17}$; and $R_8$ to $R_{17}$ are independently a hydrogen atom, a substituted or unsubstituted alkyl group having 1 to 36 carbon atoms, a substituted or unsubstituted aryl group having 6 to 36 carbon atoms, a substituted or unsubstituted aralkyl group having 6 to 36 carbon atoms, or a substituted or unsubstituted heteroaryl group having 3 to 36 carbon atoms.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:
1. A heteroaromatic compound of formula (1) below:

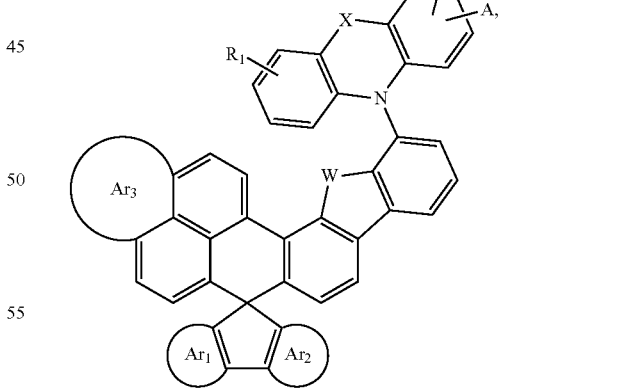

formula (1)

wherein $Ar_1$ and $Ar_2$ are independently an aryl group or a heteroaryl group having 4 to 6 ring carbon atoms; $Ar_3$ is a cycloalkyl group, a cycloalkenyl group, or an aryl group having 5 to 6 ring carbon atoms; $R_1$ and $R_2$ are independently a hydrogen atom, a unsubstituted alkyl group having 1 to 36 carbon atoms, a unsubstituted aryl group having 6 to 36 carbon atoms, or a unsubstituted aralkyl group having 6 to 36 carbon atoms; W represents a divalent bridge selected from the group consisting of O, S, $CR_3R_4$, $NR_5$, and $SiR_6R_7$, and $R_3$ to $R_7$ are independently a hydrogen atom or a unsubstituted alkyl group having 1 to 20 carbon atoms; X is absent or a divalent bridge selected from the group consisting of O, S, $CR_8R_9$, $NR_{10}$, and $SiR_{11}R_{12}$; A is absent or represents formula (2) below:

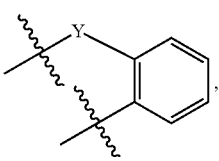

formula (2)

wherein Y represents a divalent bridge selected from the group consisting of O, S, $CR_{13}R_{14}$, $NR_{15}$, and $SiR_{16}R_{17}$; and $R_8$ to $R_{17}$ are independently a hydrogen atom, a unsubstituted alkyl group having 1 to 36 carbon atoms, a unsubstituted aryl group having 6 to 36 carbon atoms, a unsubstituted aralkyl group having 6 to 36 carbon atoms, or a unsubstituted heteroaryl group having 3 to 36 carbon atoms.

2. The heteroaromatic compound according to claim 1, wherein $Ar_1$ and $Ar_2$ are independently

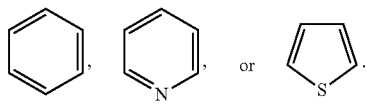

3. The heteroaromatic compound according to claim 1, wherein $Ar_3$ is

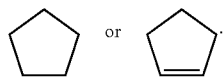 [SMILES: C1CCCC1 ; C1=CCCC1]

4. A heteroaromatic compound selected from the group consisting of following compounds:

EX1

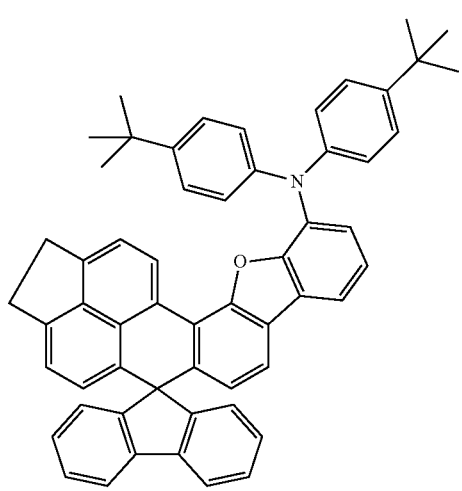

EX2

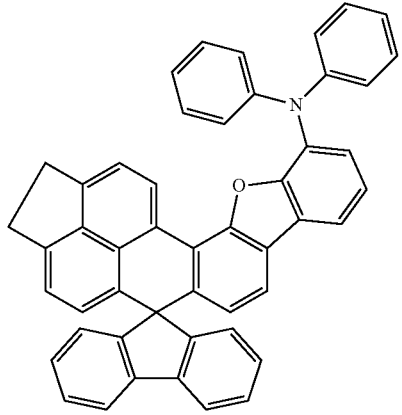

EX3

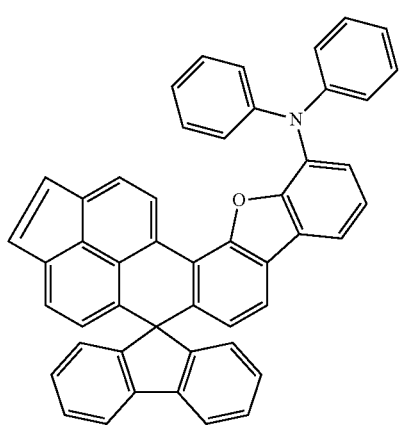

EX4

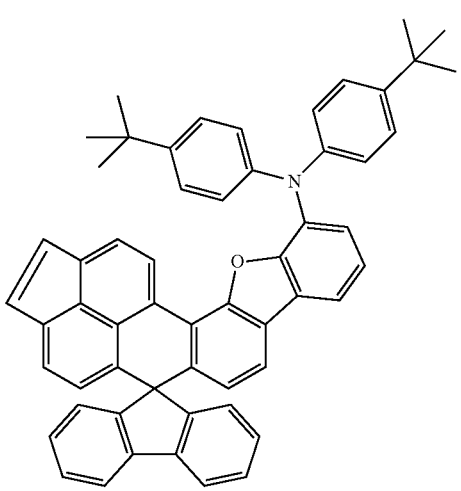

EX5
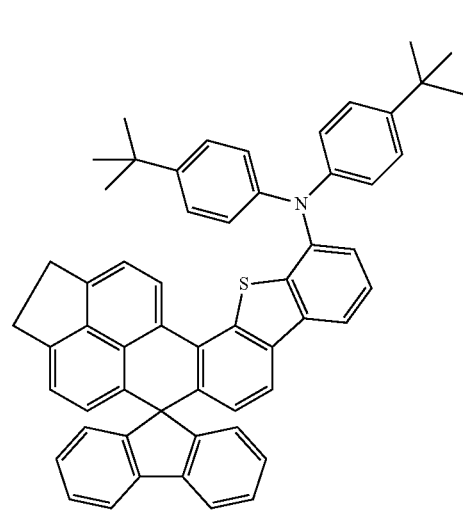
EX6
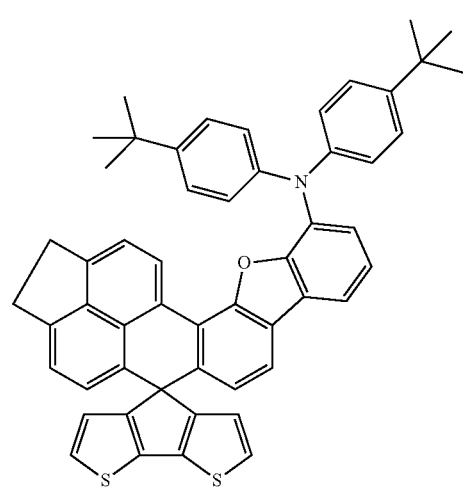
EX7
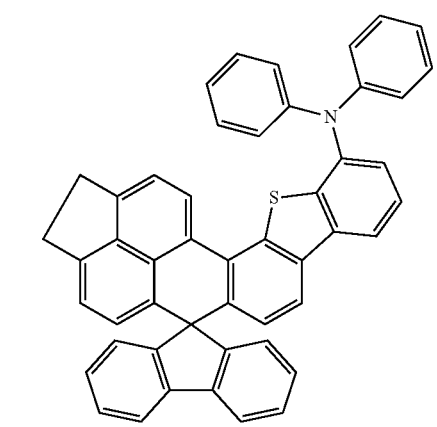
EX8
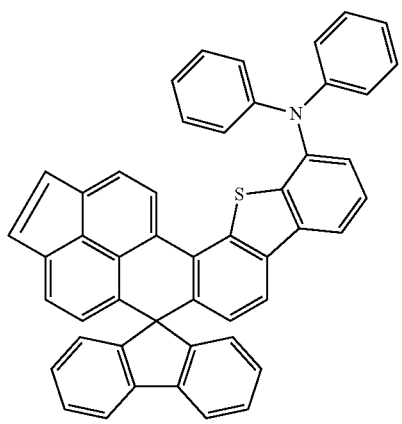
EX9
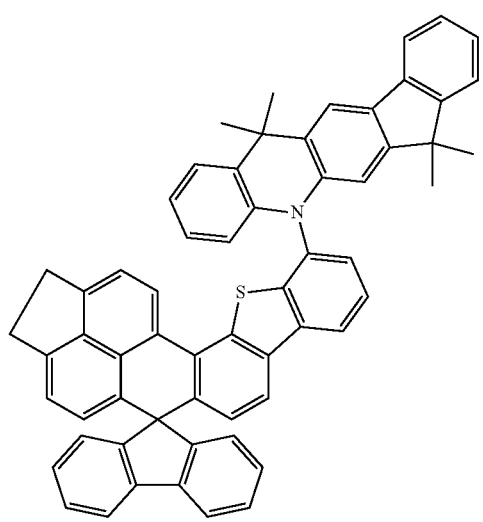
EX10
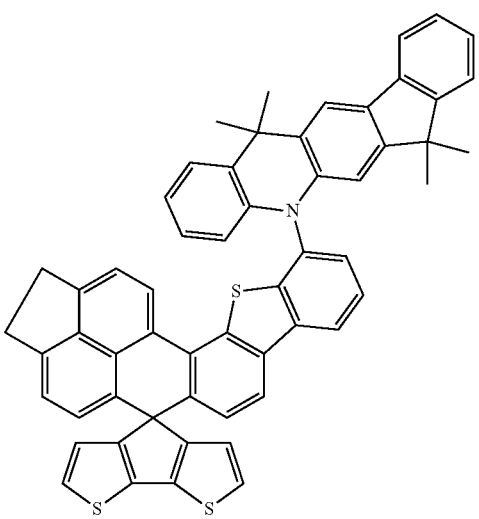

-continued
EX11
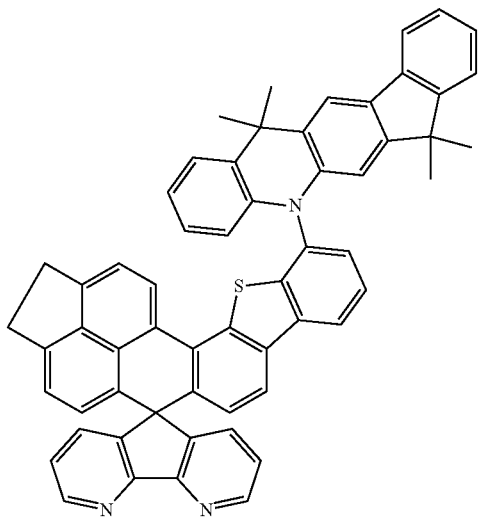
EX14
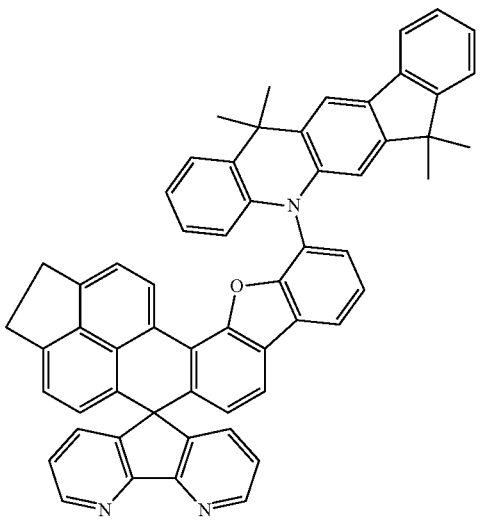
EX12
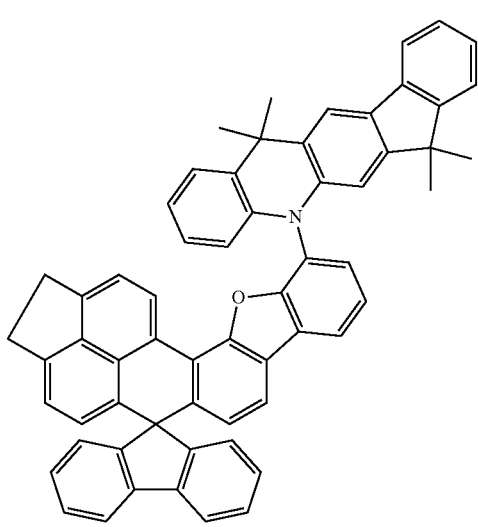
EX15
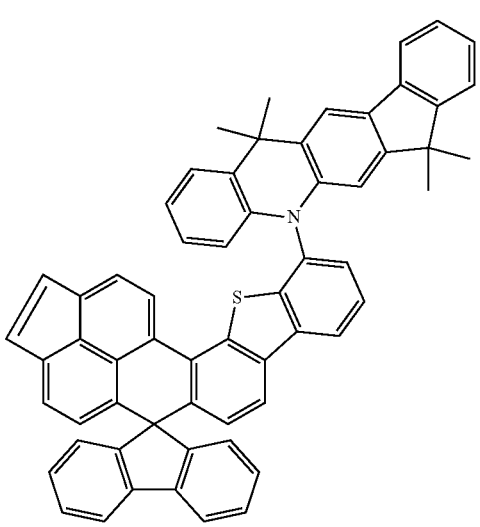
EX13
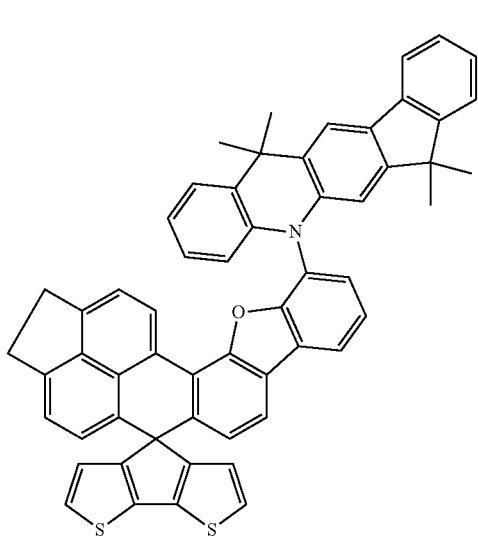
EX16
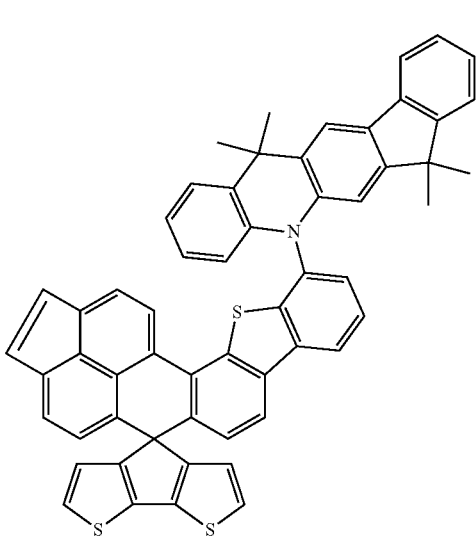

EX17
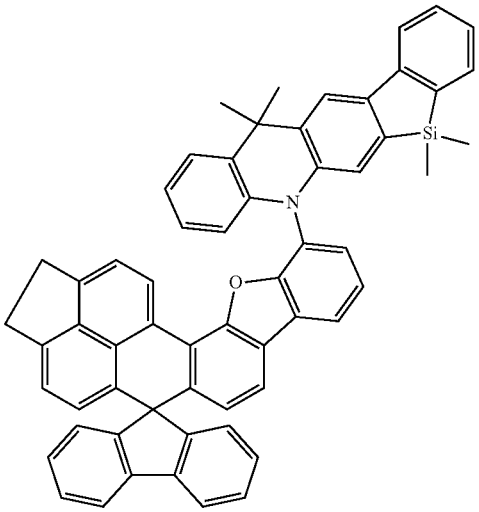
EX20
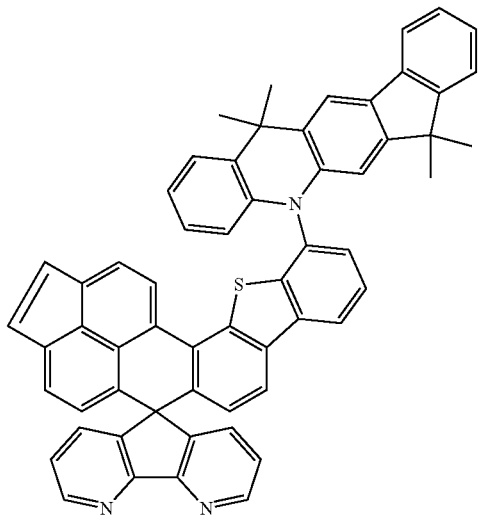
EX18
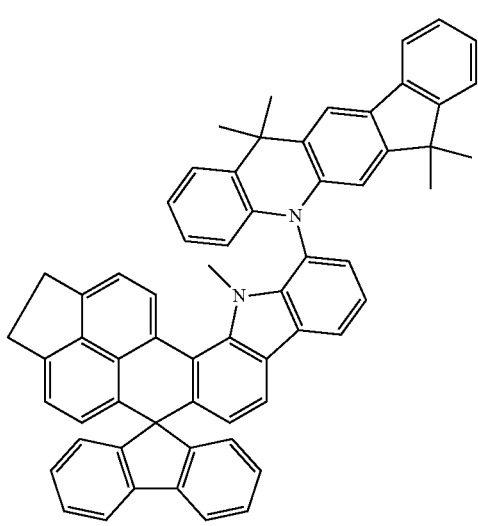
EX21
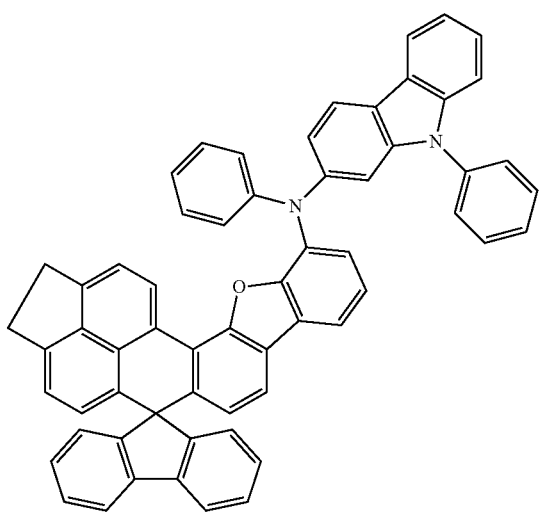
EX19
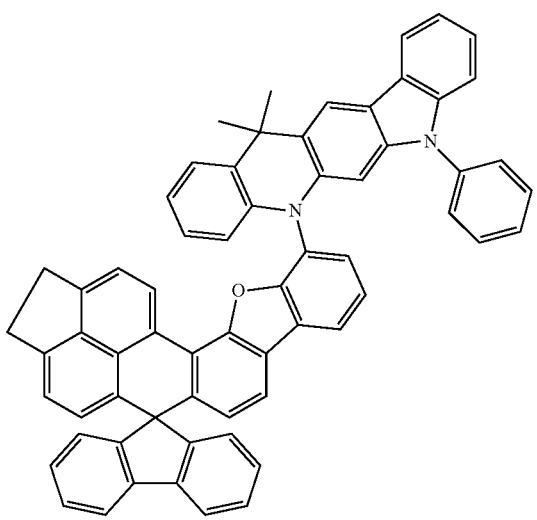
EX22
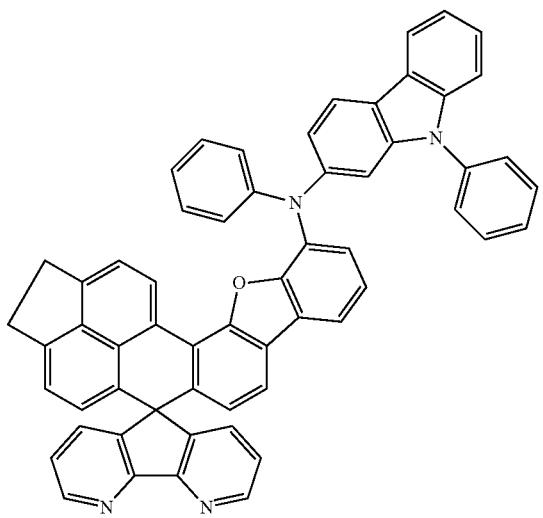

-continued
EX23
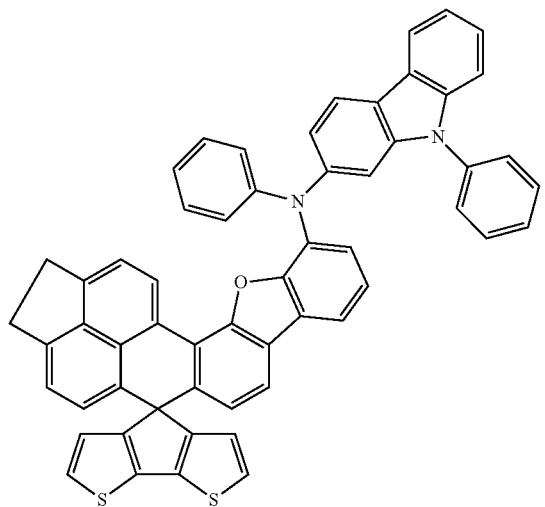
EX24
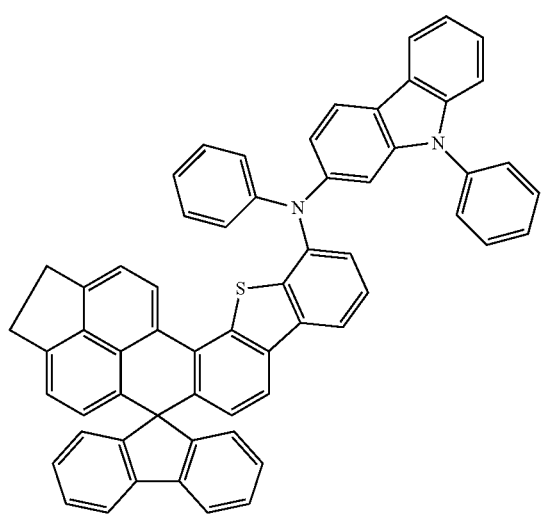
EX25
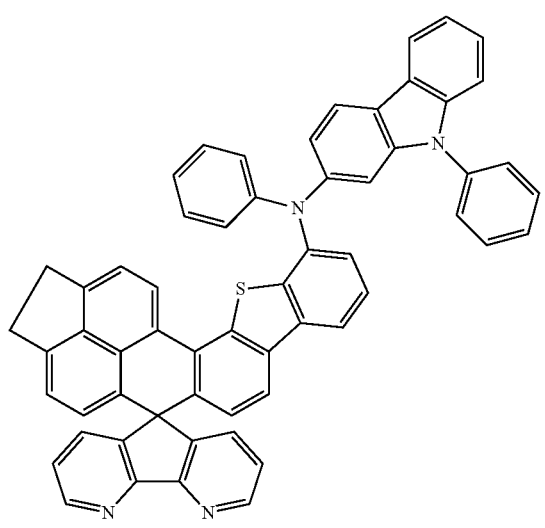
-continued
EX26
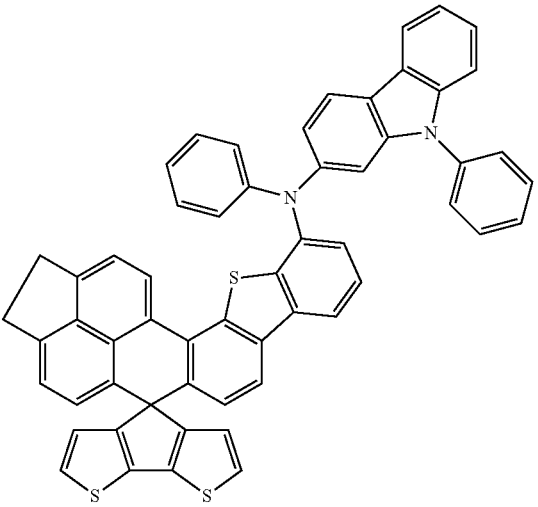
EX27
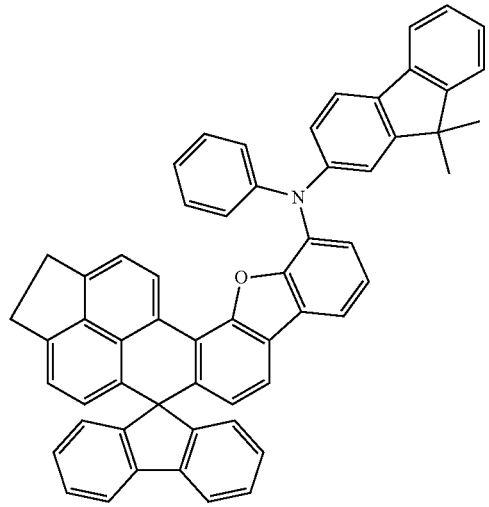
EX28
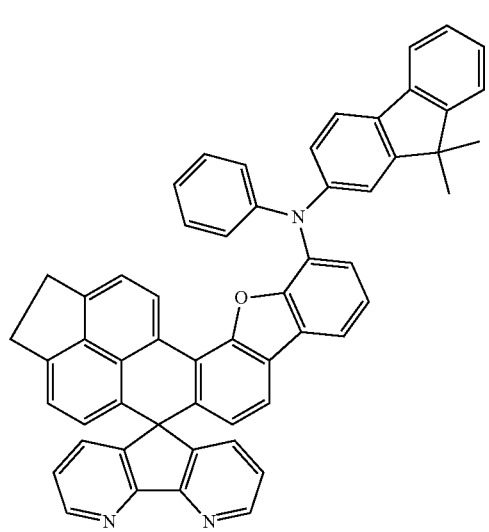

EX29
EX30
EX31
EX32
EX33
EX34
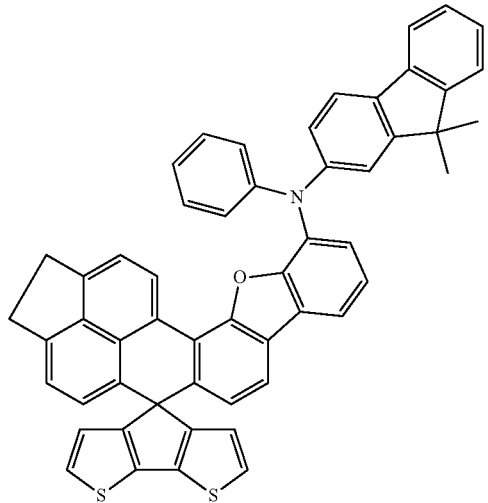
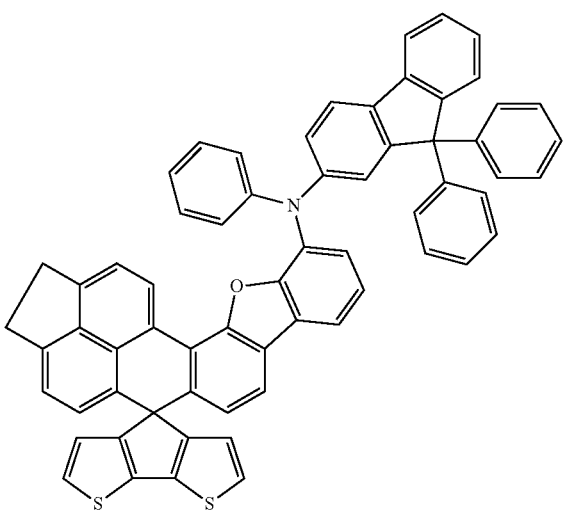
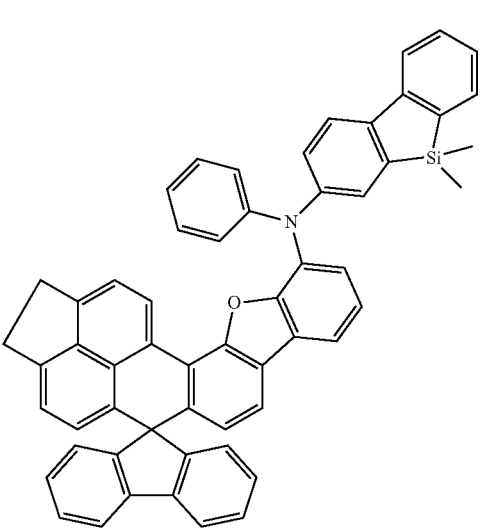
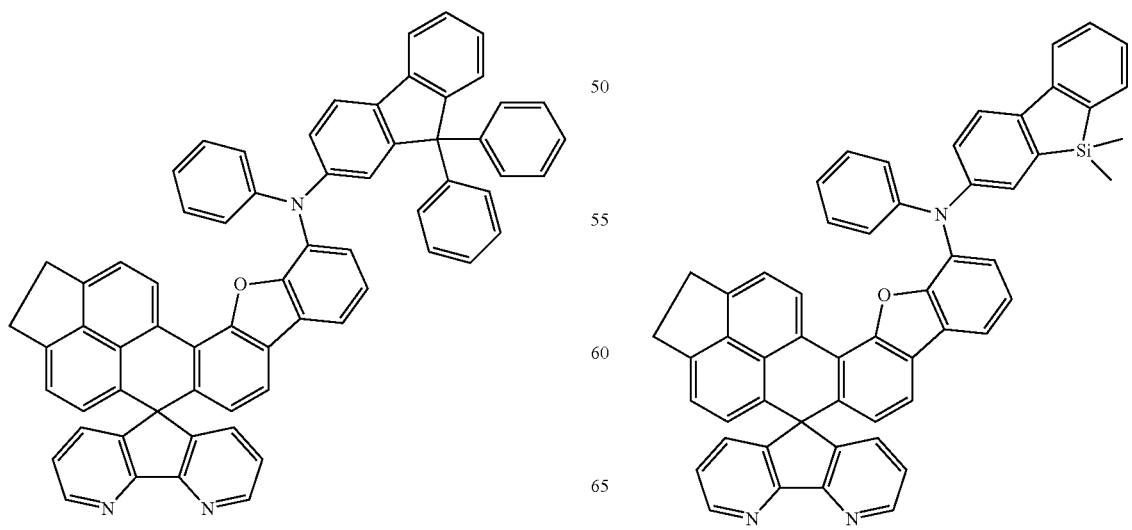

| 99 -continued | 100 -continued |
|---|---|
| EX35 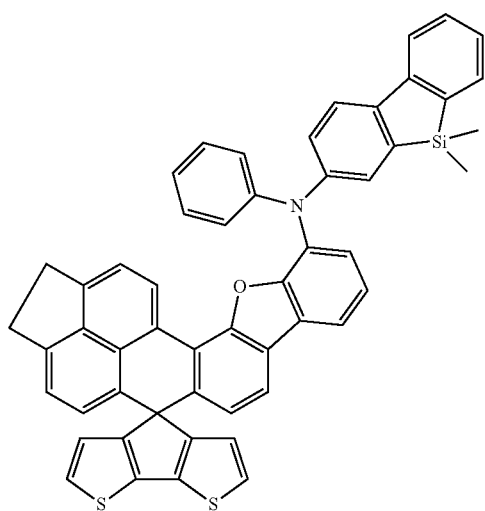 | EX38 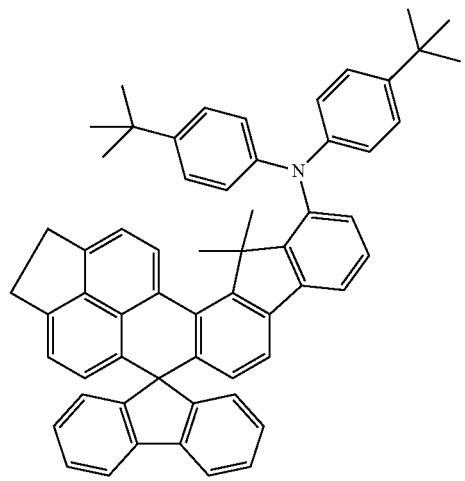 |
| EX36 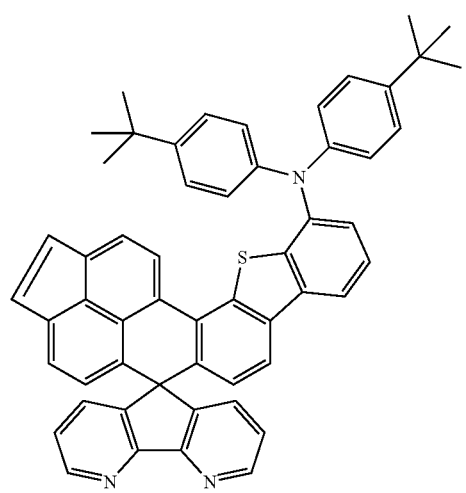 | EX39 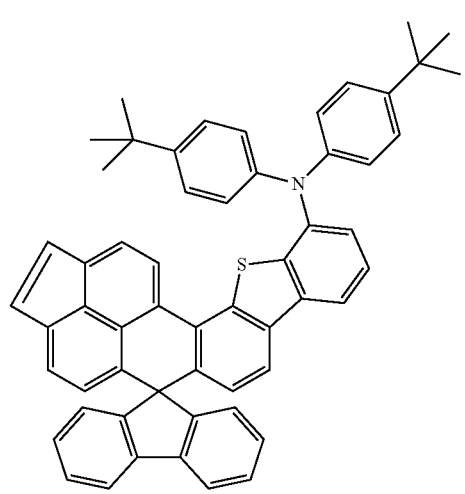 |
| EX37 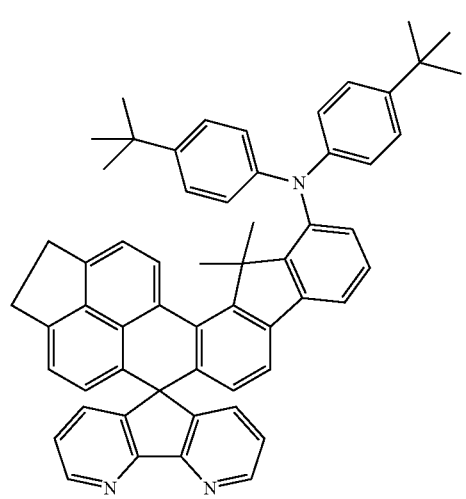 | EX40 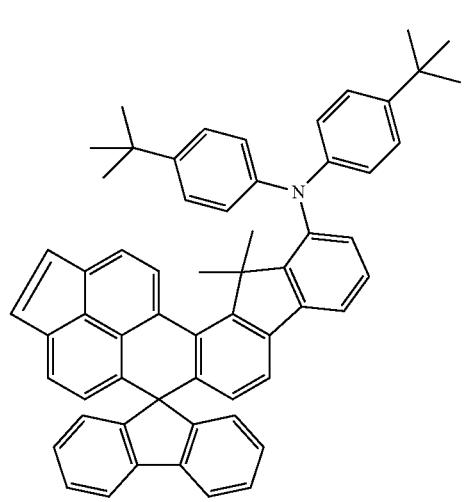 |

101
-continued
102
-continued
EX41
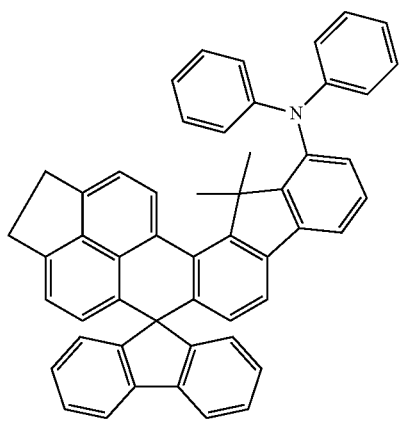
EX44
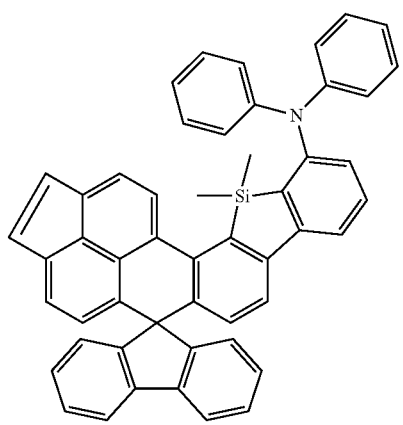
EX42
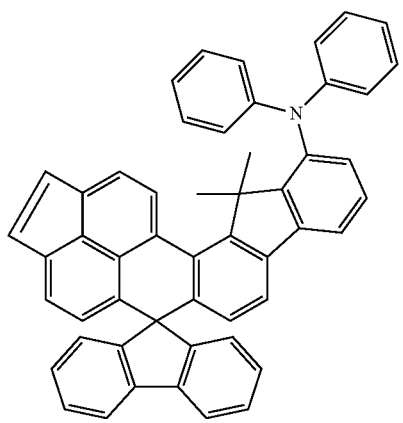
EX45
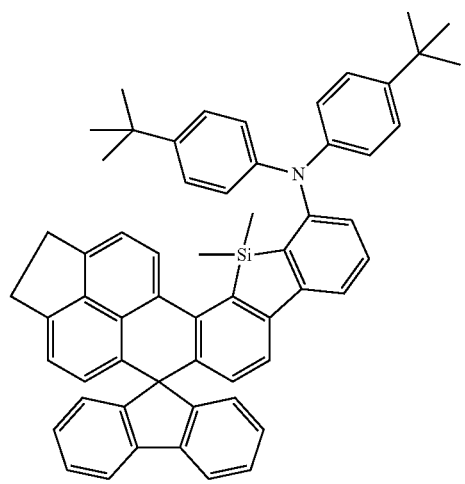
EX43
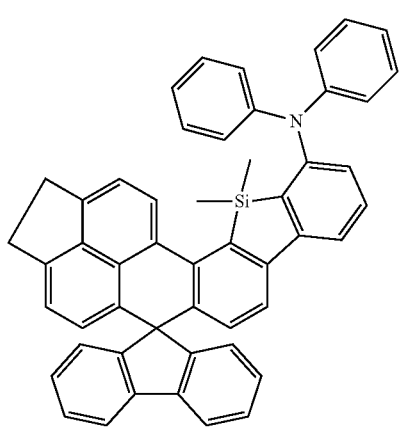
EX46
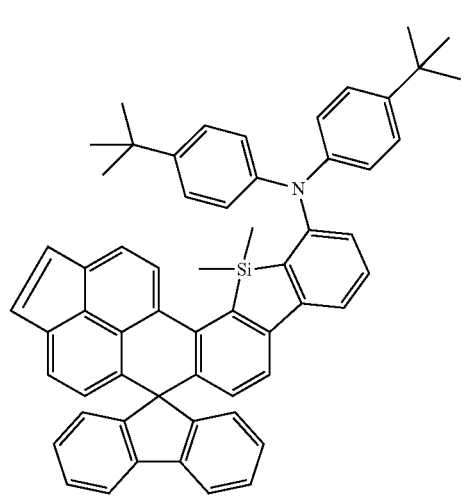

103
-continued
104
-continued
EX47
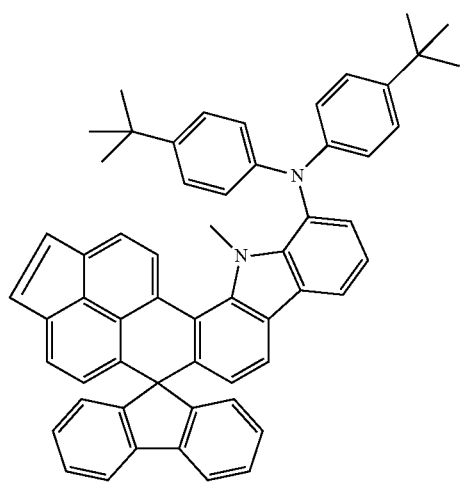
EX48
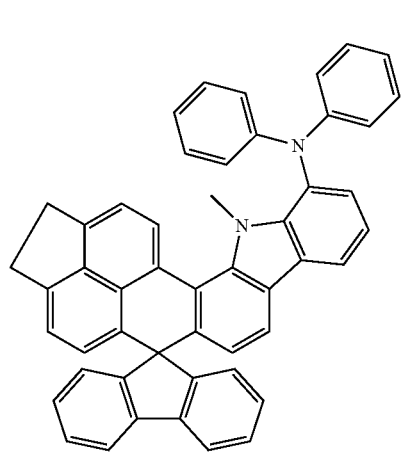
EX50
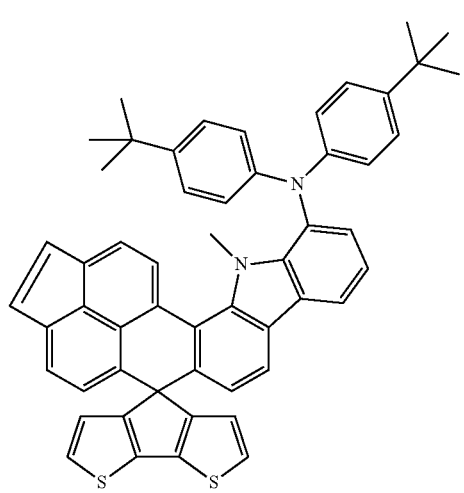
EX49
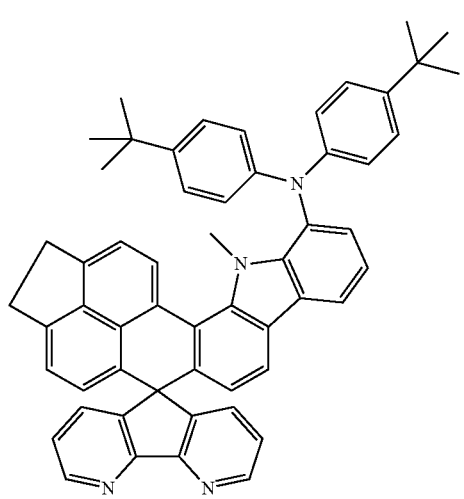
EX51
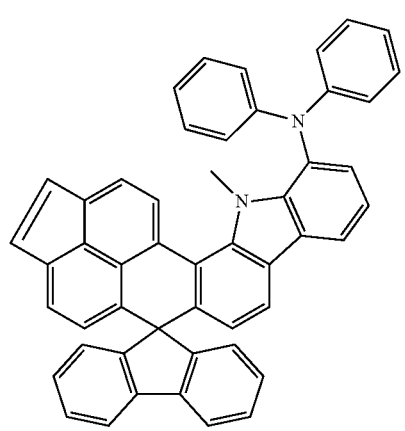
EX52
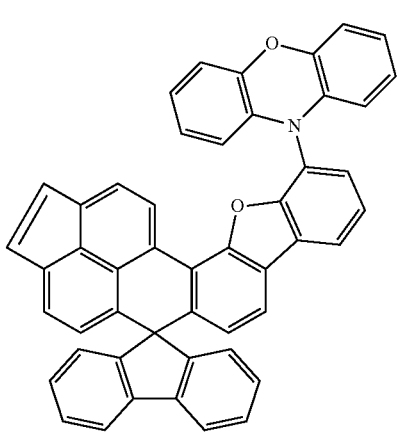

EX53
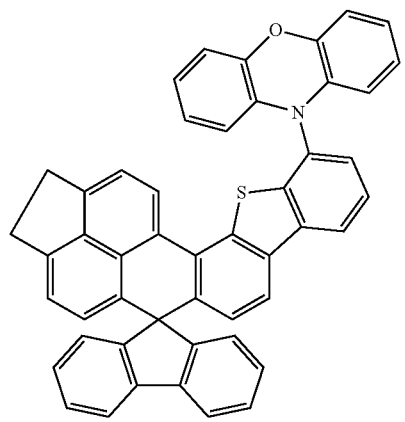
EX54
EX55
EX56
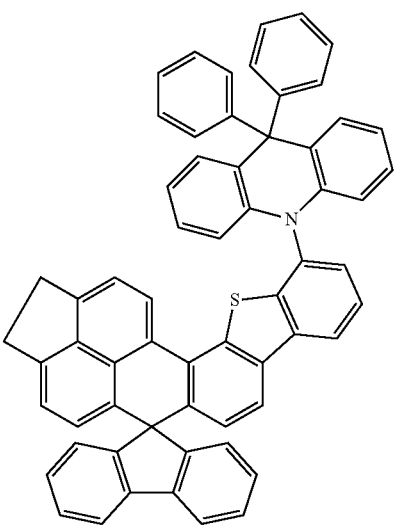
EX57
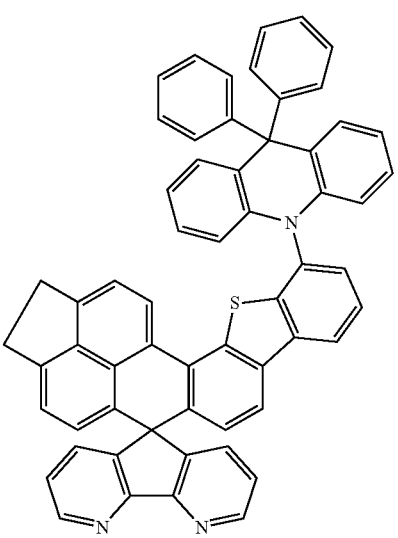
EX58
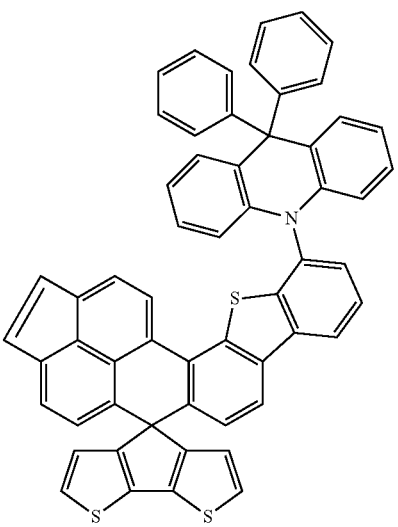

107
-continued
108
-continued
EX59
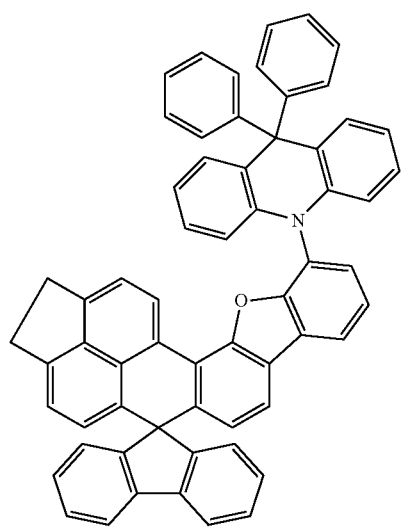
EX62
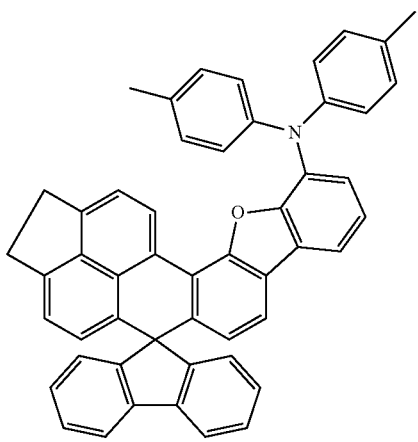
EX60
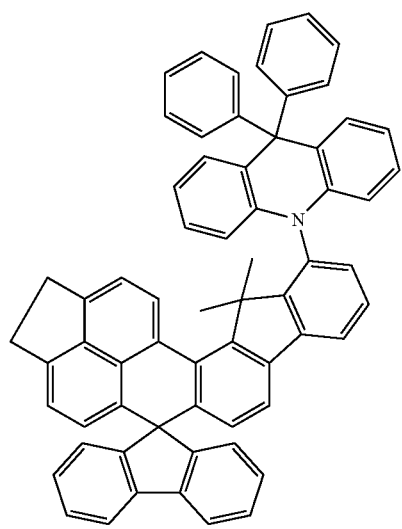
EX63
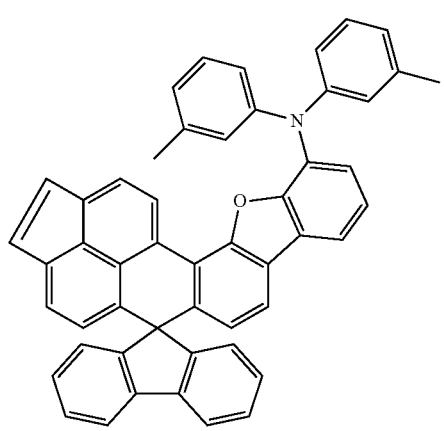
EX61
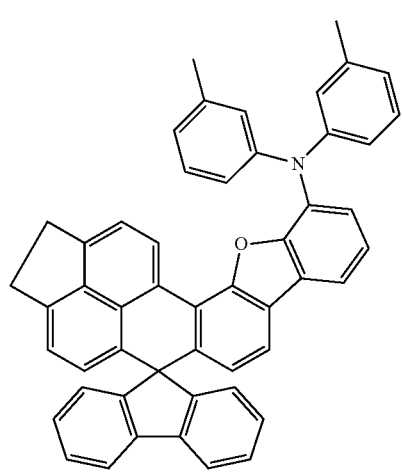
EX64
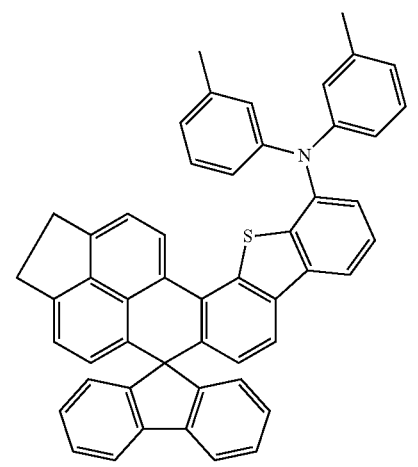

EX65
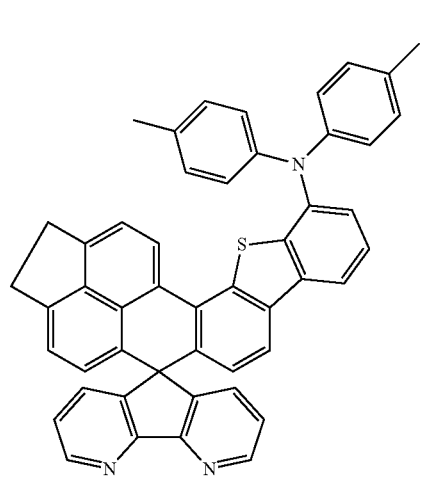
EX66
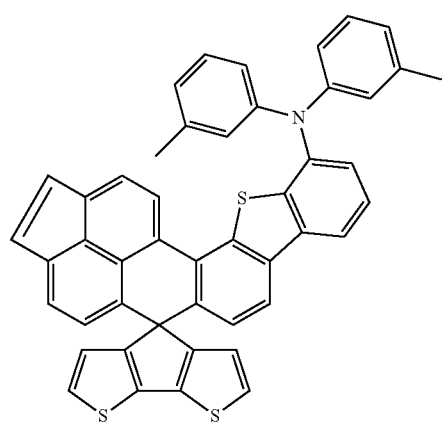
EX67
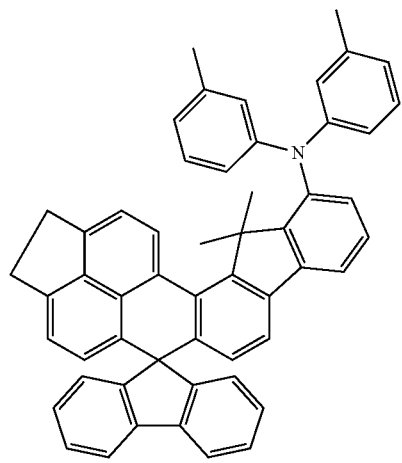
EX68
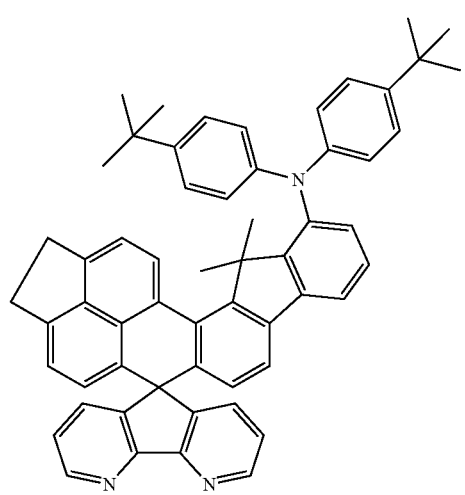
EX69
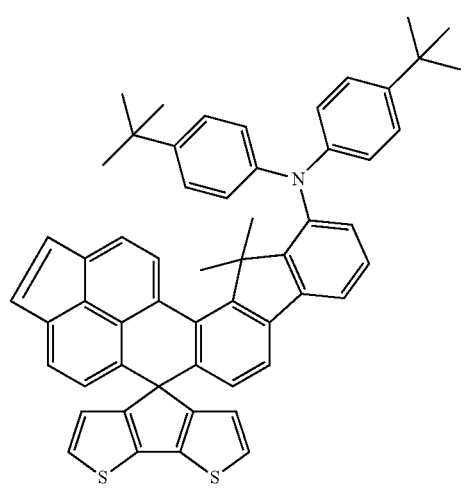
EX70
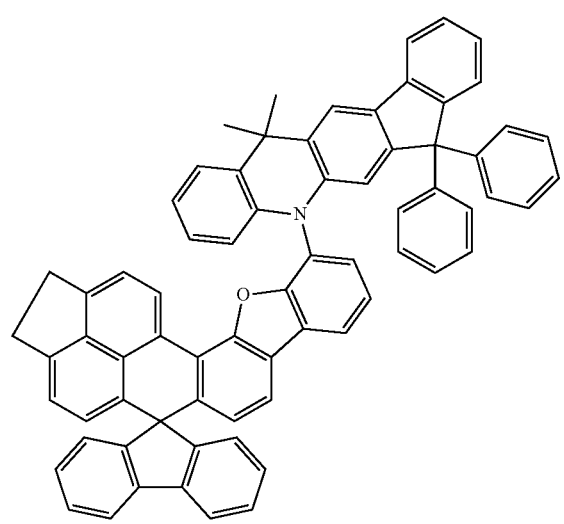

EX71
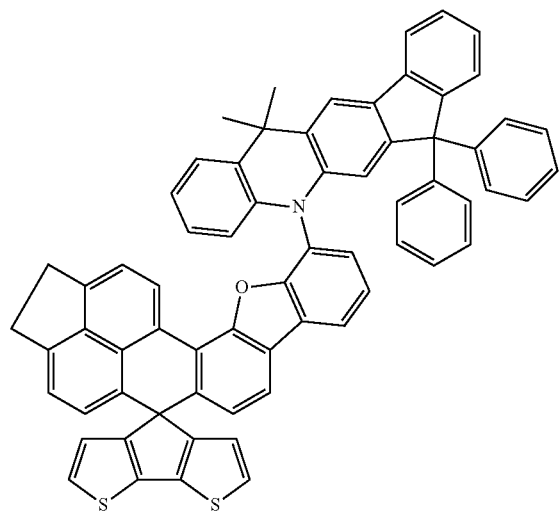
EX72
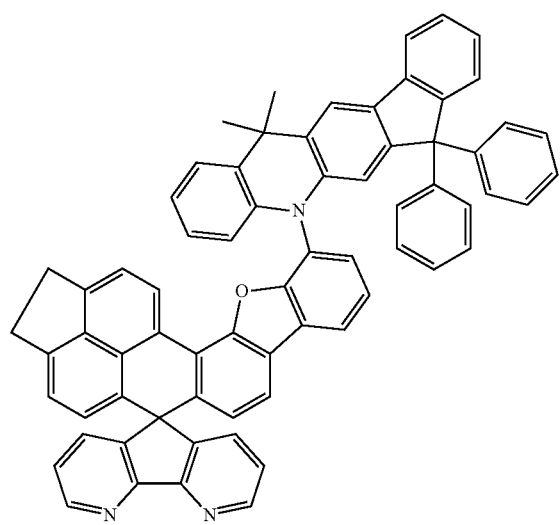
EX73
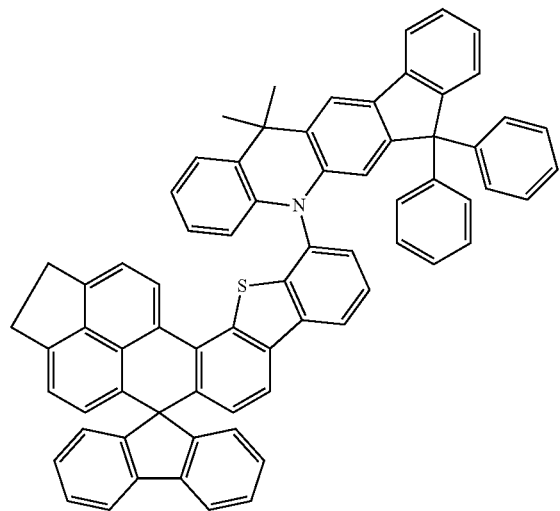
EX74
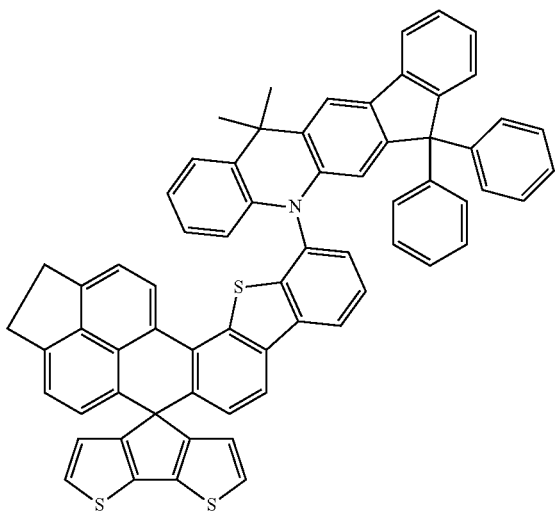
EX75
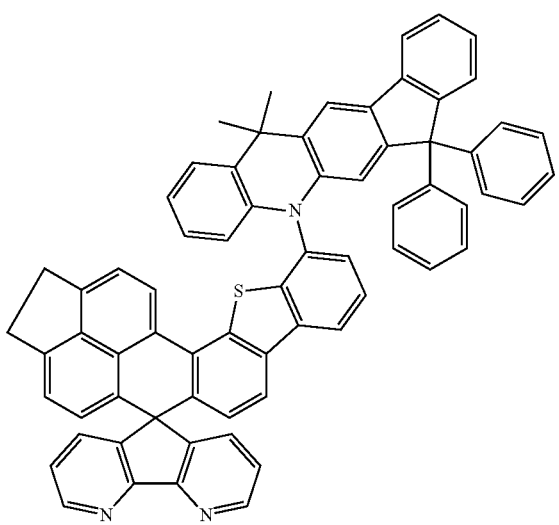
EX76
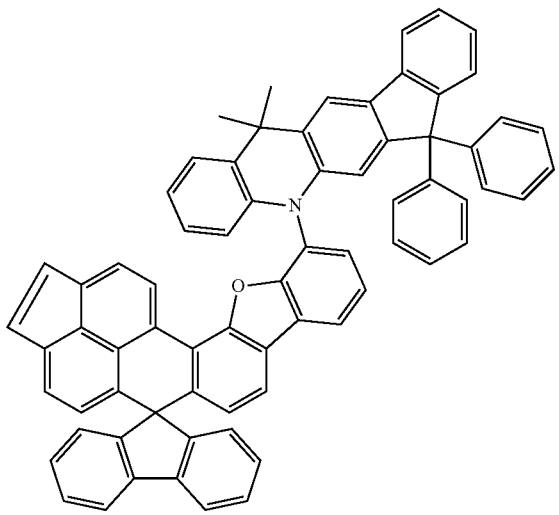

EX77
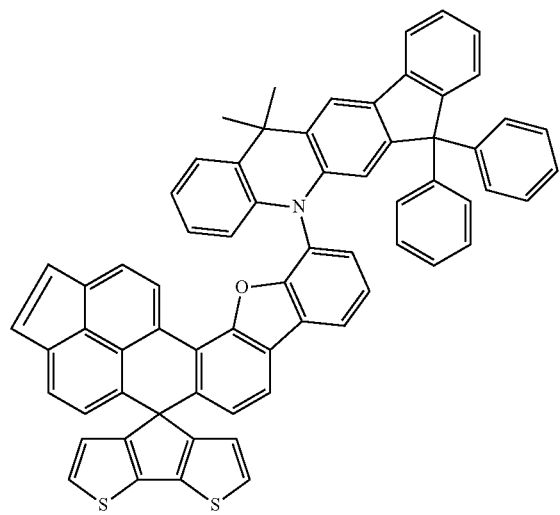
EX78
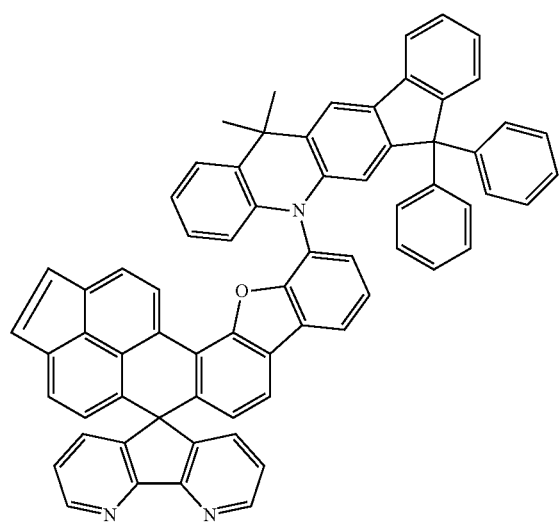
EX79
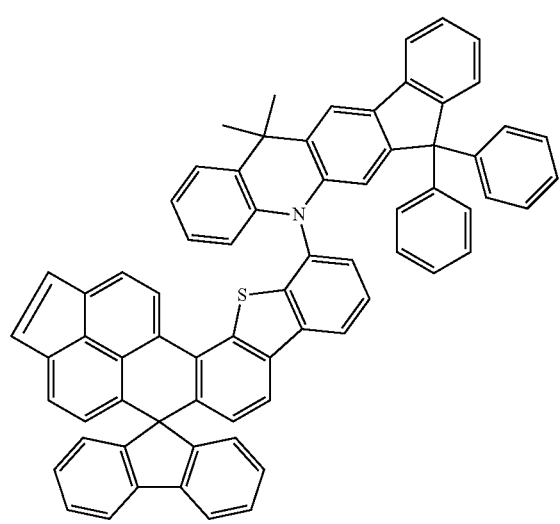
EX80
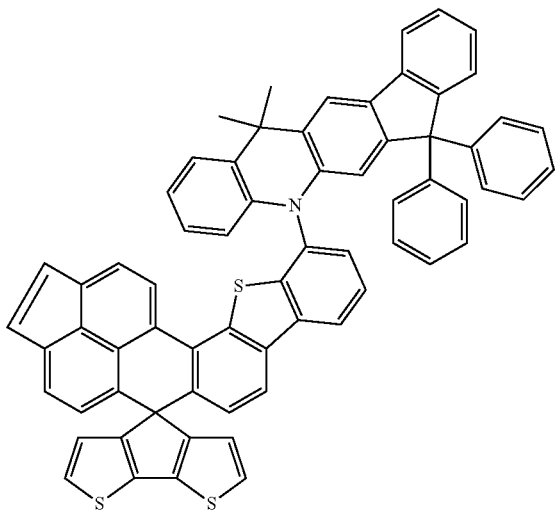
EX81
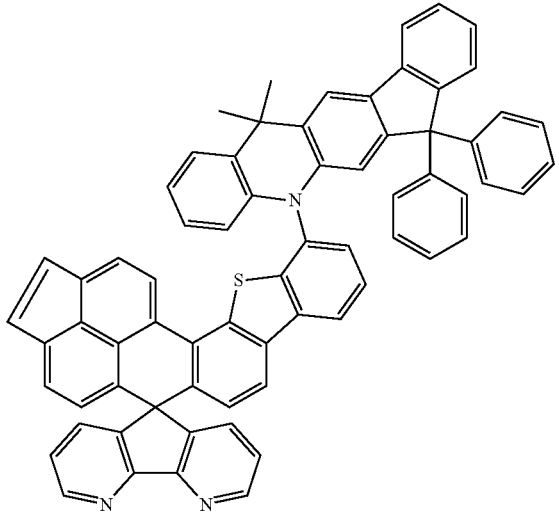
EX82
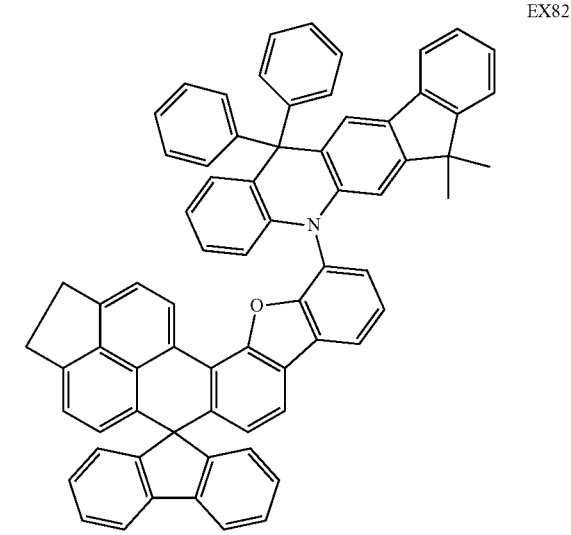

-continued
EX83
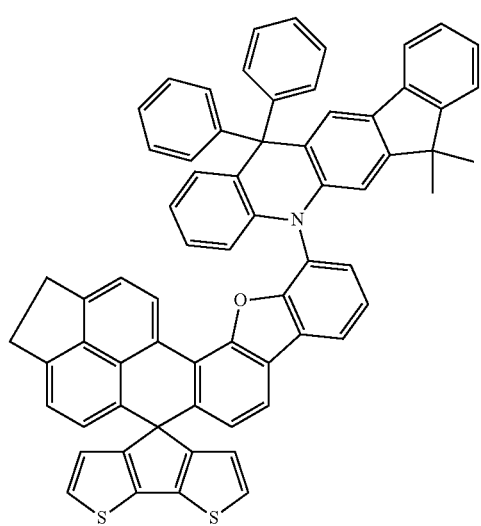
EX86
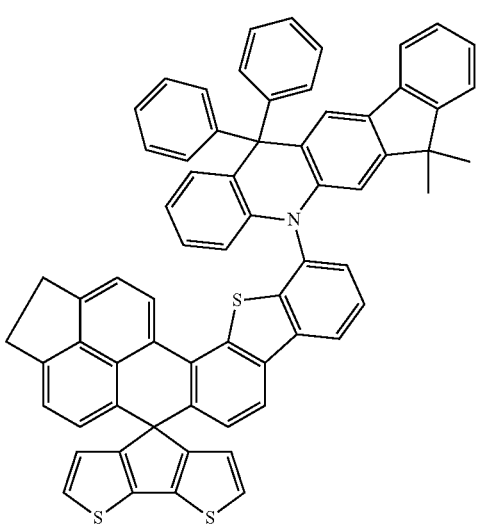
EX84
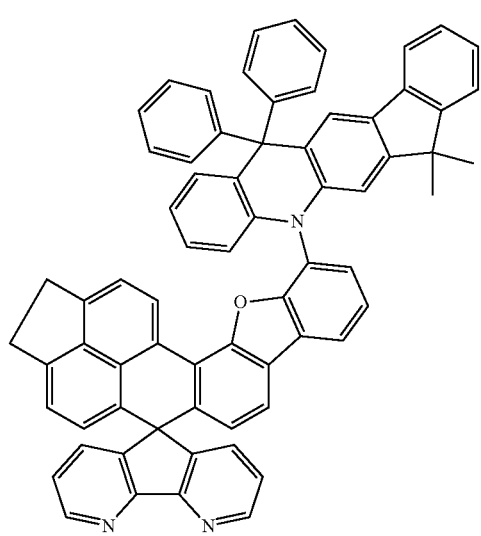
EX87
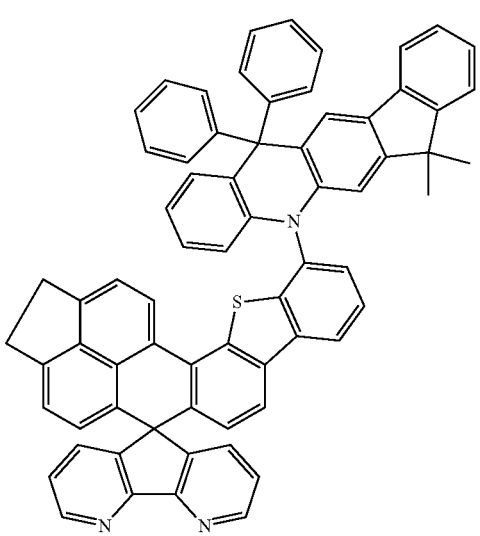
EX85
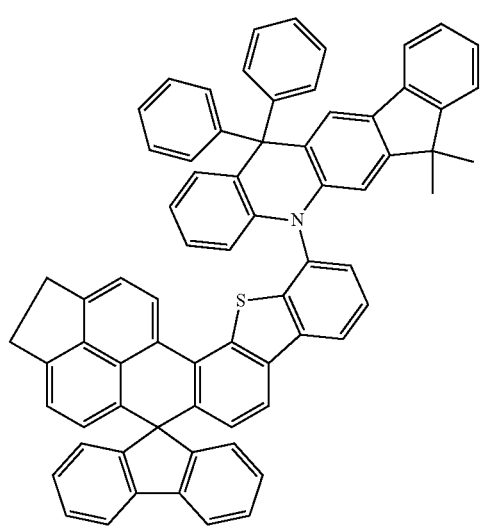
EX88
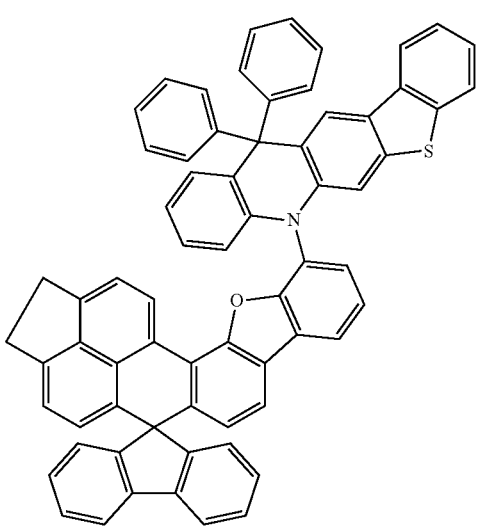

EX89
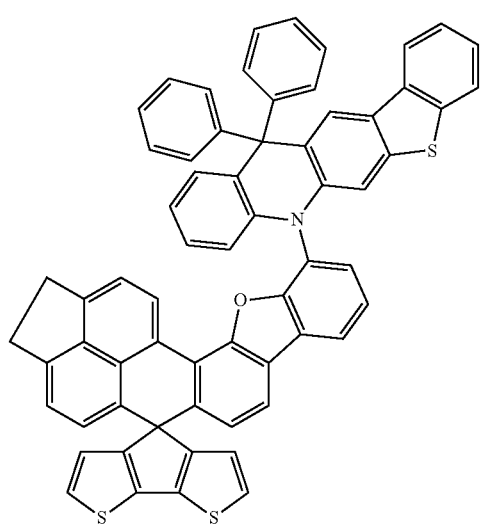
EX92
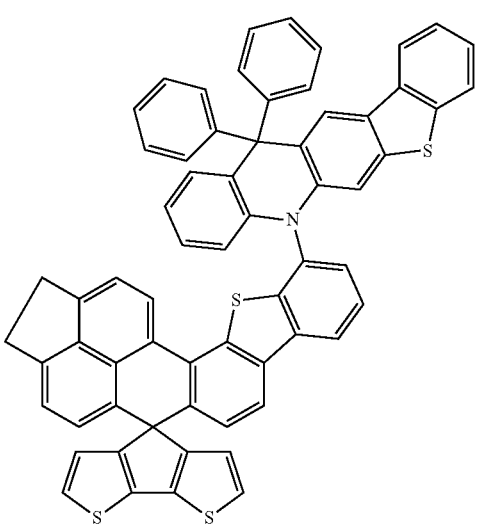
EX90
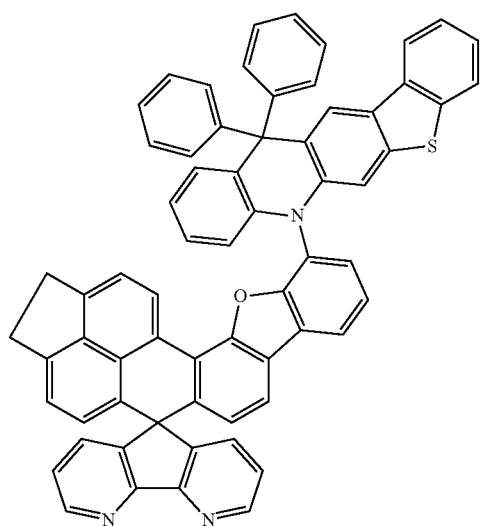
EX93
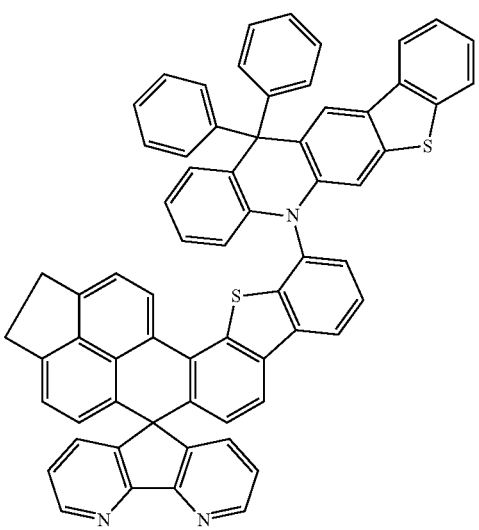
EX91
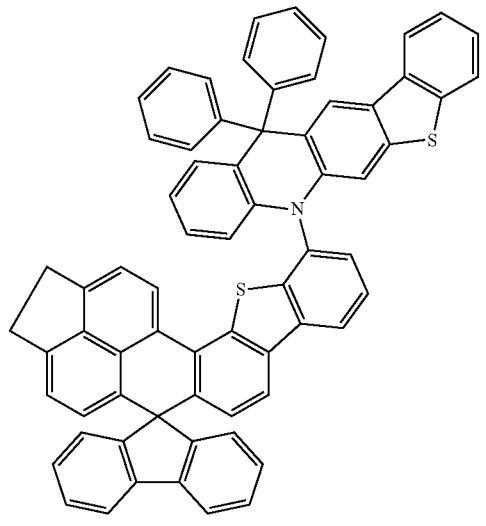
EX94
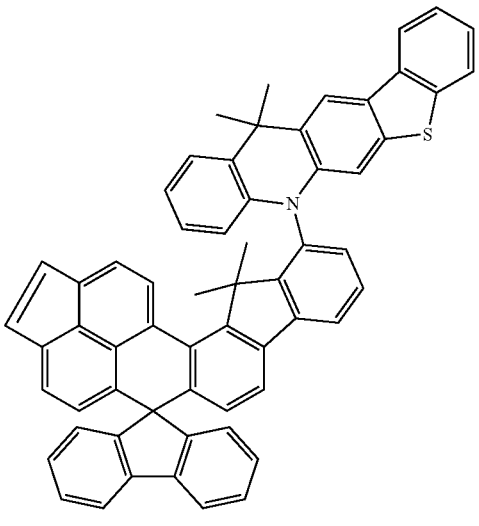

EX95
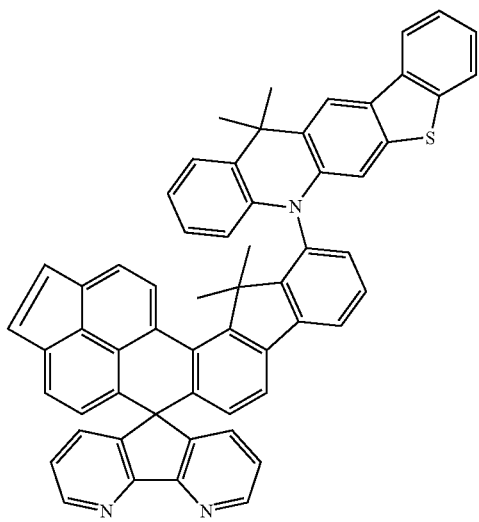
EX96
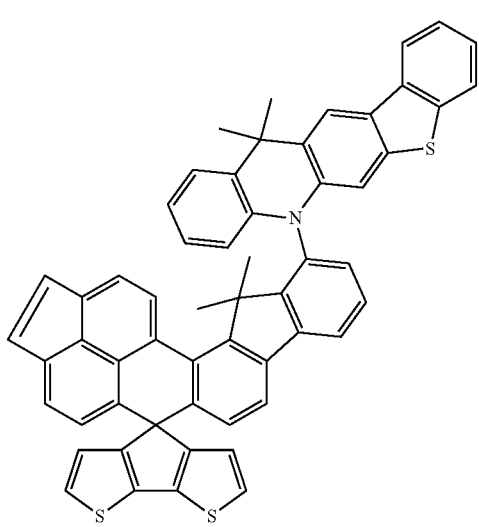
EX97
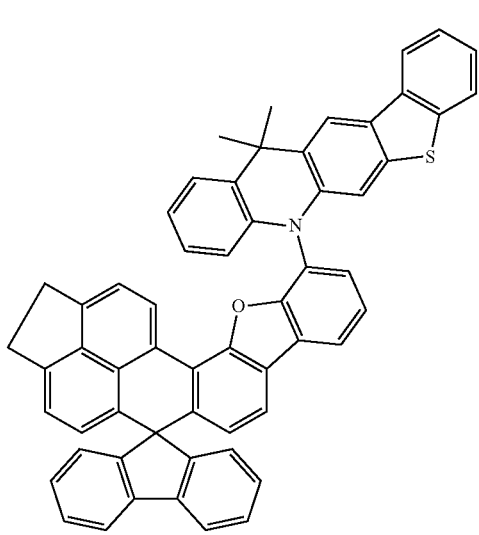
EX98
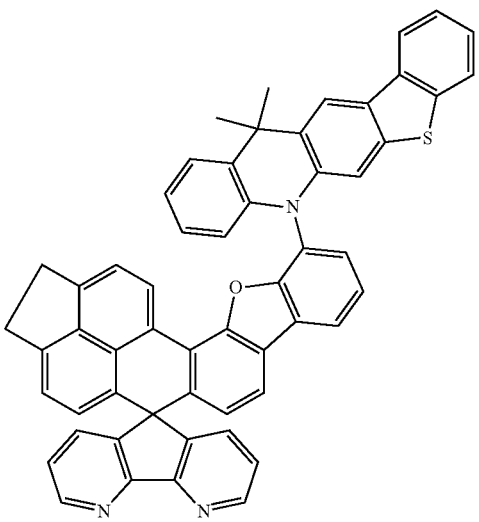
EX99
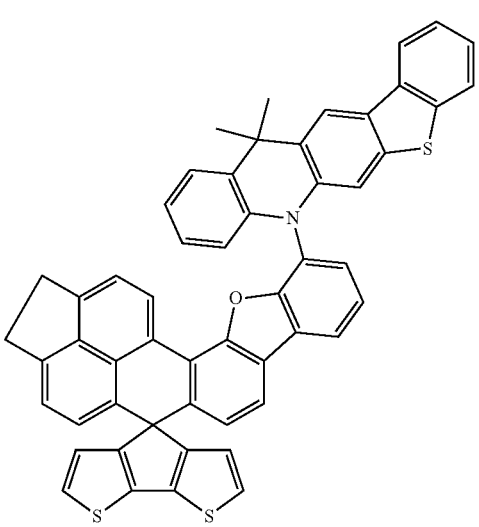
EX100
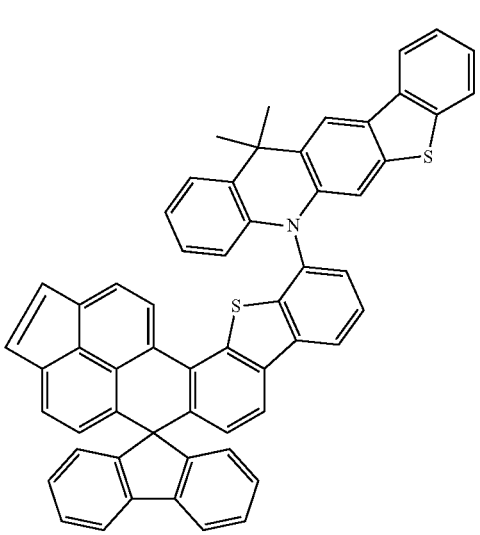

EX101
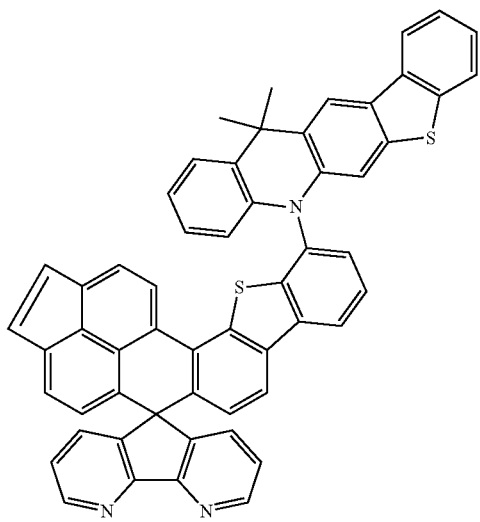
EX102
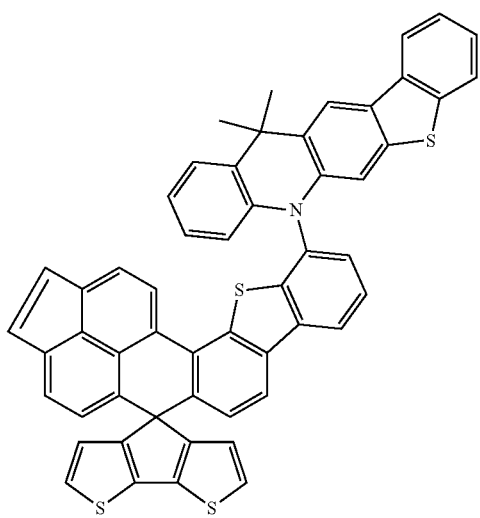
EX103
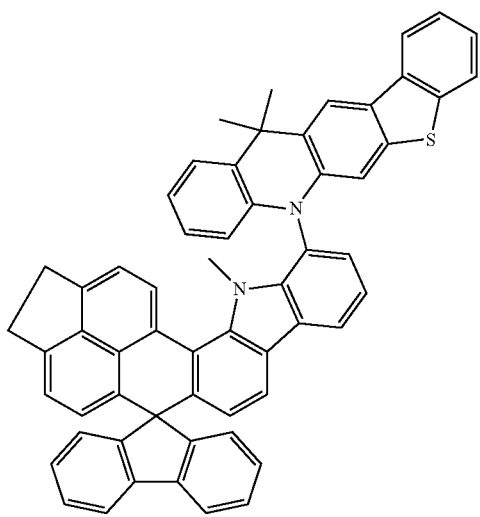
EX104
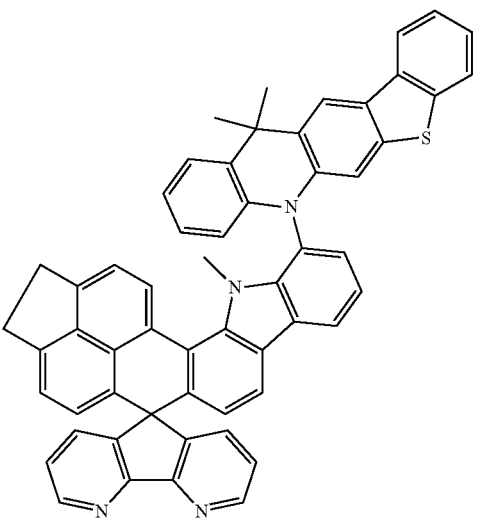
EX105
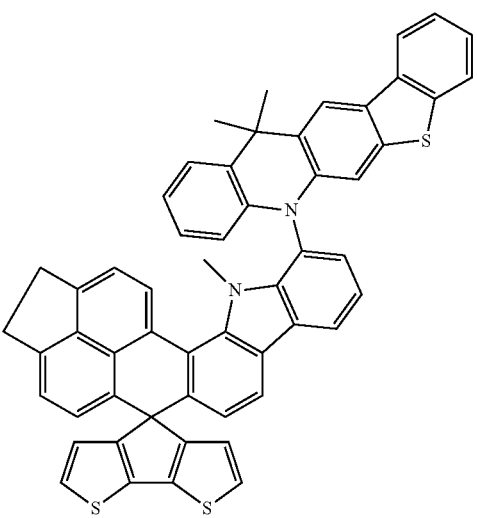
EX106
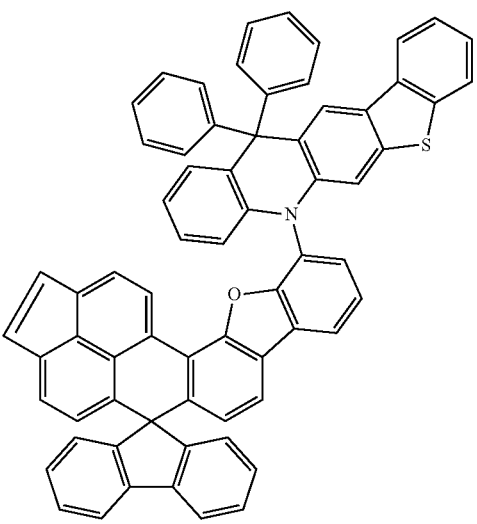

EX107
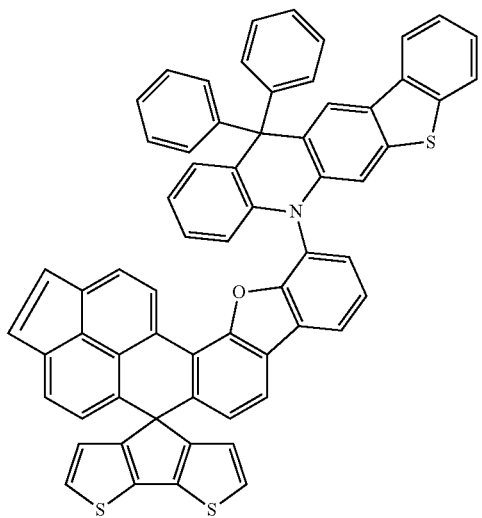
EX110
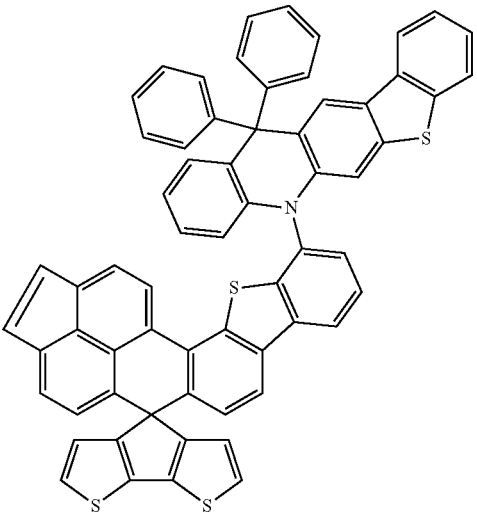
EX108
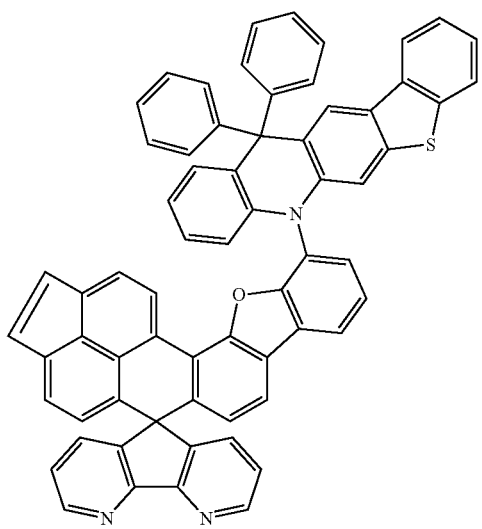
EX111
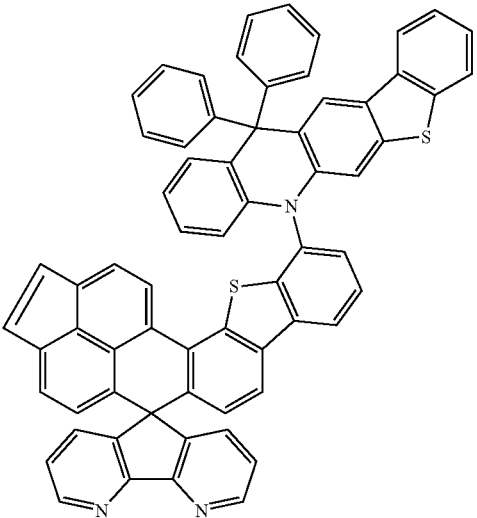
EX109
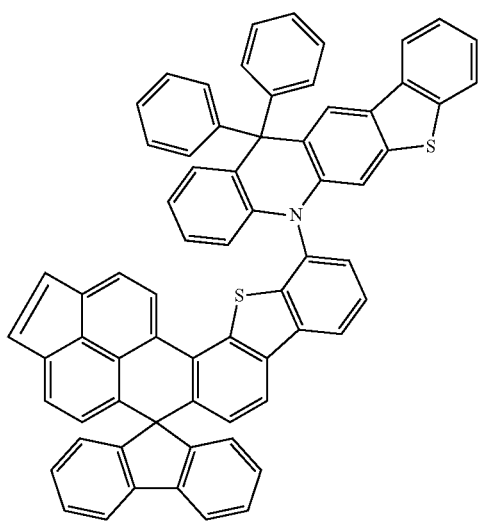
EX112
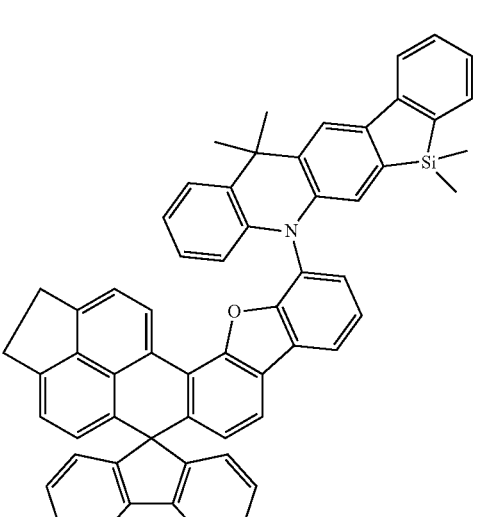

125
-continued
EX113
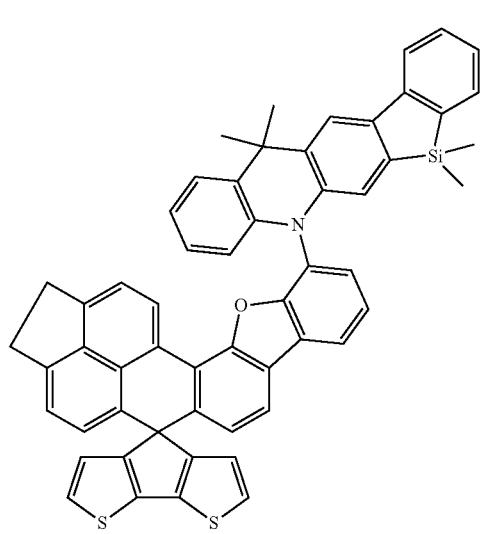
EX114
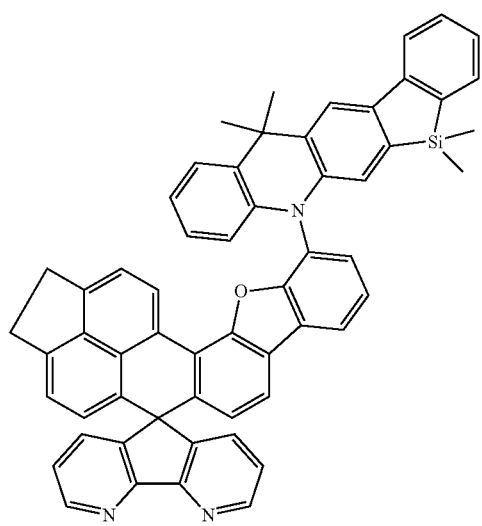
EX115
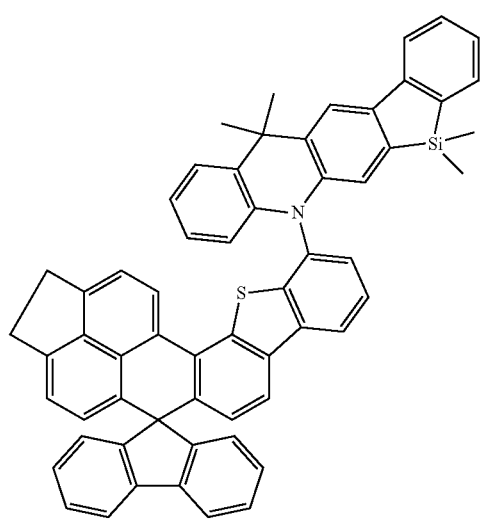
126
-continued
EX116
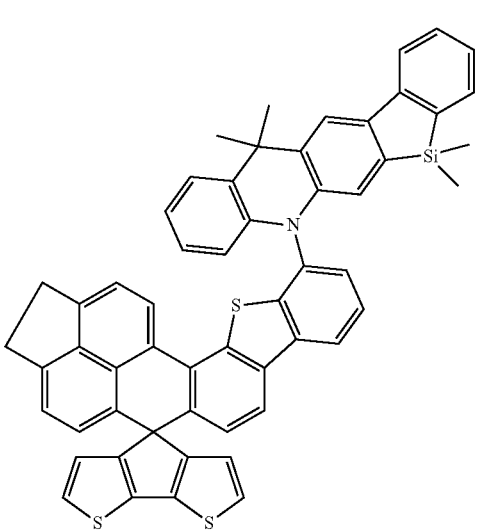
EX117
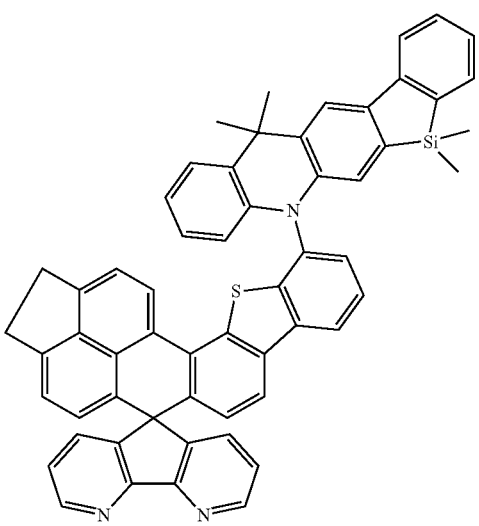
EX118
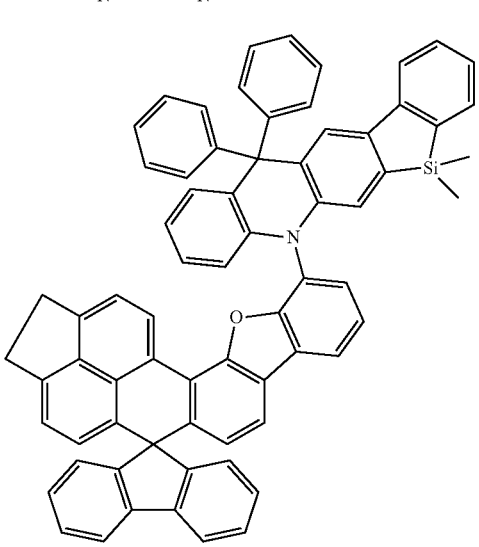

EX119
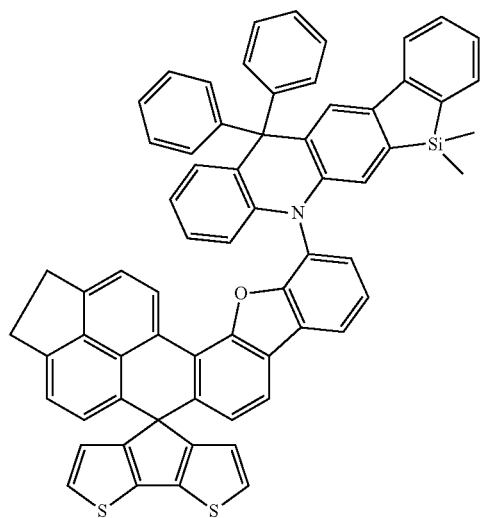
EX120
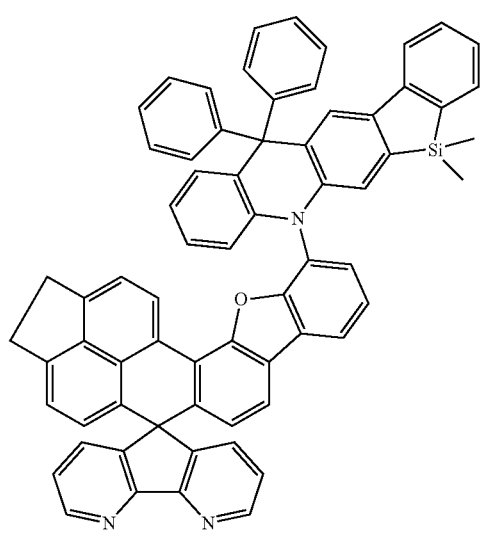
EX121
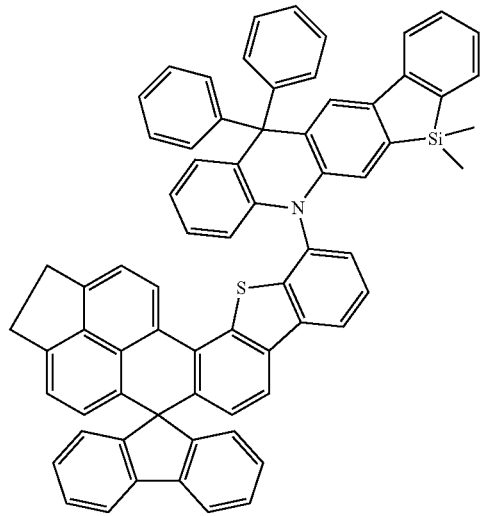
EX122
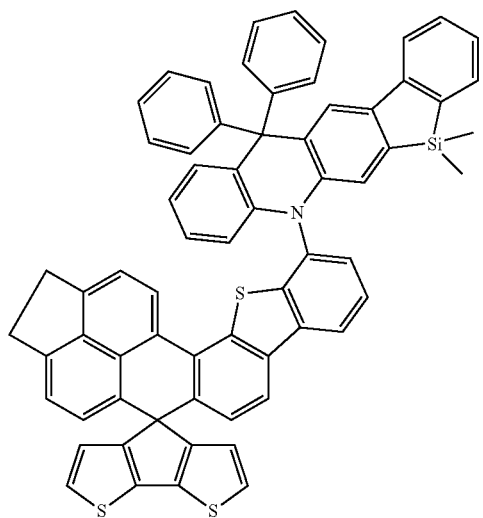
EX123
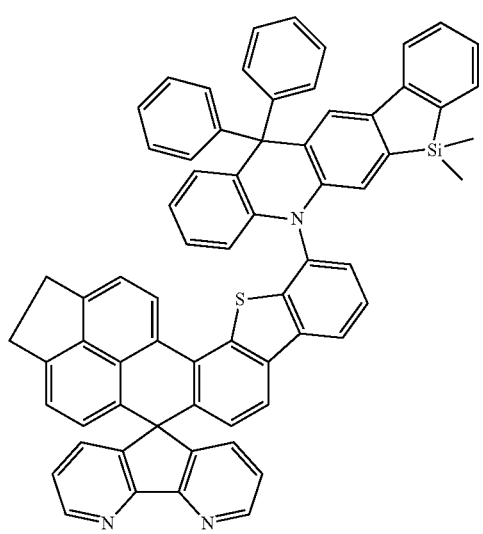
EX124
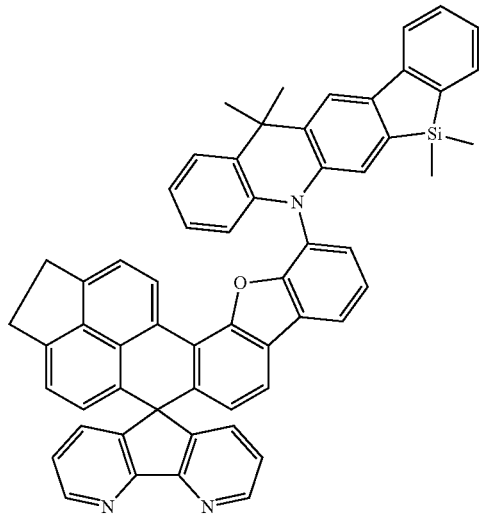

-continued
EX125
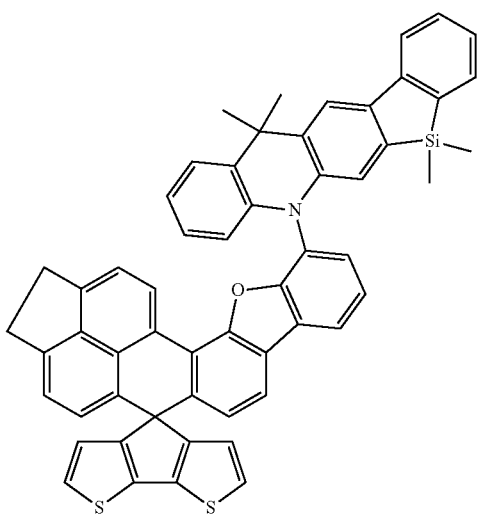
EX128
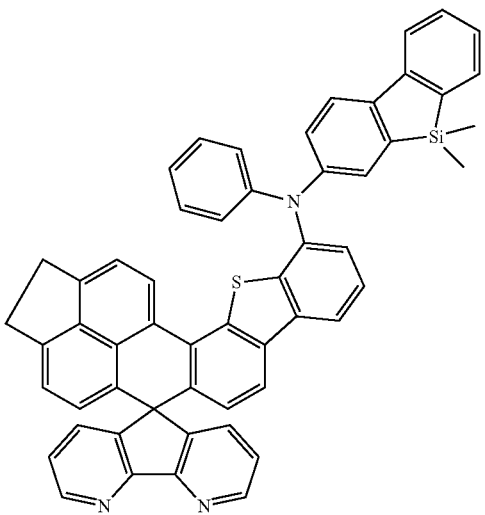
EX126
EX129
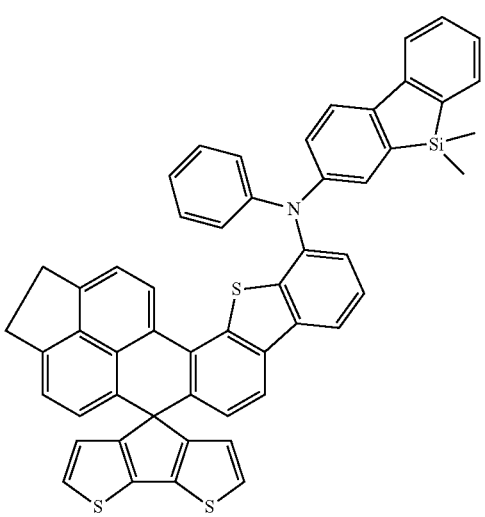
EX127
EX130
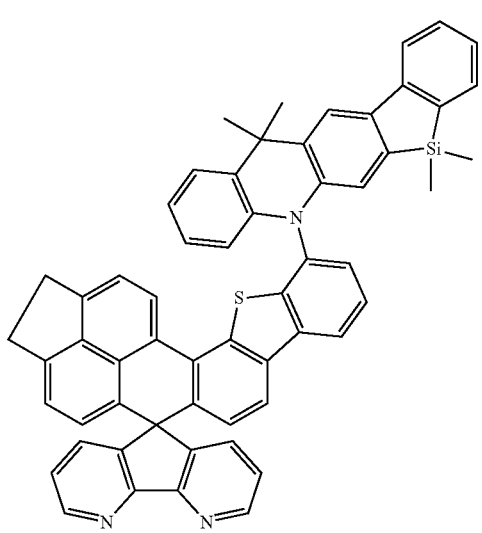

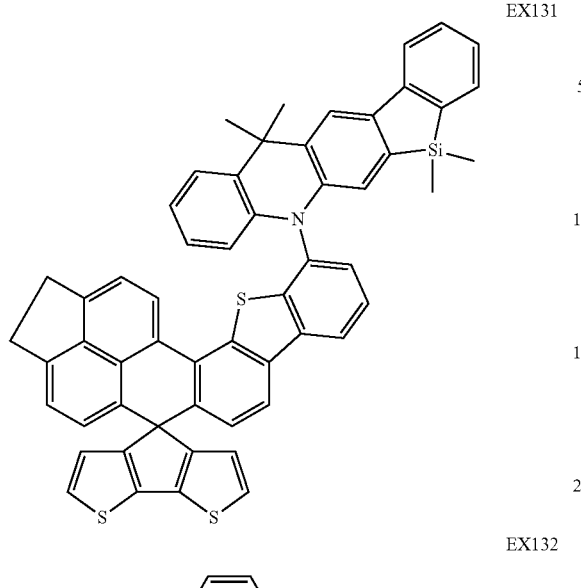
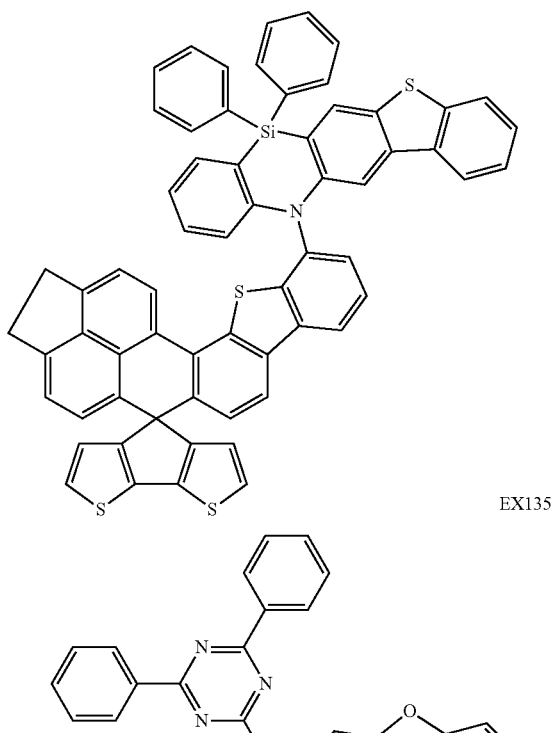
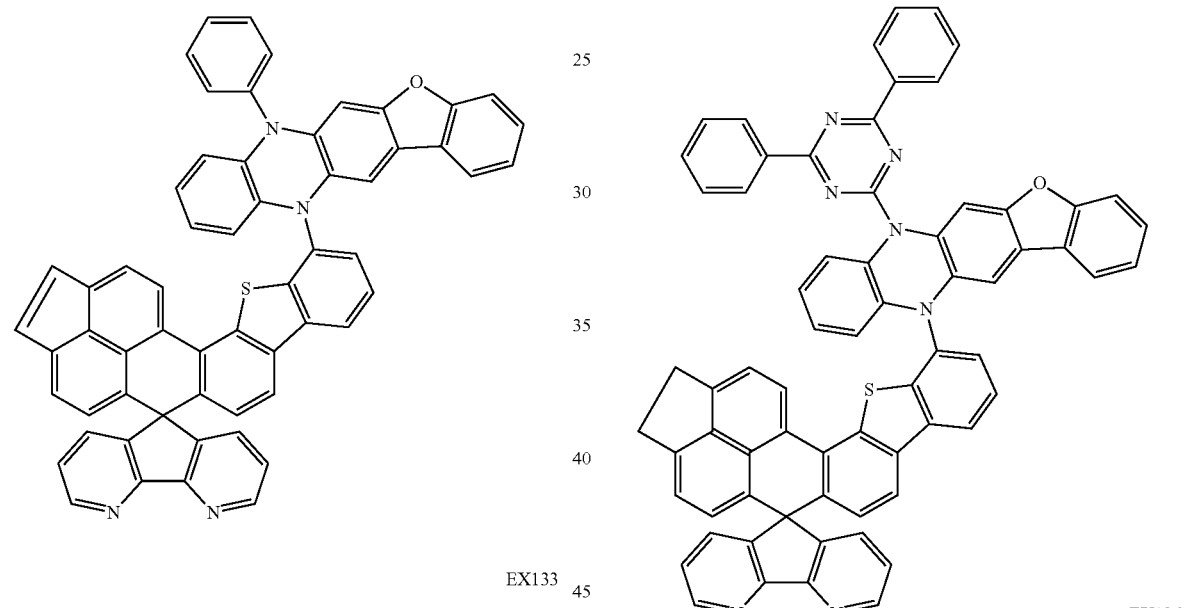

EX137
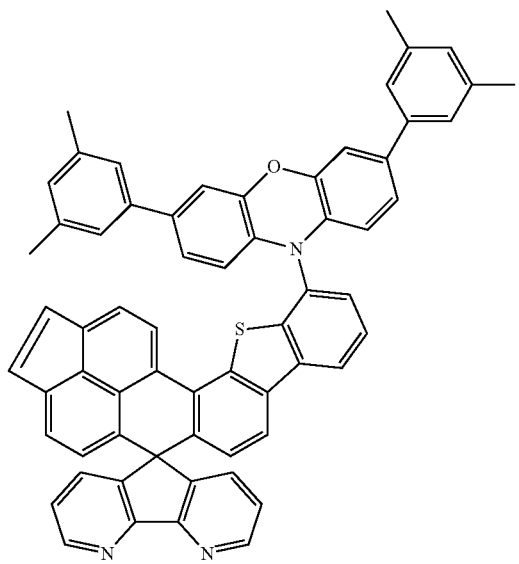
EX138
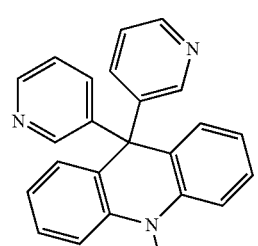
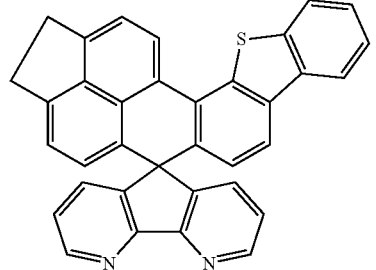
EX139
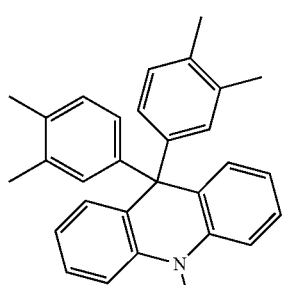
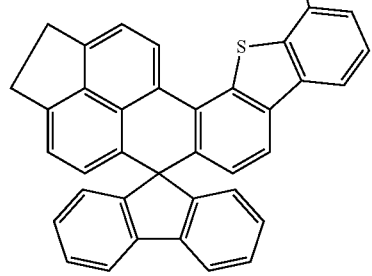
EX140
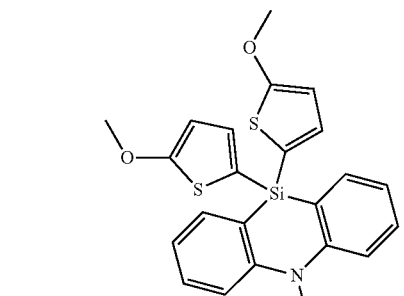
EX141
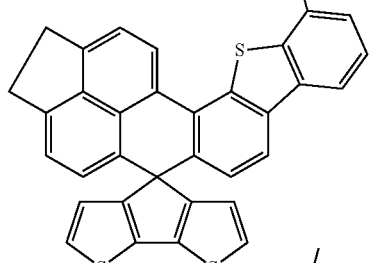
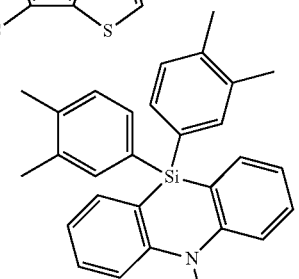
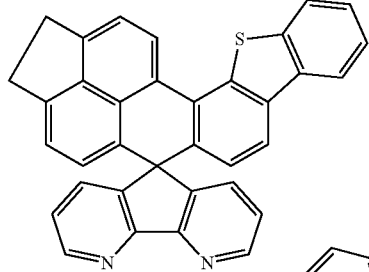
EX142
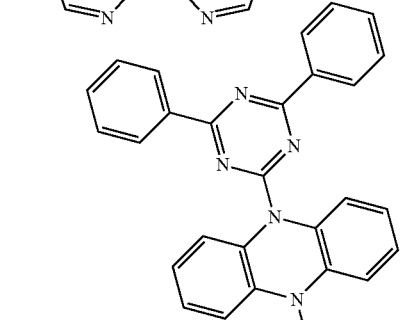
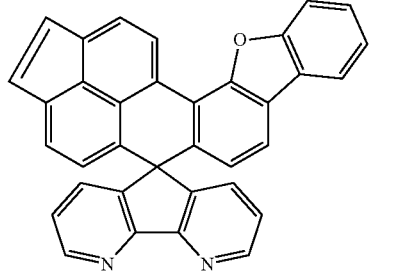

EX143
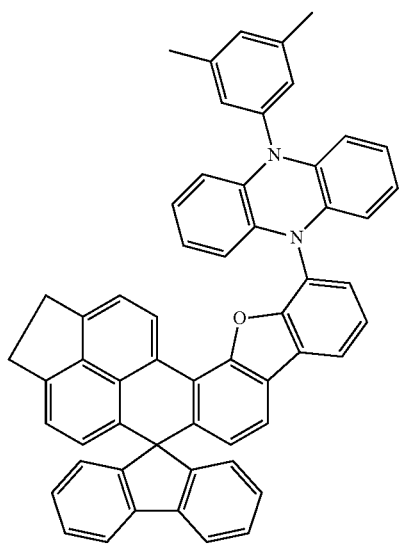
EX144
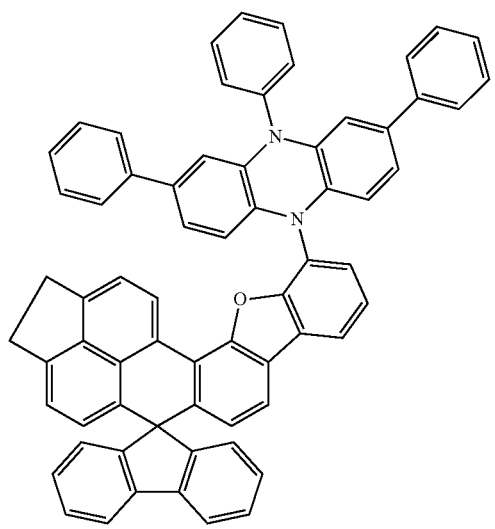
EX145
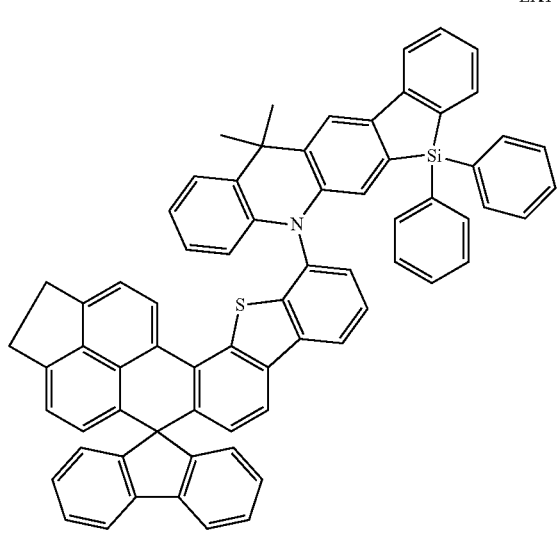
EX146
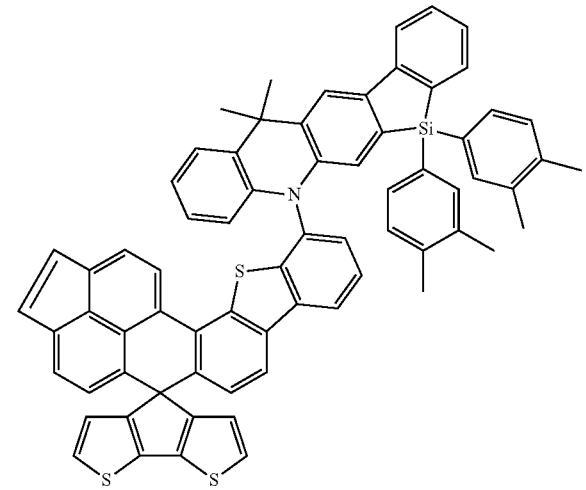
EX147
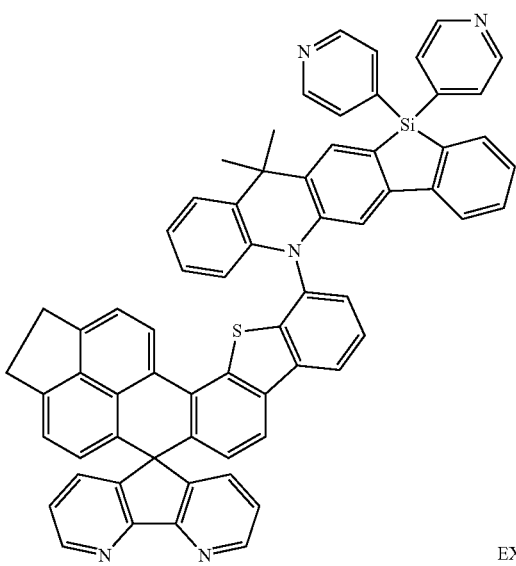
EX148
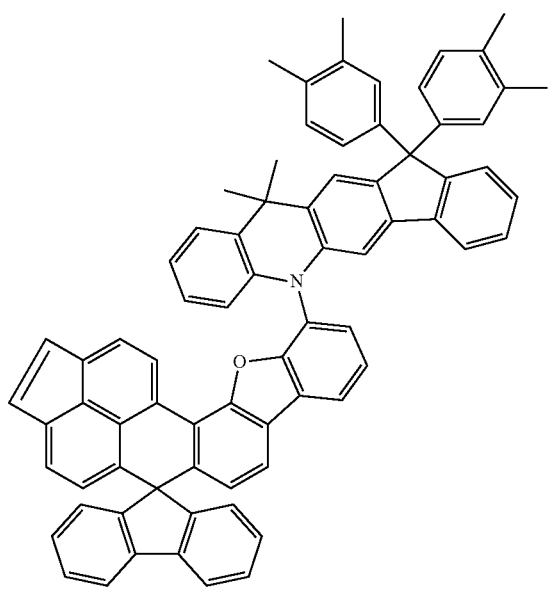

EX149
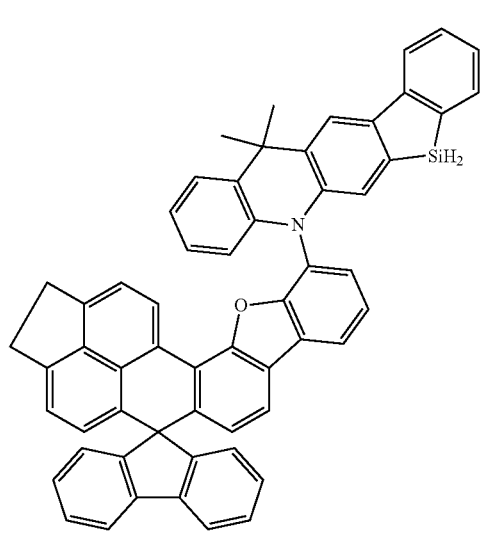
EX150
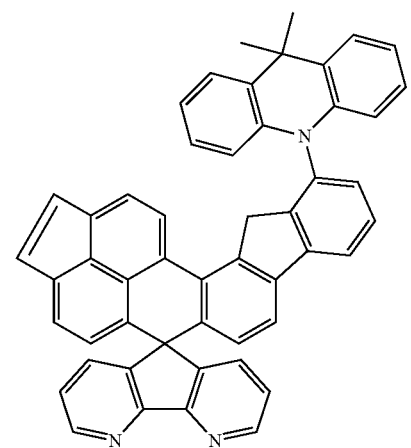
EX151
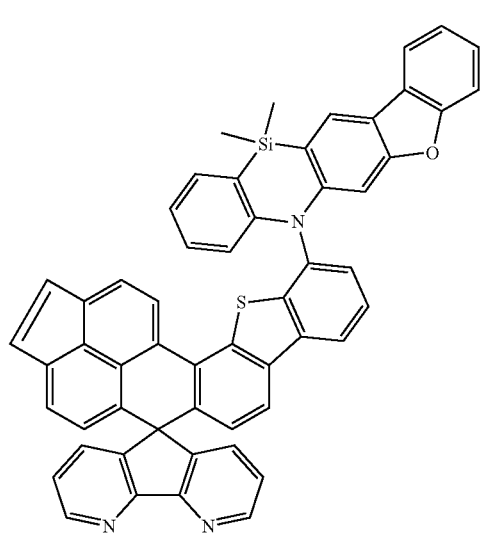
EX152
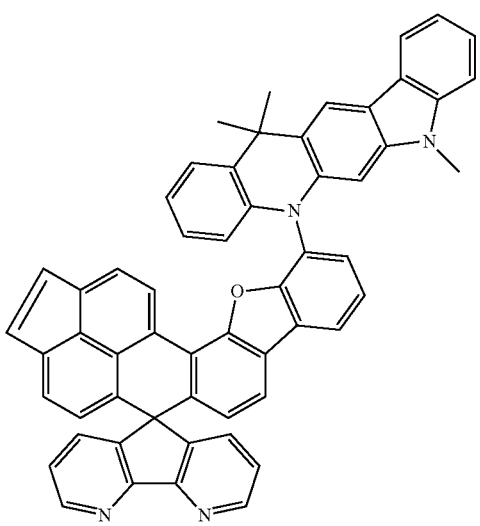
EX153
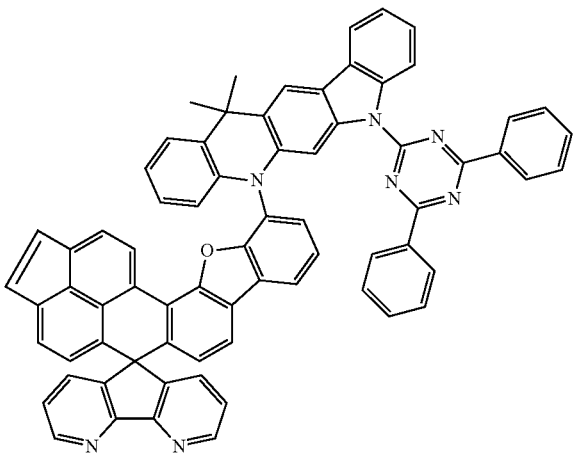
EX154
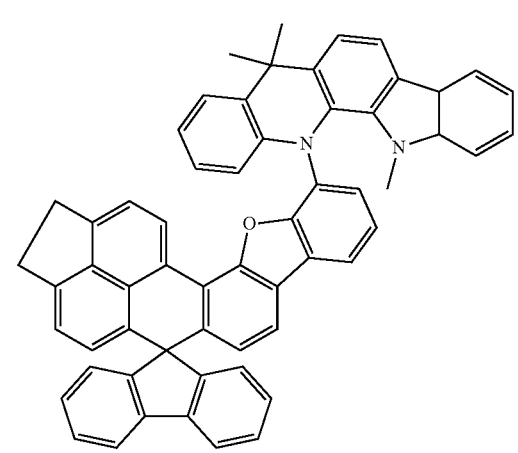

EX155
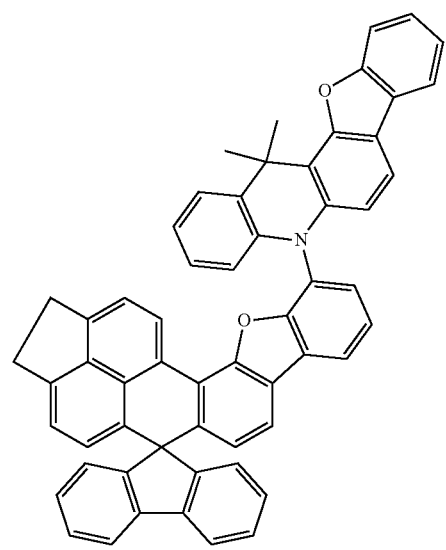
EX156
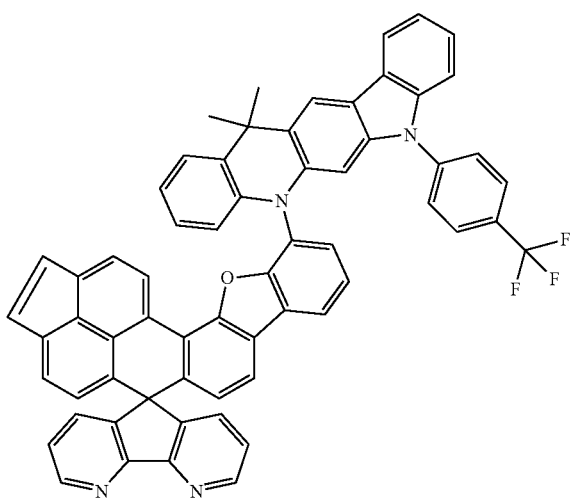
EX157
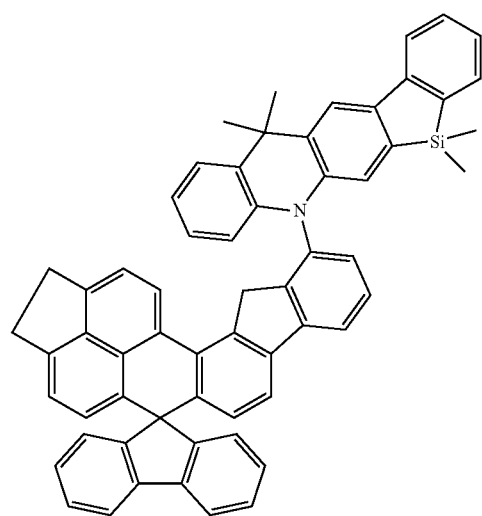
EX158
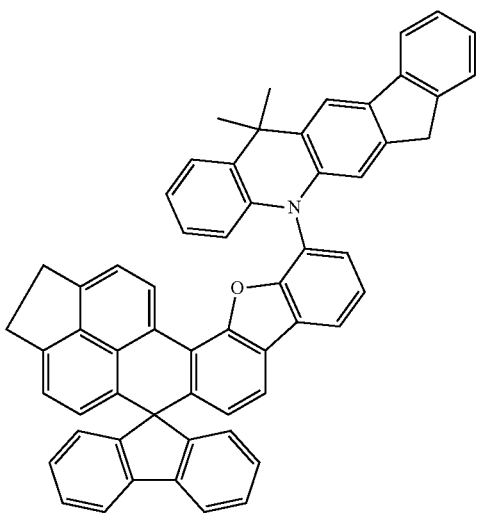
EX159
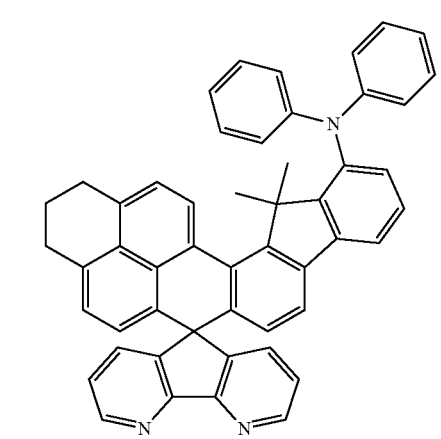
EX160

-continued

EX161
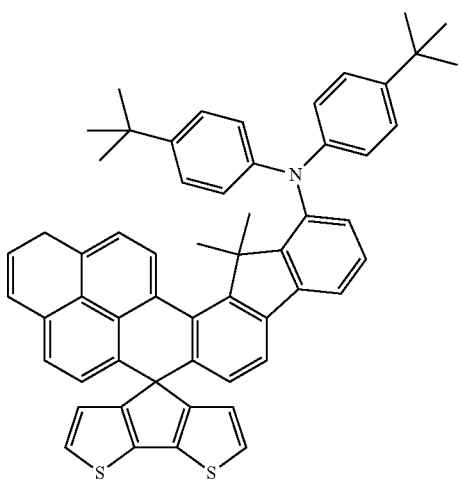

EX162
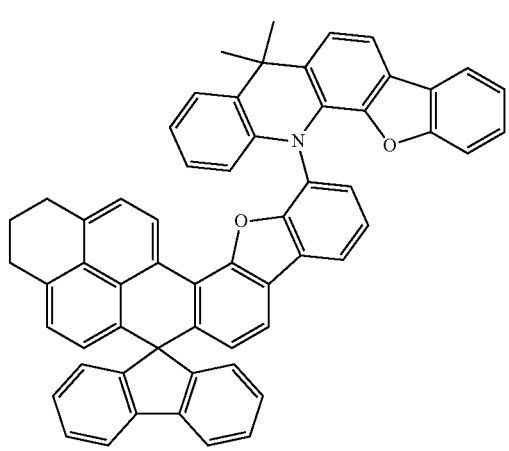

EX163
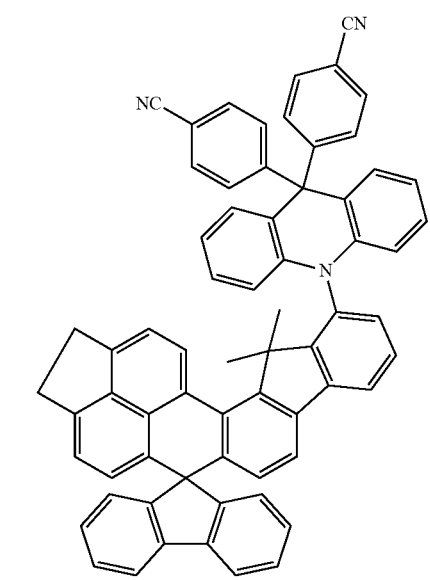

-continued

EX164
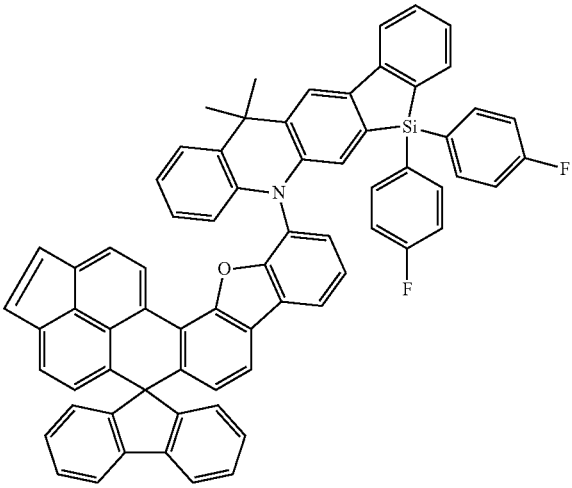

EX165
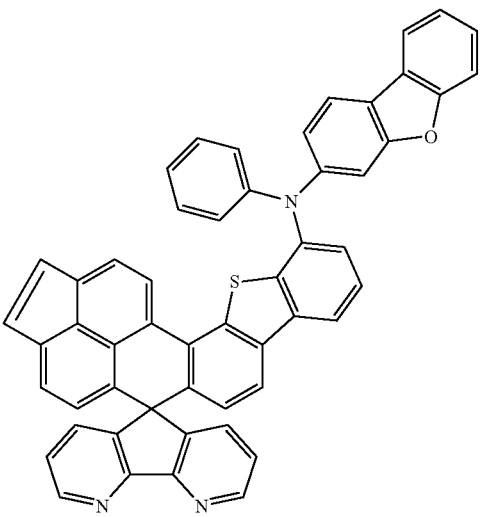

5. An organic electroluminescence device, comprising a pair of electrodes composed of a cathode and an anode, and a light emitting layer between the pair of electrodes, wherein the light emitting layer comprises the heteroaromatic compound according to claim 4.

6. The organic electroluminescence device according to claim 5, wherein the heteroaromatic compound of formula (1) is a fluorescent dopant material.

7. The organic electroluminescence device according to claim 5, wherein the light emitting layer emits blue fluorescence.

8. The organic electroluminescence device according to claim 5, wherein the organic electroluminescence device is a lighting panel.

9. The organic electroluminescence device according to claim 5, wherein the organic electroluminescence device is a backlight panel.

* * * * *